United States Patent
Reiser et al.

(10) Patent No.: US 8,203,001 B2
(45) Date of Patent: Jun. 19, 2012

(54) CHEMICAL COMPOUNDS

(75) Inventors: Ulrich Reiser, Vienna (AT); Peter Ettmayer, Vienna (AT); Oliver Kraemer, Vienna (AT); Peter Sennhenn, Munich (DE); Walter Spevak, Oberrohrbach (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/304,256

(22) PCT Filed: Jun. 13, 2007

(86) PCT No.: PCT/EP2007/055817
§ 371 (c)(1),
(2), (4) Date: Feb. 26, 2009

(87) PCT Pub. No.: WO2007/144370
PCT Pub. Date: Dec. 21, 2007

(65) Prior Publication Data
US 2009/0258857 A1    Oct. 15, 2009

(30) Foreign Application Priority Data
Jun. 14, 2006  (EP) .................................. 06115503

(51) Int. Cl.
*C07D 513/14* (2006.01)
*A61K 31/429* (2006.01)
*C07D 417/12* (2006.01)
*C07D 413/12* (2006.01)
*C07D 401/12* (2006.01)
*C07D 243/08* (2006.01)
*C07D 211/32* (2006.01)
*C07D 419/02* (2006.01)
*A61K 31/5513* (2006.01)
*A61K 31/425* (2006.01)
*A61K 31/497* (2006.01)
*A61K 31/44* (2006.01)
*A61K 31/54* (2006.01)
*A61K 31/5375* (2006.01)

(52) U.S. Cl. .......... 548/151; 544/368; 544/135; 544/80; 544/60; 540/524; 540/575; 546/270.1; 546/199; 514/212.08; 514/366; 514/254.02; 514/278; 514/228.5; 514/218; 514/232.5

(58) Field of Classification Search ........................ None
See application file for complete search history.

(56) References Cited

FOREIGN PATENT DOCUMENTS

| CA | 1097635 A | 3/1981 |
|---|---|---|
| DE | 27 36 652 A1 | 2/1979 |
| DE | 28 33 671 A1 | 2/1980 |
| WO | 01/57008 A1 | 8/2001 |

OTHER PUBLICATIONS

Hartmann et al Angewandte Chemie, International Edition (2001), 40(3), 552-554.*
Katsurra et al Chemical and Pharmaceutical Bulletin (1982), 30(12), 4378-4383.*
Jan E. Blanchard, et al; High-Throughput Screening Identified Inhibitors of the SARS Coronavirus Main Proteinase; Chemistry & Biology (2004) vol. 11 pp. 1445-1453.
Ernest Cullen, et al; Bis Basis Substituted Diaminobenzobisthiazoles as Potential Antiarthritic Agents; American Chemical Society (1992) vol. 35, No. 2 pp. 350-361.
International Search Report for PCT/EP2007/055817 mailed Nov. 26, 2007.

* cited by examiner

*Primary Examiner* — Kamal Saeed
*Assistant Examiner* — Nyeemah A Grazier
(74) *Attorney, Agent, or Firm* — Michael P. Morris; Mary-Ellen M. Devlin

(57) ABSTRACT

The present invention encompasses compounds of general formula (1) wherein $R_1$, $M^1$, $L^1$ and Q are defined as in claim 1, which are suitable for the treatment of diseases characterized by excessive or anomalous cell proliferation, and the use thereof for preparing a pharmaceutical composition with the above-mentioned properties.

(1)

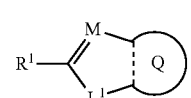

9 Claims, No Drawings

CHEMICAL COMPOUNDS

This application is a national phase entry under 35 U.S.C. 371 of international application PCT/EP2007/055817, filed Jun. 13, 2007, which claims priority to European Application No. EP 06115503.2 filed Jun. 14, 2006, each of which is hereby incorporated by reference in its entirety.

The present invention relates to new heterocyclic compounds of general formula (1)

$$R^1 \underset{L^1}{\overset{M^1}{=}} Q \qquad (1)$$

wherein $R^1$, $L^1$, $M^1$ and Q have the meanings given in the claims and specification, the isomers and salts thereof as well as the use thereof as pharmaceutical compositions.

BACKGROUND TO THE INVENTION

Benzo[1,2-d;5,4-d']bisthiazoles are known as active substances with an antiarthritic and antirheumatic activity from DE 2736652, DE 2833671 and *J. Med. Chem.*, 1992, 35, 350-361 (Cullen et al.) as prior art. WO 01/57008 describes benzothiazoles with an antiproliferative activity.

The aim of the present invention is to indicate new active substances which can be used for the prevention and/or treatment of diseases characterised by excessive or anomalous cell proliferation.

DETAILED DESCRIPTION OF THE INVENTION

Surprisingly it has been found that compounds of general formula (1), wherein $R^1$, $L^1$, $M^1$ and Q have the meanings given hereinafter can be used for the treatment and/or prevention of cancer, infections, inflammations and autoimmune diseases.

The present invention therefore relates to compounds of general formula (1)

$$R^1 \underset{L^1}{\overset{M^1}{=}} Q \qquad (1), \text{ wherein}$$

Q has a partial structure selected from among the partial structures (i)-(iv)

(i)

(ii)

(iii)

(iv)

$L^1$ and $L^2$ each independently of one another denote —O—, —S—, —SO— or —N($R^3$)—,
$M^1$ and $M^2$ each independently of one another denote =N— or =C($R^3$)—,
$X^1$ and $X^2$ each independently of one another denote =N— or =C($R^{4a}$)— and
$Y^1$ and $Y^2$ each independently of one another denote —O—, —S—, —SO—, —SO$_2$—, —C($R^{4a}$)($R^{4b}$)— or —N($R^{4a}$)—,
$R^1$ and $R^2$ independently of one another are selected from among —NR$^a$R$^a$, —N(OR$^a$)R$^a$, —N(R$^g$)NR$^a$R$^a$, —N(R$^g$)S(O)R$^a$, —N(R$^g$)S(O)$_2$R$^a$, —N[S(O)$_2$R$^a$]$_2$, —N(R$^g$)S(O)$_2$OR$^a$, —N(R$^g$)S(O)$_2$NR$^a$R$^a$, —N(R$^g$)S(O)OR$^a$, —N(R$^g$)C(O)R$^a$, —N[C(O)R$^a$]$_2$, —N(R$^g$)C(S)R$^a$, —N[C(O)R$^a$]NR$^a$R$^a$, —N(R$^g$)N(R$^g$)C(O)R$^a$, —N(OR$^a$)C(O)R$^a$, —N(R$^g$)C(NOH)R$^a$, —N(R$^g$)C(NR$^g$)R$^a$, —N(R$^g$)C(O)OR$^a$, —N(R$^g$)C(O)SR$^a$, —N(R$^g$)C(O)NR$^a$R$^a$, —N(R$^g$)C(S)NR$^a$R$^a$, —N(R$^g$)C(O)NR$^g$NR$^a$R$^a$, —N(R$^g$)N(R$^g$)C(O)NR$^a$R$^a$, —N(R$^g$)C(NR$^g$)OR$^a$, —N(R$^g$)C(NR$^g$)SR$^a$, —N(R$^g$)C(NR$^g$)NR$^a$R$^a$, —[N(R$^g$)C(O)]$_2$R$^a$, —N(R$^g$)[C(O)]$_2$R$^a$, —N{[C(O)]$_2$R$^a$}$_2$, —N(R$^g$)[C(O)]$_2$OR$^a$, —N(R$^g$)[C(O)]$_2$NR$^a$R$^a$, —N{[C(O)]$_2$OR$^a$}$_2$, —N{[C(O)]$_2$NR$^a$R$^a$}$_2$, —[N(R$^g$)C(O)]$_2$OR$^a$ and a nitrogen-containing 3-8 membered heterocycloalkyl attached via a cyclic nitrogen, this heterocycloalkyl optionally being substituted by one or more identical or different group(s) selected from among R$^a$ and R$^b$
each R$^3$, R$^{4a}$ and R$^{4b}$ independently of one another is selected from among R$^a$ and R$^b$,
each R$^a$ independently of one another denotes hydrogen or a group optionally substituted by one or more identical or different R$^b$ and/or R$^c$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl,
each R$^b$ is a suitable group and is selected in each case independently of one another from among =O, —OR$^c$, $C_{1-3}$haloalkyloxy, —OCF$_3$, =S, —SR$^c$, =NR$^c$, =NOR$^c$, =NNR$^c$R$^c$, =NN(R$^g$)C(O)NR$^c$R$^c$, NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O)R$^c$, —S(O)OR$^c$, —S(O)₂Rᶜ, —S(O)₂ORᶜ, —S(O)NRᶜRᶜ, —S(O)₂NRᶜRᶜ, —OS(O)Rᶜ, —OS(O)₂Rᶜ, —OS(O)₂ORᶜ, —OS(O)NRᶜRᶜ, —OS(O)₂NRᶜRᶜ, —C(O)Rᶜ, —C(O)ORᶜ, —C(O)SRᶜ, —C(O)NRᶜRᶜ, —C(O)N(Rᵍ)NRᶜRᶜ, —C(O)N(Rᵍ)ORᶜ, —C(NRᵍ)NRᶜRᶜ, —C(NOH)Rᶜ, —C(NOH)NRᶜRᶜ, —OC(O)Rᶜ, —OC(O)ORᶜ, —OC(O)SRᶜ, —OC(O)NRᶜRᶜ, —OC(NRᵍ)NRᶜRᶜ, —SC(O)Rᶜ, —SC(O)ORᶜ, —SC(O)NRᶜRᶜ, —SC(NRᵍ)NRᶜRᶜ, —N(Rᵍ)C(O)Rᶜ, —N[C(O)Rᶜ]₂, —N(ORᵍ)C(O)Rᶜ, —N(Rᵍ)C(NRᵍ)Rᶜ, —N(Rᵍ)N(Rᵍ)C(O)Rᶜ, —N[C(O)Rᶜ]NRᶜRᶜ, —N(Rᵍ)C(S)Rᶜ, —N(Rᵍ)S(O)Rᶜ, —N(Rᵍ)S(O)ORᶜ, —N(Rᵍ)S(O)₂Rᶜ, —N[S(O)₂Rᶜ]₂, —N(Rᵍ)S(O)₂ORᶜ, —N(Rᵍ)S(O)₂NRᶜRᶜ, —N(Rᵍ) [S(O)₂]₂Rᶜ, —N(Rᵍ)C(O)ORᶜ, —N(Rᵍ)C(O)SRᶜ, —N(Rᵍ)C(O)NRᶜRᶜ, —N(Rᵍ)C(O)NRᵍNRᶜRᶜ, —N(Rᵍ)N(Rᵍ)C(O)NRᶜRᶜ, —N(Rᵍ)C(S)NRᶜRᶜ, —[N(Rᵍ)C(O)]₂Rᶜ, —N(Rᵍ) [C(O)]₂Rᶜ, —N{[C(O)]₂Rᶜ}₂, —N(Rᵍ)[C(O)]₂ORᶜ, —N(Rᵍ)[C(O)]₂ NRᶜRᶜ, —N{[C(O)]₂ORᶜ}₂, —N{[C(O)]₂NRᶜRᶜ}₂, —[N(Rᵍ)C(O)]₂ORᶜ, —N(Rᵍ)C(NRᵍ)ORᶜ, —N(Rᵍ)C(NOH)Rᶜ, —N(Rᵍ)C(NRᵍ)SRᶜ and —N(Rᵍ)C(NRᵍ)NRᶜRᶜ, each Rᶜ independently of one another denotes hydrogen or a group optionally substituted by one or more identical or different Rᵈ and/or Rᵉ, selected from among C₁₋₆alkyl, 2-6 membered heteroalkyl, C₁₋₆haloalkyl, C₃₋₁₀cycloalkyl, C₄₋₁₆cycloalkylalkyl, C₆₋₁₀aryl, C₇₋₁₆arylalkyl, 5-12 membered heteroaryl, 6-18 membered heteroarylalkyl, 3-14 membered heterocycloalkyl and 4-14 membered heterocycloalkylalkyl, each Rᵈ is a suitable group and is selected in each case independently of one another from among =O, —ORᵉ, C₁₋₃haloalkyloxy, —OCF₃, =S, —SRᵉ, =NRᵉ, =NORᵉ, =NNRᵉRᵉ, =NN(Rᵍ)C(O)NRᵉRᵉ, —NRᵉRᵉ, —ONRᵉRᵉ, —N(Rᵍ)NRᵉRᵉ, halogen, —CF₃, —CN, —NC, —OCN, —SCN, —NO, —NO₂, =N₂, —N₃, —S(O)Rᵉ, —S(O)ORᵉ, —S(O)₂Rᵉ, —S(O)₂ORᵉ, —S(O)NRᵉRᵉ, —S(O)₂NRᵉRᵉ, —OS(O)Rᵉ, —OS(O)₂Rᵉ, —OS(O)₂ORᵉ, —OS(O)NRᵉRᵉ, —OS(O)₂NRᵉRᵉ, —C(O)Rᵉ, —C(O)ORᵉ, —C(O)SRᵉ, —C(O)NRᵉRᵉ, —C(O)N(Rᵍ)NRᵉRᵉ, —C(O)N(Rᵍ)ORᵉ, —C(NRᵍ)NRᵉRᵉ, —C(NOH)Rᵉ, —C(NOH)NRᵉRᵉ, —OC(O)Rᵉ, —OC(O)ORᵉ, —OC(O)SRᵉ, —OC(O)NRᵉRᵉ, —OC(NRᵍ)NRᵉRᵉ, —SC(O)Rᵉ, —SC(O)ORᵉ, —SC(O)NRᵉRᵉ, —SC(NRᵍ)NRᵉRᵉ, —N(Rᵍ)C(O)Rᵉ, —N[C(O)Rᵉ]₂, —N(ORᵍ)C(O)Rᵉ, —N(Rᵍ)C(NRᵍ)Rᵉ, —N(Rᵍ)N(Rᵍ)C(O)Rᵉ, —N[C(O)Rᵉ]NRᵉRᵉ, —N(Rᵍ)C(S)Rᵉ, —N(Rᵍ)S(O)Rᵉ, —N(Rᵍ)S(O)ORᵉ, —N(Rᵍ)S(O)₂Rᵉ, —N[S(O)₂Rᵉ]₂, —N(Rᵍ)S(O)₂ORᵉ, —N(Rᵍ)S(O)₂NRᵉRᵉ, —N(Rᵍ)[S(O)₂]₂Rᵉ, —N(Rᵍ)C(O)ORᵉ, —N(Rᵍ)C(O)SRᵉ, —N(Rᵍ)C(O)NRᵉRᵉ, —N(Rᵍ)C(O)NRᵍNRᵉRᵉ, —N(Rᵍ)N(Rᵍ)C(O)NRᵉRᵉ, —N(Rᵍ)C(S)NRᵉRᵉ, —[N(Rᵍ)C(O)]₂Rᵉ, —N(Rᵍ)[C(O)]₂Rᵉ, —N{[C(O)]₂Rᵉ}₂, —N(Rᵍ)[C(O)]₂ORᵉ, —N(Rᵍ)[C(O)]₂NRᵉRᵉ, —N{[C(O)]₂ORᵉ}₂, —N{[C(O)]₂NRᵉRᵉ}₂, —[N(Rᵍ)C(O)]₂ORᵉ, —N(Rᵍ)C(NRᵍ)ORᵉ, —N(Rᵍ)C(NOH)Rᵉ, —N(Rᵍ)C(NRᵍ)SRᵉ and —N(Rᵍ)C(NRᵍ)NRᵉRᵉ, each Rᵉ independently of one another denotes hydrogen or a group optionally substituted by one or more identical or different Rᶠ and/or Rᵍ, selected from among C₁₋₆alkyl, 2-6 membered heteroalkyl, C₁₋₆haloalkyl, C₃₋₁₀cycloalkyl, C₄₋₁₆cycloalkylalkyl, C₆₋₁₀aryl, C₇₋₁₆arylalkyl, 5-12 membered heteroaryl, 6-18 membered heteroarylalkyl, 3-14 membered heterocycloalkyl and 4-14 membered heterocycloalkylalkyl, each Rᶠ is a suitable group and is selected in each case independently of one another from among =O, —ORᵍ, C₁₋₃haloalkyloxy, —OCF₃, =S, —SRᵍ, =NRᵍ, =NORᵍ, =NNRᵍRᵍ, =NN(Rʰ)C(O)NRᵍRᵍ, —NRᵍRᵍ, —ONRᵍRᵍ, —N(Rʰ)NRᵍRᵍ, halogen, —CF₃, —CN, —NC, —OCN, —SCN, —NO, —NO₂, =N₂, —N₃, —S(O)Rᵍ, —S(O)ORᵍ, —S(O)₂Rᵍ, —S(O)₂ORᵍ, —S(O)NRᵍRᵍ, —S(O)₂NRᵍRᵍ, —OS(O)Rᵍ, —OS(O)₂Rᵍ, —OS(O)₂ORᵍ, —OS(O)NRᵍRᵍ, —OS(O)₂ NRᵍRᵍ, —C(O)Rᵍ, —C(O)ORᵍ, —C(O)SRᵍ, —C(O)NRᵍRᵍ, —C(O)N(Rʰ)NRᵍRᵍ, —C(O)N(Rʰ)ORᵍ, —C(NRʰ)NRᵍRᵍ, —C(NOH)Rᵍ, —C(NOH)NRᵍRᵍ, —OC(O)Rᵍ, —OC(O)ORᵍ, —OC(O)SRᵍ, —OC(O)NRᵍRᵍ, —OC(NRᵉ)NRᵍRᵍ, —SC(O)Rᵍ, —SC(O)ORᵍ, —SC(O)NRᵍRᵍ, —SC(NRᵉ)NRᵍRᵍ, —N(Rʰ)C(O)Rᵍ, —N[C(O)Rᵍ]₂, —N(ORʰ)C(O)Rᵍ, —N(Rʰ)C(NRʰ)Rᵍ, —N(Rʰ)N(Rʰ)C(O)Rᵍ, —N[C(O)Rᵍ]NRᵍRᵍ, —N(Rʰ)C(S)Rᵍ, —N(Rʰ)S(O)Rᵍ, —N(Rʰ)S(O)ORᵍ, —N(Rʰ)S(O)₂Rᵍ, —N[S(O)₂Rᵍ]₂, —N(Rʰ)S(O)₂ORᵍ, —N(Rʰ)S(O)₂NRᵍRᵍ, —N(Rʰ) [S(O)₂]₂Rᵍ, —N(Rʰ)C(O)ORᵍ, —N(Rʰ)C(O)SRᵍ, —N(Rʰ)C(O)NRᵍRᵍ, —N(Rʰ)C(O)NRʰNRᵍRᵍ, —N(Rʰ)N(Rʰ)C(O)NRᵍRᵍ, —N(Rʰ)C(S)NRᵍRᵍ, —[N(Rʰ)C(O)]₂Rᵍ, —N(Rʰ) [C(O)]₂Rᵍ, —N{[C(O)]₂Rᵍ}₂, —N(Rʰ)[C(O)]₂ORᵍ, —N(Rʰ)[C(O)]₂NRᵍRᵍ, —N{[C(O)]₂ORᵍ}₂, —N{[C(O)]₂NRᵍRᵍ}₂, —[N(Rʰ)C(O)]₂ ORᵍ, —N(Rʰ)C(NRʰ)ORᵍ, —N(Rʰ)C(NOH)Rᵍ, —N(Rʰ)C(NRʰ)SRᵍ and —N(Rʰ)C(NRʰ)NRᵍRᵍ, each Rᵍ independently of one another denotes hydrogen or a group optionally substituted by one or more identical or different Rʰ, selected from among C₁₋₆alkyl, 2-6 membered heteroalkyl, C₁₋₆haloalkyl, C₃₋₁₀cycloalkyl, C₄₋₁₆cycloalkylalkyl, C₆₋₁₀aryl, C₇₋₁₆arylalkyl, 5-12 membered heteroaryl, 6-18 membered heteroarylalkyl, 3-14 membered heterocycloalkyl and 4-14 membered heterocycloalkylalkyl, each Rʰ independently of one another is selected from among hydrogen, C₁₋₆alkyl, 2-6 membered heteroalkyl, C₁₋₆haloalkyl, C₃₋₁₀cycloalkyl, C₄₋₁₆cycloalkylalkyl, C₆₋₁₀aryl, C₇₋₁₆arylalkyl, 5-12 membered heteroaryl, 6-18 membered heteroarylalkyl, 3-14 membered heterocycloalkyl and 4-14 membered heterocycloalkylalkyl, optionally in the form of the tautomers, the racemates, the enantiomers, the diastereomers and the mixtures thereof, and optionally the pharmacologically acceptable salts thereof, with the provisos that (a) if Q has the partial structure (i), X¹ or X² denotes =C(R⁴ᵃ)—, M¹ and M² denote =N— and L¹ and L² denote —S—, R¹ and R² do not correspond to an identical group —NHC(O)Rᵃ, (b) if Q has the partial structure (i) or (ii), M¹ and M² denote =N— and L¹ and L² denote —S—, neither R¹ nor R² corresponds to the amino group —NH₂ and (c) the compounds 2-diethylamino-N-{6-[(2-diethylamino-acetyl)-methyl-amino]-benzo[1,2-d;5,4-d']bisthiazol-2-yl}-N-methyl-acetamide, 2-diethylamino-N-{6-[(2-diethylamino-acetyl)-ethyl-amino]-benzo[1,2-d;5,4-d']bisthiazol-2-yl}-N-ethyl-acetamide, N-{4-bromo-6-[(2-diethylamino-acetyl)-ethyl-amino]-benzo[1,2-d;5,4-d']bisthiazol-2-yl}-2-diethylamino-N-ethyl-acetamide, N-[6-(2-chloro-acetylamino)-benzo[1,2-d;5,4-d']bisthiazol-2-yl]-2-diethylamino-acetamide, 2-diethylamino-N-[6-(2-piperidin-1-yl-acetylamino)-benzo[1,2-d;5,4-d']bisthiazol-2-yl]-acetamide, 1-ethyl-3-[6-(3-ethyl-ureido)-benzo[1,2-d;5,4-d']bisthiazol-2-yl]-urea, 2-diethylamino-N-[6-(2-diethylamino-acetylamino)-benzo[1,2-d;4,5-d']bisthiazol-2-yl]-acetamide, N,N'-dimethyl-benzo[1,2-d;4,5-d']bisthiazole-2,6-diamine, N-ethyl-N'-methyl-benzo[1,2-d;4,5-d']bisthiazole-2,6-diamine, N,N,N'-trimethyl-benzo[1,2-d;4,5-d']bisthiazole-2,6-diamine, N,N,N',N'-tetramethyl-benzo[1,2-d;4,5-d']bisthiazole-2,6-diamine, N,N'-diethyl-benzo[1,2-d;4,5-d']bisthiazole-2,6-diamine,
4,8,N,N'-tetramethyl-benzo[1,2-d;4,5-d']bisthiazole-2,6-diamine,
N-(6-acetylamino-benzo[1,2-d;4,5-d']bisthiazol-2-yl)-acetamide,
N,N'-dipropyl-benzo[1,2-d;4,5-d']bisthiazole-2,6-diamine
N,N'-diisopropyl-benzo[1,2-d;4,5-d']bisthiazole-2,6-diamine,
N,N'-bis-(2-diethylamino-ethyl)-benzo[1,2-d;4,5-d']bisthiazole-2,6-diamine, ethyl (2-methylamino-5H-imidazo[4,5-f]benzothiazol-6-yl)-carbamidate,
[6-(carboxymethyl-amino)-benzo[1,2-d;5,4-d']bisthiazol-2-ylamino]-acetic acid,
2-[6-(diethylcarbamoylmethyl-amino)-benzo[1,2-d;5,4-d']bisthiazol-2-ylamino]-N,N-diethyl-acetamide,
ethyl [6-(ethoxycarbonylmethyl-amino)-benzo[1,2-d;5,4-d']bisthiazol-2-ylamino]-acetate,
N,N'-bis-(2-diethylamino-ethyl)-benzo[1,2-d;5,4-d']bisthiazole-2,6-diamine,
N,N'-bis-(4-diethylamino-1-methyl-butyl)-benzo[1,2-d;5,4-d']bisthiazole-2,6-diamine,
N,N'-dimethyl-benzo[1,2-d;5,4-d']bisthiazole-2,6-diamine,
N,N'-diethyl-benzo[1,2-d;5,4-d']bisthiazole-2,6-diamine,
4-bromo-N,N'-diethyl-benzo[1,2-d;5,4-d']bisthiazole-2,6-diamine,
4,N,N'-trimethyl-benzo[1,2-d;5,4-d']bisthiazole-2,6-diamine,
N,N,N',N'-tetramethyl-benzo[1,2-d;5,4-d']bisthiazole-2,6-diamine,
N,N'-dipropyl-benzo[1,2-d;5,4-d']bisthiazole-2,6-diamine,
N,N'-diisopropyl-benzo[1,2-d;5,4-d']bisthiazole-2,6-diamine,
N,N,N',N'-tetraethyl-benzo[1,2-d;5,4-d']bisthiazole-2,6-diamine,
N,N'-diethyl-N,N'-dimethyl-benzo[1,2-d;5,4-d']bisthiazole-2,6-diamine,
2-chloro-N-{6-[(2-chloro-acetyl)-methyl-amino]-benzo[1,2-d;5,4-d']bisthiazol-2-yl}-N-methyl-acetamide,
2-chloro-N-{6-[(2-chloro-acetyl)-ethyl-amino]-benzo[1,2-d;5,4-d']bisthiazol-2-yl}-N-ethyl-acetamide,
N-{4-bromo-6-[(2-chloro-acetyl)-ethyl-amino]-benzo[1,2-d;5,4-d']bisthiazol-2-yl}-2-chloro-N-ethyl-acetamide and
2-chloro-N-[6-(2-chloro-acetylamino)-benzo[1,2-d;4,5-d']bisthiazol-2-yl]-acetamide
are excluded.

In one aspect the invention relates to compounds of general formulae (1A) or (1B)

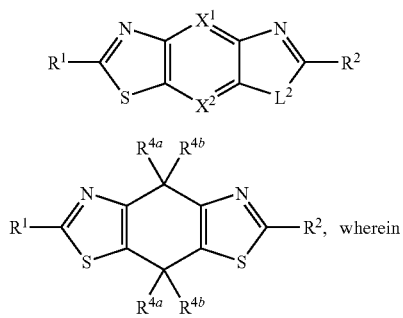

L² denotes —S— or —N(R³)— and
X¹ and X² each independently of one another denote =N— or =C(R$^{4a}$)— and
R¹, R², R³, R$^{4a}$ and R$^{4b}$ are as hereinbefore defined.

In another aspect the invention relates to compounds, wherein
each R$^{4a}$ and R$^{4b}$ is selected independently of one another from among R$^a$, —OR$^c$, —NR$^c$R$^c$, halogen, —CN, —NO$_2$, —C(O)R$^c$, —C(O)OR$^c$, —C(O)NR$^c$R$^c$ and —N(R$^g$)C(O)R$^c$ and
R$^a$, R$^c$ and R$^g$ are as hereinbefore defined.

In another aspect the invention relates to compounds of the general structure (1C)

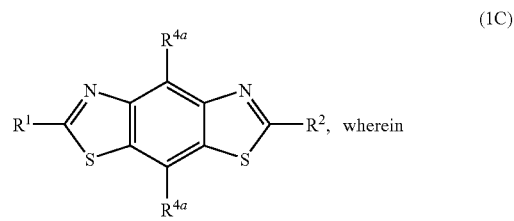

R¹ and/or R² in each case independently of one another correspond to partial structure (v),

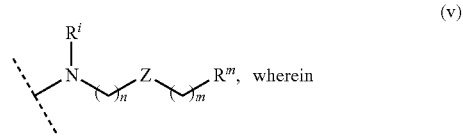

in the event that both R¹ and R² have the partial structure (v) the two partial structures may be identical or different,
Z denotes a methylene group —CH$_2$—, wherein optionally one or both hydrogen atoms may be substituted by R$^j$,
R$^i$ may be hydrogen or C$_{1-6}$alkyl,
each R$^j$ independently of one another may be selected from among C$_{1-6}$alkyl, 2-6 membered heteroalkyl, C$_{3-10}$cycloalkyl, C$_{4-16}$cycloalkylalkyl, C$_{6-10}$aryl, C$_{7-16}$arylalkyl, 6-18 membered heteroarylalkyl, 3-14 membered heterocycloalkyl and 4-14 membered heterocycloalkylalkyl, all the above-mentioned R$^j$ optionally being substituted by one or more identical or different R$^k$, selected independently of one another from among C$_{3-10}$cycloalkyl, C$_{6-10}$aryl, 5-12 membered heteroaryl, 3-14 membered heterocycloalkyl, —OR$^c$, —SR$^c$, —NR$^c$R$^c$, —ONR$^c$R$^c$, halogen, —CN, —NO$_2$, —C(O)OR$^c$, —C(O)NR$^c$R$^c$, —OC(O)R$^c$, —OC(O)OR$^c$, —N(R$^g$)C(O)R$^c$, —N(R$^g$)C(O)OR$^c$ and —N(R$^g$)C(NR$^9$)NR$^c$R$^c$,
R$^m$ denotes —C(O)NR''R'' and
R'' is selected independently of one another from among hydrogen, C$_{1-6}$alkyl, 2-6 membered heteroalkyl, C$_{1-6}$haloalkyl, C$_{3-10}$cycloalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, all the above-mentioned R'' optionally being substituted by one or more identical or different R$^o$,
R$^o$ is selected independently of one another from among C$_{3-10}$cycloalkyl, C$_{6-10}$aryl, 5-12 membered heteroaryl, 3-14 membered heterocycloalkyl, —OR$^p$, —NR$^p$R$^p$, halogen, —C(O)OR$^p$, —C(O)NR$^p$R$^p$ and C$_{1-6}$alkyl, the latter optionally being substituted by —C(O)NR$^p$R$^p$,
while R$^p$ is selected independently of one another from among hydrogen and C$_{1-6}$alkyl and all the above-mentioned R$^o$, wherever possible, may optionally be substituted by one or more identical or different halogen atom(s), or NR″R″ denotes a nitrogen-containing, 3-14 membered heterocycloalkyl or 5-12 membered heteroaryl, while one or more identical or different additional heteroatom(s) may be present, optionally substituted by one or more identical or different $R^q$, $R^q$ is selected independently of one another from among $C_{1-6}$alkyl, 2-6 membered heteroalkyl, $C_{3-10}$cycloalkyl, $C_{6-10}$aryl, $C_{7-16}$arylalkyl, 6-18 membered heteroarylalkyl, 3-14 membered heterocycloalkyl, 4-14 membered heterocycloalkyl-alkyl, =O, —OR′, —NR′R′, halogen, —S(O)$_2$R′, —C(O)R′, —C(O)OR′ and —C(O)NR′R′, while all the above-mentioned $R^q$, wherever possible, may optionally be substituted by one or more identical or different group(s), selected independently of one another from among $C_{1-6}$alkyl, $C_{6-10}$aryl, 5-12 membered heteroaryl, 3-14 membered heterocycloalkyl, —OR′, —NR′R′, halogen and —C(O)NR′R′ and R′ denotes hydrogen or $C_{1-6}$alkyl, or $R^j$ together with an R″ denotes an n-$C_{1-4}$alkylene group and the second group R″ is as hereinbefore defined and m and n each independently of one another have the value 0, 1, 2, 3, 4 or 5 and m+n is equal to 0, 1, 2, 3, 4 or 5 and the group selected from $R^1$ and $R^2$ which does not correspond to a partial structure (v), and $R^{4a}$, $R^c$ and $R^g$ are as hereinbefore defined.

In another aspect the invention relates to compounds wherein one of the groups $R^1$ or $R^2$ corresponds to the partial structure (v) defined hereinbefore and the second group $R^1$ or $R^2$ remaining in each case is selected from among —N(R$^s$)[C(O)]$_2$NR′R′, —N(R$^s$)[C(O)]$_2$R′, —N{[C(O)]$_2$R′}$_2$, —N(R$^s$S(O)$_2$R′, —N[S(O)$_2$R′]$_2$ and —N(R$^s$)C(O)R′, wherein $R^s$ denotes hydrogen or $C_{1-6}$alkyl and $R^t$ is selected independently of one another from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl and 5-12 membered heteroaryl, all the above-mentioned $R^t$ optionally being substituted by one or more identical or different $R^u$, $R^u$ is selected independently of one another from among $C_{1-6}$alkyl, $C_{6-10}$aryl, —NR′R$^v$ and halogen, while all the above-mentioned $R^u$, wherever possible, may optionally be substituted by one or more identical or different group(s), selected from among $C_{1-6}$alkyl and halogen, and $R^v$ denotes $C_{1-6}$alkyl.

In another aspect the invention relates to compounds, wherein one of the groups $R^1$ or $R^2$ corresponds to the partial structure (v) defined hereinbefore and the second group $R^1$ or $R^2$ remaining in each case corresponds to —NR$^s$R$^s$, wherein $R^s$ is selected independently of one another from among hydrogen, $C_{1-6}$alkyl, 2-6 membered heteroalkyl, $C_{1-6}$haloalkyl, $C_{6-10}$aryl, $C_{7-16}$arylalkyl, 6-18 membered heteroarylalkyl and 4-14 membered heterocycloalkyl-alkyl, all the above-mentioned $R^s$ optionally being substituted by one or more identical or different $R^t$, $R^t$ is selected from among $C_{1-6}$alkyl, $C_{1-6}$haloalkyl, $C_{6-10}$aryl, 5-12 membered heteroaryl, 3-14 membered heterocycloalkyl, =O, —OH, —NR″R″ and halogen, while all the above-mentioned $R^t$, wherever possible, may optionally be substituted by one or more identical or different group(s), selected from among $C_{1-6}$alkyl, =O and halogen, and $R^u$ independently of one another denotes hydrogen or $C_{6-10}$aryl.

In another aspect the invention relates to compounds wherein both $R^1$ and $R^2$ independently of one another correspond to the partial structure (v) defined hereinbefore and $R^1$ and $R^2$ may be identical or different.

In another aspect the invention relates to compounds of the general structure (1C)

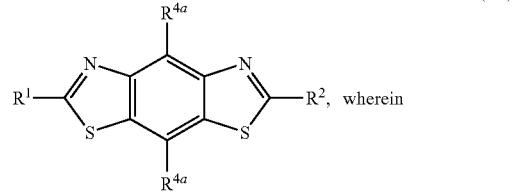

$R^1$ and $R^2$ independently of one another are selected from among —NR$^a$R$^a$, —N(OR$^a$)R$^a$, —N(R$^g$)NR$^a$R$^a$, —N(R$^g$)S(O)R$^a$, —N(R$^g$)S(O)$_2$R$^a$, —N[S(O)$_2$R$^a$]$_2$, —N(R$^g$)S(O)$_2$OR$^a$, —N(R$^g$)S(O)$_2$NR$^a$R$^a$, —N(R$^g$)S(O)OR$^a$, —N[C(O)R$^a$]$_2$, —N(R$^g$)C(S)R$^a$, —N[C(O)R$^a$]NR$^a$R$^a$, —N(R$^g$)N(R$^g$)C(O)R$^a$, —N(OR$^g$)C(O)R$^a$, —N(R$^g$)C(NOH)R$^a$, —N(R$^g$)C(NR$^g$)R$^a$, —N(R$^g$)C(O)OR$^a$, —N(R$^g$)C(O)SR$^a$, —N(R$^g$)C(O)NR$^a$R$^a$, —N(R$^g$)C(S)NR$^a$R$^a$, —N(R$^g$)C(O)NR$^g$NR$^a$R$^a$, —N(R$^g$)N(R$^g$)C(O)NR$^a$R$^a$, —N(R$^g$)C(NR$^g$)OR$^a$, —N(R$^g$)C(NR$^g$)SR$^a$, —N(R$^g$)C(NR$^g$)NR$^a$R$^a$, —[N(R$^g$)C(O)]$_2$R$^a$, —N(R$^g$)[C(O)]$_2$R$^a$, —N{[C(O)]$_2$R$^a$}$_2$, —N(R$^g$)[C(O)]$_2$OR$^a$, —N(R$^g$)[C(O)]$_2$NR$^a$R$^a$, —N{[C(O)]$_2$OR$^a$}$_2$, —N{[C(O)]$_2$NR$^a$R$^a$}$_2$, —[N(R$^g$)C(O)]$_2$OR$^a$ and a nitrogen-containing 3-8 membered heterocycloalkyl attached via a cyclic nitrogen, this heterocycloalkyl optionally being substituted by one or more identical or different group(s) selected from among $R^a$ and $R^b$, each $R^{4a}$ is selected independently of one another from among $R^a$ and $R^b$, optionally in the form of the tautomers, the racemates, the enantiomers, the diastereomers and the mixtures thereof, and optionally the pharmacologically acceptable salts thereof, with the provisos that (a) neither $R^1$ nor $R^2$ corresponds to the amino group —NH$_2$, (b) one of the two $R^{4a}$ groups does not correspond to hydrogen and (c) the compounds 4-bromo-N,N'-diethyl-benzo[1,2-d;5,4-d']bisthiazole-2,6-diamine and 4,N,N'-trimethyl-benzo[1,2-d;5,4-d']bisthiazole-2,6-diamine are excluded and $R^a$, $R^b$ and $R^g$ are as hereinbefore defined.

In another aspect the invention relates to compounds of general formula (2)

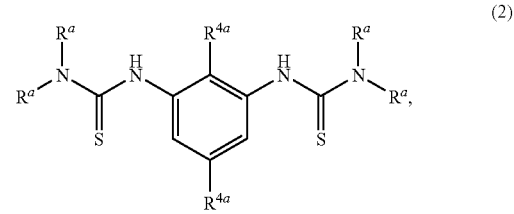

which are suitable as intermediate products for preparing compounds of general formula (1), wherein NR$^a$R$^a$ of formula (2) does not correspond to the amino group —NH$_2$, at least one $R^{4a}$ of formula (2) is not hydrogen and $R^{4a}$ and $R^a$ otherwise have the definitions given for formula (1), which are also an object of the invention.

In another aspect the invention relates to compounds—or the pharmacologically acceptable salts thereof—of general formulae (1), (1A), (1B) and (1C) as pharmaceutical compositions.

In another aspect the invention relates to pharmaceutical preparations, containing as active substance one or more compounds of general formulae (1), (1A), (1B) and (1C) or the pharmacologically acceptable salts thereof, optionally in combination with conventional excipients and/or carriers.

In another aspect the invention relates to the use of compounds of general formula (1)

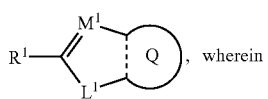

(1)

, wherein

Q has a partial structure selected from among the partial structures (i)-(iv)

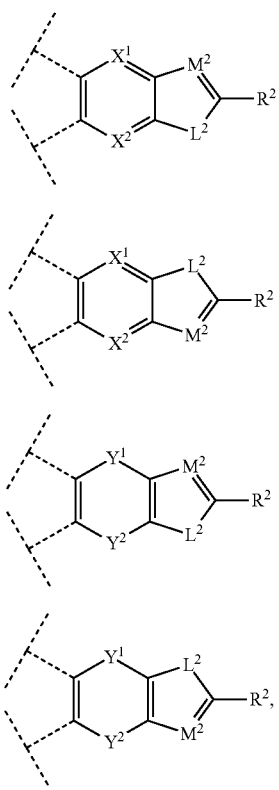

$L^1$ and $L^2$ each independently of one another denote —O—, —S—, —SO— or —N($R^3$)—,
$M^1$ and $M^2$ each independently of one another denote =N— or =C($R^3$)—,
$X^1$ and $X^2$ each independently of one another denote =N— or =C($R^{4a}$)— and
$Y^1$ and $Y^2$ each independently of one another denote —O—, —S—, —SO—, —SO$_2$—, —C($R^{4a}$)($R^{4b}$)— or —N($R^{4a}$)—,
$R^1$ and $R^2$ independently of one another are selected from among —NR$^a$R$^a$, —N(OR$^a$)R$^a$, —N(R$^g$)NR$^a$R$^a$, —N(R$^g$)S(O)R$^a$, —N(R$^g$)S(O)$_2$R$^a$, —N[S(O)$_2$R$^a$]$_2$, —N(R$^g$)S(O)$_2$OR$^a$, —N(R$^g$)S(O)$_2$NR$^a$R$^a$, —N(R$^g$)S(O)OR$^a$, —N(R$^g$)C(O)R$^a$, —N[C(O)R$^a$]$_2$, —N(R$^g$)C(S)R$^a$, —N[C(O)R$^a$]NR$^a$R$^a$, —N(R$^g$)N(R$^g$)C(O)R$^a$, —N(OR)C(O)R$^a$, —N(R$^g$)C(NOH)R$^a$, —N(R$^g$)C(NR$^g$)R$^a$, —N(R$^g$)C(O)OR$^a$, —N(R$^g$)C(O)SR$^a$, —N(R$^g$)C(O)NR$^a$R$^a$, —N(R$^g$)C(S)NR$^a$R$^a$, —N(R$^g$)C(O)NR$^g$NR$^a$R$^a$, —N(R$^g$)N(R$^g$)C(O) NR$^a$R$^a$, —N(R$^g$)C(NR$^g$)OR$^a$, —N(R$^g$)C(NR$^g$)SR$^a$, —N(R$^g$)C(NR$^g$)NR$^a$R$^a$, —[N(R$^g$)C(O)]$_2$R$^a$, —N(R$^g$)[C(O)]$_2$R$^a$, —N{[C(O)]$_2$R$^a$}$_2$, —N(R$^g$)[C(O)]$_2$OR$^a$, —N(R$^g$)[C(O)]$_2$NR$^a$R$^a$, —N{[C(O)]$_2$OR$^a$}$_2$, —N{[C(O)]$_2$NR$^a$R$^a$}$_2$, —[N(R$^g$)C(O)]$_2$OR$^a$ and a nitrogen-containing 3-8 membered heterocycloalkyl attached via a cyclic nitrogen, this heterocycloalkyl optionally being substituted by one or more identical or different group(s) selected from among R$^a$ and R$^b$
each R$^3$, R$^{4a}$ and R$^{4b}$ is selected independently of one another from among R$^a$ and R$^b$,
each R$^a$ independently of one another denotes hydrogen or a group optionally substituted by one or more identical or different R$^b$ and/or R$^c$, selected from among C$_{1-6}$alkyl, 2-6 membered heteroalkyl, C$_{1-6}$haloalkyl, C$_{3-10}$cycloalkyl, C$_{4-6}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl,
each R$^b$ denotes a suitable group and is selected in each case independently of one another from among =O, —OR$^c$, C$_{1-3}$haloalkyloxy, —OCF$_3$, =S, —SR$^c$, =NR$^c$, =NOR$^c$, =NNR$^c$R$^c$, =NN(R$^g$)C(O)NR$^c$R$^c$, —NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O)R$^c$, —S(O)OR$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)NR$^c$R$^c$, —OS(O)$_2$NR$^c$R$^c$, —C(O)R$^c$, —C(O)OR$^c$, —C(O)SR$^c$, —C(O)NR$^c$R$^c$, —C(O)N(R$^g$)NR$^c$R$^c$, —C(O)N(R$^g$)OR$^c$, —C(NR$^g$)NR$^c$R$^c$, —C(NOH)R$^c$, —C(NOH)NR$^c$R$^c$, —OC(O)R$^c$, —OC(O)OR$^c$, —OC(O)SR$^c$, —OC(O)NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O) R$^c$, —N[C(O)R$^c$]NR$^c$R$^c$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$) [S(O)$_2$]$_2$ R$^c$, —N(R$^g$)C(O)OR$^c$, —N(R$^g$)C(O)SR$^c$, —N(R$^g$)C(O)NR$^c$R$^c$, —N(R$^g$)C(O)NR$^g$NR$^c$R$^c$, —N(R$^g$)N(R$^g$)C(O)NR$^c$ R$^c$, —N(R$^g$)C(S)NR$^c$R$^c$, —[N(R$^g$)C(O)]$_2$R$^c$, —N(R$^g$)[C(O)]$_2$ R$^c$, —N{[C(O)]$_2$R$^c$}$_2$, —N(R$^g$)[C(O)]$_2$OR$^c$, —N(R$^g$)[C (O)]$_2$ NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C (NOH)R$^c$, —N(R$^g$)C(NR$^g$)SR$^c$ and —N(R$^g$)C(NR$^g$)NR$^c$R$^c$,
each R$^c$ independently of one another denotes hydrogen or a group optionally substituted by one or more identical or different R$^d$ and/or R$^e$, selected from among C$_{1-6}$alkyl, 2-6 membered heteroalkyl, C$_{1-6}$haloalkyl, C$_{3-10}$cycloalkyl, C$_{4-6}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl,
each R$^d$ denotes a suitable group and is selected in each case independently of one another from among =O, —OR$^e$, C$_{1-3}$haloalkyloxy, —OCF$_3$, =S, —SR$^e$, =NR$^e$, =NOR$^e$, =NNR$^e$R$^e$, =NN(R$^g$)C(O)NR$^e$R$^e$, —NR$^e$R$^e$, —ONR$^e$R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$, —N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$ R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$ NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$ and —N(R$^g$)C(NR$^g$)NR$^e$R$^e$, each R$^e$ independently of one another denotes hydrogen or a group optionally substituted by one or more identical or different R$^f$ and/or R$^g$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, each R$^f$ denotes a suitable group and is selected in each case independently of one another from among =O, —OR$^g$, C$_{1-3}$haloalkyloxy, —OCF$_3$, =S, —SR$^g$, =NR$^g$, =NOR$^g$, =NNR$^g$R$^g$, =NN(R$^h$)C(O)NR$^g$R$^g$, —NR$^g$R$^g$, —ONR$^g$R$^g$, —N(R$^h$)NR$^g$R$^g$, halogen, —CF$_3$, —CN, —NC, —OCN, —SCN, —NO, —NO$_2$, =N$_2$, —N$_3$, —S(O)R$^g$, —S(O)OR$^g$, —S(O)$_2$R$^g$, —S(O)$_2$OR$^g$, —S(O)NR$^g$R$^g$, —S(O)$_2$NR$^g$R$^g$, —OS(O)R$^g$, —OS(O)$_2$R$^g$, —OS(O)$_2$OR$^g$, —OS(O)NR$^g$R$^g$, —OS(O)$_2$NR$^g$R$^g$, —C(O)R$^g$, —C(O)OR$^g$, —C(O)SR$^g$, —C(O)NR$^g$R$^g$, —C(O)N(R$^h$)NR$^g$R$^g$, —C(O)N(R$^h$)OR$^g$, —C(NR$^h$)NR$^g$R$^g$, —C(NOH)R$^g$, —C(NOH)NR$^g$R$^g$, —OC(O)R$^g$, —OC(O)OR$^g$, —OC(O)SR$^g$, —OC(O)NR$^g$R$^g$, —OC(NR$^e$)NR$^g$R$^g$, —SC(O)R$^g$, —SC(O)OR$^g$, —SC(O)NR$^g$R$^g$, —SC(NR$^e$)NR$^g$R$^g$, —N(R$^h$)C(O)R$^g$, —N[C(O)R$^g$]$_2$, —N(OR$^h$)C(O)R$^g$, —N(R$^h$)C(NR$^h$)R$^g$, —N(R$^h$)N(R$^h$)C(O)R$^g$, —N[C(O)R$^g$]NR$^g$R$^g$, —N(R$^h$)C(S)R$^g$, —N(R$^h$)S(O)R$^g$, —N(R$^h$)S(O)OR$^g$, —N(R$^h$)S(O)$_2$R$^g$, —N[S(O)$_2$R$^g$]$_2$, —N(R$^h$)S(O)$_2$OR$^g$, —N(R$^h$)S(O)$_2$NR$^g$R$^g$, —N(R$^h$)[S(O)$_2$]$_2$R$^g$, —N(R$^h$)C(O)OR$^g$, —N(R$^h$)C(O)SR$^g$, —N(R$^h$)C(O)NR$^g$R$^g$, —N(R$^h$)C(O)NR$^h$NR$^g$R$^g$, —N(R$^h$)N(R$^h$)C(O)NR$^g$ R$^g$, —N(R$^h$)C(S)NR$^g$R$^g$, —[N(R$^h$)C(O)]$_2$R$^g$, —N(R$^h$) [C(O)]$_2$R$^g$, —N{[C(O)]$_2$R$^g$}$_2$, —N(R$^h$)[C(O)]$_2$OR$^g$, —N(R$^h$)[C(O)]$_2$ NR$^g$R$^g$, —N{[C(O)]$_2$OR$^g$}$_2$, —N{[C(O)]$_2$NR$^g$R$^g$}$_2$, —[N(R$^h$)C(O)]$_2$OR$^g$, —N(R$^h$)C(NR$^h$)OR$^g$, —N(R$^h$)C(NOH)R$^g$, —N(R$^h$)C(NR$^h$)SR$^g$ and —N(R$^h$)C(NR$^h$)NR$^g$R$^g$, each R$^g$ independently of one another denotes hydrogen or a group optionally substituted by one or more identical or different R$^h$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl,
each R$^h$ is selected independently of one another from among hydrogen, C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl,
optionally in the form of the tautomers, the racemates, the enantiomers, the diastereomers and the mixtures thereof, and optionally the pharmacologically acceptable salts thereof,
for preparing a pharmaceutical composition for the treatment and/or prevention of cancer.

In another aspect the invention relates to the use of compounds of general formulae (1), (1A), (1B) or (1C) for preparing a pharmaceutical composition for the treatment and/or prevention of cancer, infections, inflammations and autoimmune diseases.

In another aspect the invention relates to a pharmaceutical preparation comprising a compound of general formulae (1), (1A), (1B) or (1C) and at least one other cytostatic or cytotoxic active substance, different from formula (1), (1A), (1B) or (1C), optionally in the form of the tautomers, the racemates, the enantiomers, the diastereomers and the mixtures thereof and optionally the pharmacologically acceptable salts thereof (A) Aspects relating to R$^1$:
(A1) In one aspect the invention relates to compounds of general formula (1C), wherein R$^1$ is selected from among —NHS(O)$_2$R$^a$, —N[S(O)$_2$R$^a$]$_2$, —NHC(O)R$^a$, —NH[C(O)]$_2$R$^a$, —NH[C(O)]$_2$OR$^a$, —NH[C(O)]$_2$NR$^a$R$^a$, —N{[C(O)]$_2$NR$^a$R$^a$}$_2$.
(A2) In another aspect the invention relates to compounds of general formula (1C), wherein R$^1$ corresponds to a nitrogen-containing 3-8 membered heterocycloalkyl attached via a cyclic nitrogen, optionally substituted by one or more identical or different group(s) selected from among R$^a$ and R$^b$.
(A3) In another aspect the invention relates to compounds of general formula (1C), wherein R$^1$ corresponds to —NR$^a$R$^a$.
(A4) In another aspect the invention relates to compounds of general formula (1C), wherein R$^1$ is selected from among —NHCH$_2$C(O)R$^c$, —NHCH$_2$C(O)OR$^c$ and —NHCH$_2$C(O)NR$^c$R$^c$ and a hydrogen of the methylene group in the above groups may optionally be substituted by R$^j$.

(B) Aspects relating to R$^2$:
(B1) In one aspect the invention relates to compounds of general formula (1C), wherein R$^2$ is selected from among —NHS(O)$_2$R$^a$, —N[S(O)$_2$R$^a$]$_2$, —NHC(O)R$^a$, —NH[C(O)]$_2$R$^a$, —NH[C(O)]$_2$OR$^a$, —NH[C(O)]$_2$NR$^a$R$^a$, —N{[C(O)]$_2$NR$^a$R$^a$}$_2$.
(B2) In another aspect the invention relates to compounds of general formula (1C), wherein R$^2$ corresponds to a nitrogen-containing 3-8 membered heterocycloalkyl attached via a cyclic nitrogen, optionally substituted by one or more identical or different group(s) selected from among R$^a$ and R$^b$.
(B3) In another aspect the invention relates to compounds of general formula (1C), wherein R$^2$ corresponds to a group —NR$^a$R$^a$.
(B4) In another aspect the invention relates to compounds of general formula (1C), wherein R$^2$ is selected from among —NHCH$_2$C(O)R$^c$, —NHCH$_2$C(O)OR$^c$ and —NHCH$_2$C(O)NR$^c$R$^c$ and a hydrogen of the methylene group in the above groups may optionally be substituted by R$^j$.

(C) Aspects relating to R$^{4a}$:
(C1) In one aspect the invention relates to compounds of general formula (1C), wherein R$^{4a}$ is selected from among hydrogen, halogen, alkyl and haloalkyl.
(C2) In another aspect the invention relates to compounds of general formula (1C), wherein R$^{4a}$ is selected from among hydrogen, methyl, trifluoromethyl, branched alkyl, bromine, chlorine, fluorine, amino, dimethylamino, hydroxy, methoxy and alkylcarboxylate.
(C3) In another aspect the invention relates to compounds of general formula (1C) wherein one group R$^{4a}$ corresponds to hydrogen and the second group R$^4$ corresponds to an alkyl or haloalkyl.

The following Table shows preferred combinations of various aspects of the compounds of formula (1C) according to the invention:

| embodiment | R$^1$ | R$^2$ | R$^{4a}$ |
|---|---|---|---|
| I-1 | A1 | B3 | C1 |
| I-2 | A1 | B4 | C1 |
| I-3 | A2 | B3 | C1 |
| I-4 | A2 | B4 | C1 |
| I-5 | A3 | B3 | C1 |
| I-6 | A3 | B4 | C1 |
| I-7 | A4 | B1 | C1 |
| I-8 | A4 | B1 | C2 |
| I-9 | A4 | B1 | C3 |
| I-10 | A4 | B2 | C1 |
| I-11 | A4 | B2 | C2 |
| I-12 | A4 | B2 | C3 |
| I-13 | A4 | B3 | C1 |
| I-14 | A4 | B3 | C2 |
| I-15 | A4 | B3 | C3 |
| I-16 | A4 | B4 | C1 |
| I-17 | A4 | B4 | C2 |
| I-18 | A4 | B4 | C3 |

DEFINITIONS

As used herein, the following definitions apply, unless stated otherwise:

The use of the prefix $C_{x-y}$, wherein x and y each represent a natural number (x<y), indicates that the chain or ring structure or combination of chain and ring structure thus designated and mentioned in direct connection may consist of a total of not more than y and not less than x carbon atoms.

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl at least one triple bond. If a hydrocarbon chain should have both at least one double bond and at least one triple bond, by definition it belongs to the alkynyl sub-group. All the above-mentioned sub-groups may be further subdivided into straight-chain (unbranched) and branched. If an alkyl is substituted, it may be mono- or polysubstituted independently of one another at all the hydrogen-carrying carbon atoms.

Examples of individual sub-groups are listed below.
Straight-Chain (Unbranched) or Branched Saturated Hydrocarbon Chains:

methyl; ethyl; n-propyl; isopropyl (1-methylethyl); n-butyl; 1-methylpropyl; isobutyl (2-methylpropyl); sec.-butyl (1-methylpropyl); tert.-butyl (1,1-dimethylethyl); n-pentyl; 1-methylbutyl; 1-ethylpropyl; isopentyl (3-methylbutyl); neopentyl (2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl; 2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.
Straight-Chained (Unbranched) or Branched Alkenyl:

vinyl (ethenyl); prop-1-enyl; allyl (prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methyl-prop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1,3-dienyl; hexa-1,4-dienyl; penta-1,4-dienyl; penta-1,3-dienyl; buta-1,3-dienyl; 2,3-dimethylbuta-1,3-diene etc.
Straight-Chain (Unbranched) or Branched Alkynyl:

ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. unless otherwise stated are meant saturated hydrocarbon groups with the corresponding number of carbon atoms, including all the isomeric forms.

By the terms propenyl, butenyl, pentenyl, hexenyl, heptenyl, octenyl, nonenyl, decenyl etc. unless otherwise stated are meant unsaturated hydrocarbon groups with the corresponding number of carbon atoms and a double bond, including all the isomeric forms, also (Z)/(E)-isomers, where applicable.

By the terms butadienyl, pentadienyl, hexadienyl, heptadienyl, octadienyl, nonadienyl, decadienyl etc. unless otherwise stated are meant unsaturated hydrocarbon groups with the corresponding number of carbon atoms and two double bonds, including all the isomeric forms, also (Z)/(E)-isomers, where applicable.

By the terms propynyl, butynyl, pentynyl, hexynyl, heptynyl, octynyl, nonynyl, decynyl etc. unless otherwise stated are meant unsaturated hydrocarbon groups with the corresponding number of carbon atoms and a triple bond, including all the isomeric forms.

By the term heteroalkyl are meant groups which are derived from the alkyl as hereinbefore defined in its widest sense by replacing, in the hydrocarbon chains, one or more of the groups —$CH_3$ independently of one another by the groups —OH, —SH or —$NH_2$, one or more of the groups —$CH_2$— independently of one another by the groups —O—, —S— or —NH—, one or more of the groups

by the group

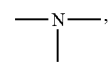

one or more of the groups =CH— by the group =N—, one or more of the groups =$CH_2$ by the group =NH or one or more of the groups =CH by the group =N, while a total of not more than three heteroatoms may be present in one heteroalkyl, there must be at least one carbon atom between two oxygen atoms and between two sulphur atoms or between one oxygen and one sulphur atom and the group as a whole must have chemical stability.

A direct result of the indirect definition/derivation from alkyl is that heteroalkyl is made up of the sub-groups saturated hydrocarbon chains with heteroatom(s), heteroalkenyl and heteroalkynyl, and it may be further subdivided into straight-chain (unbranched) and branched. If a heteroalkyl is substituted, it may be mono- or polysubstituted independently of one another at all the hydrogen-carrying oxygen, sulphur, nitrogen and/or carbon atoms. Heteroalkyl itself as a substituent may be attached to the molecule both through a carbon atom and through a heteroatom.

The following are listed by way of example:
dimethylaminomethyl; dimethylaminoethyl (1-dimethylaminoethyl; 2-dimethyl-aminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethylamino]-methyl; 3-[2-(dimethylamino-ethyl)-ethyl-amino]-propyl; hydroxymethyl; 2-hydroxy-ethyl; 3-hydroxypropyl; methoxy; ethoxy; propoxy; methoxymethyl; 2-methoxyethyl etc.

Haloalkyl is derived from alkyl as hereinbefore defined in its broadest sense, by replacing one or more hydrogen atoms of the hydrocarbon chain independently of one another by halogen atoms, which may be identical or different. A direct result of the indirect definition/derivation from alkyl is that haloalkyl is made up of the sub-groups saturated hydrohalogen chains, haloalkenyl and haloalkynyl, and it may be further subdivided into straight-chain (unbranched) and branched. If a haloalkyl is substituted, it may be mono- or polysubstituted independently of one another at all the hydrogen-carrying carbon atoms.

The following are listed by way of example:
—$CF_3$; —$CHF_2$; —$CH_2F$; —$CF_2CF_3$; —$CHFCF_3$; —$CH_2CF_3$; —$CF_2CH_3$; —$CHFCH_3$; —$CF_2CF_2CF_3$; —$CF_2CH_2CH_3$; —CF=$CF_2$; —CCl=$CH_2$; —CBr=$CH_2$; —CI=$CH_2$; —C≡C—$CF_3$; —$CHFCH_2CH_3$; —$CHFCH_2CF_3$ etc.

Halogen relates to fluorine, chlorine, bromine and/or iodine atoms.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). By unsaturated is meant that there is at least one double bond in the ring system, but no aromatic system is formed. In bicyclic hydrocarbon rings two rings are linked such that they share at least two carbon atoms. In spirohydrocarbon rings one carbon atom (spiroatom) is shared by two rings. If a cycloalkyl is substituted, it may be mono- or polysubstituted independently of one another at all the hydrogen-carrying carbon atoms. Cycloalkyl itself as a substituent may be attached to the molecule through any suitable position of the ring system.

The following individual sub-groups are listed by way of example:
Monocyclic Hydrocarbon Rings Saturated:
cyclopropyl; cyclobutyl; cyclopentyl; cyclohexyl; cycloheptyl etc.
Monocyclic Hydrocarbon Rings Unsaturated:
cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.
Bicyclic Hydrocarbon Rings (Saturated and Unsaturated):
bicyclo[2.2.0]hexyl; bicyclo[3.2.0]heptyl; bicyclo[3.2.1]octyl; bicyclo[2.2.2]octyl; bicyclo[4.3.0]nonyl (octahydroindenyl); bicyclo[4.4.0]decyl (decahydronaphthalene); bicyclo[2.2.1]heptyl (norbornyl); (bicyclo[2.2.1]hepta-2,5-dienyl (norborna-2,5-dienyl); bicyclo[2.2.1]hept-2-enyl (norbornenyl); bicyclo[4.1.0]heptyl (norcaranyl); bicyclo-[3.1.1]heptyl (pinanyl) etc.
Spirohydrocarbon Rings (Saturated and Unsaturated):
spiro[2.5]octyl, spiro[3.3]heptyl, spiro[4.5]dec-2-enyl etc.

Cycloalkylalkyl denotes the combination of the alkyl and cycloalkyl groups defined hereinbefore, in each case in their broadest sense. The alkyl group as substituent is directly linked to the molecule and is in turn substituted by a cycloalkyl group. The linking of alkyl and cycloalkyl in both groups may be effected by means of any suitable carbon atoms. The sub-groups of alkyl and cycloalkyl are also included in the combination of the two groups.

Aryl denotes mono-, bi- or tricyclic carbon rings with at least one aromatic ring. If an aryl is substituted, the substitution may be mono- or polysubstitution in each case, at all the hydrogen-carrying carbon atoms, independently of one another. Aryl itself may be linked to the molecule as substituent via any suitable position of the ring system.

Typical examples are listed below:
phenyl; naphthyl; indanyl (2,3-dihydroindenyl); 1,2,3,4-tetrahydronaphthyl; fluorenyl etc.

Arylalkyl denotes the combination of the groups alkyl and aryl as hereinbefore defined, in each case in their broadest sense. The alkyl group as substituent is directly linked to the molecule and is in turn substituted by an aryl group. The alkyl and aryl may be linked in both groups via any carbon atoms suitable for this purpose. The respective sub-groups of alkyl and aryl are also included in the combination of the two groups.

Typical examples are listed below:
benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. If a heteroaryl is substituted, the substitution may be mono- or polysubstitution in each case, at all the hydrogen-carrying carbon and/or nitrogen atoms, independently of one another. Heteroaryl itself as substituent may be linked to the molecule via any suitable position of the ring system, both carbon and nitrogen.

Typical examples are listed below:
Monocyclic Heteroaryls:
furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.
Polycyclic Heteroaryls:
indolyl; isoindolyl; benzofuryl; benzothienyl; benzoxazolyl; benzothiazolyl; benzisoxazolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetrahydrothienyl; isobenzothienyl; benzoxazolyl; pyridopyridyl; benzotetrahydrofuryl; benzotetrahydro-thienyl; purinyl; benzodioxolyl; phenoxazinyl; phenothiazinyl; pteridinyl; benzothiazolyl; imidazopyridyl;

imidazothiazolyl; dihydrobenzisoxazinyl; benzisoxazinyl; benzoxazinyl; dihydrobenzisothiazinyl; benzopyranyl; benzothiopyranyl; cumarinyl; isocumarinyl; chromonyl; chromanonyl; tetrahydroquinolinyl; dihydroquinolinyl; dihydroquinolinonyl; dihydroisoquinolinonyl; dihydrocumarinyl; dihydroisocumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzo-thiopyranyl-5-oxide and benzothiopyranyl-S,S-dioxide etc.

Heteroarylalkyl denotes the combination of the alkyl and heteroaryl groups defined hereinbefore, in each case in their broadest sense. The alkyl group as substituent is directly linked to the molecule and is in turn substituted by a heteroaryl group. The linking of the alkyl and heteroaryl may be achieved on the alkyl side via any carbon atoms suitable for this purpose and on the heteroaryl side by any carbon or nitrogen atoms suitable for this purpose. The respective sub-groups of alkyl and heteroaryl are also included in the combination of the two groups.

By the term heterocycloalkyl are meant groups which are derived from the cycloalkyl as hereinbefore defined if in the hydrocarbon rings one or more of the groups —CH$_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —SO$_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

Typical examples of individual sub-groups are listed below:

Monocyclic Heterorings (Saturated and Unsaturated):

tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-5-oxide; thiomorpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydro-pyrimidinyl; dihydrofuryl; dihydropyranyl; tetrahydrothienyl-5-oxide; tetrahydrothienyl-S,S-dioxide; homothiomorpholinyl-5-oxide; 2,3-dihydroazet; 2H-pyrrolyl; 4H-pyranyl; 1,4-dihydropyridinyl etc.

Bicyclic Heterorings (Saturated and Unsaturated):

8-azabicyclo[3.2.1]octyl; 8-azabicyclo[5.1.0]octyl; 2-oxa-5-azabicyclo[2.2.1]heptyl; 8-oxa-3-aza-bicyclo[3.2.1]octyl; 3.8-diaza-bicyclo[3.2.1]octyl; 2.5-diaza-bicyclo-[2.2.1]heptyl; 1-aza-bicyclo[2.2.2]octyl; 3.8-diaza-bicyclo[3.2.1]octyl; 3.9-diaza-bicyclo[4.2.1]nonyl; 2.6-diaza-bicyclo[3.2.2]nonyl etc.

Spiro-Heterorings (Saturated and Unsaturated):

1,4-dioxa-spiro[4.5]decyl; 1-oxa-3.8-diaza-spiro[4.5]decyl; and 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl etc.

Heterocycloalkylalkyl denotes the combination of the alkyl and heterocycloalkyl groups defined hereinbefore, in each case in their broadest sense. The alkyl group as substituent is directly linked to the molecule and is in turn substituted by a heterocycloalkyl group. The linking of the alkyl and heterocycloalkyl may be achieved on the alkyl side via any carbon atoms suitable for this purpose and on the heterocycloalkyl side by any carbon or nitrogen atoms suitable for this purpose. The respective sub-groups of alkyl and heterocycloalkyl are also included in the combination of the two groups.

The term "substituted" indicates that a hydrogen atom which is bound directly to the atom in question is replaced by another atom or another group of atoms. Bivalent substituents such as for example =O, =S, =NR, =NOR, =NNRR, =NN(R)C(O)NRR, =N$_2$ or the like can only be substituents at carbon atoms. They require exchanging for two geminal hydrogen atoms, i.e. hydrogen atoms which are bound to the same carbon atom saturated before the substitution. Substitution by a bivalent substituent is therefore only possible at the groups —CH$_3$ and —CH$_2$—, not at the groups

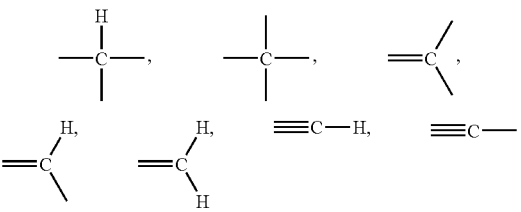

and not at aromatic carbon atoms.

Additionally, by the term "suitable substituent/suitable group" is meant a substituent which on the one hand is suitable on account of its valency and on the other hand leads to a system with chemical stability.

LIST OF ABBREVIATIONS

| | |
|---|---|
| Ac | acetyl |
| ACN | acetonitrile |
| Boc | tert.-butyloxycarbonyl |
| Bu | butyl |
| c | concentration |
| chex | cyclohexane |
| DC, TLC | thin layer chromatography |

-continued

| | |
|---|---|
| DCM | dichloromethane |
| DIC | diisopropylcarbodiimide |
| DIPEA | N-ethyl-N,N-diisopropylamine (Hünig base) |
| DMA | N,N-dimethylacetamide |
| DMAP | 4-N,N-dimethylaminopyridine |
| DMF | N,N-dimethylformamide |
| DMSO | dimethylsulphoxide |
| EE, EtOAc | ethyl acetate |
| eq | equivalent(s) |
| ESI | electron spray ionization |
| Et | ethyl |
| h | hour |
| hex | hexyl |
| HPLC | high performance liquid chromatography |
| Hünig-base | N-ethyl-N,N-diisopropylamine |
| i | iso |
| IR | infrared spectroscopy |
| cat. | catalyst, catalytic |
| conc. | concentrated |
| LC | liquid chromatography |
| LDA | lithium diisopropylamide |
| Me | methyl |
| min | minutes |
| MS | mass spectrometry |
| NMP | N-methylpyrrolidone |
| n.a. | not available |
| Ph | phenyl |
| Pr | propyl |
| $R_f(Rf)$ | retention factor |
| RP | reversed phase |
| RT | ambient temperature |
| $t_{Ret.}$ | retention time (HPLC) |
| tert. | tertiary |
| THF | tetrahydrofuran |
| TBTU | O-(benzotriazol-1-yl)-N,N,N',N'-tetramethyl-uronium tetrafluoroborate |
| tBu | tert.-butyl |
| TCDI | thiocarbonyldiimidazole |
| UV | ultraviolet |

Features and advantages of the present invention will become apparent from the following detailed Examples, which illustrate the basics of the invention by way of example, without limiting its scope.

Preparation of the Compounds According to the Invention

General

All the reactions are carried out—unless stated otherwise—in commercially obtainable apparatus using methods conventionally used in chemical laboratories.

Air- and/or moisture-sensitive starting materials are stored under protective gas and corresponding reactions and manipulations using them are carried out under protective gas (nitrogen or argon).

Microwave reactions are carried out in an EMRY OPTIMIZER made by Personal Chemistry in sealed containers (5 or 20 mL), preferably with stirring.

Chromatography

For the preparative medium pressure chromatography (MPLC, normal phase) silica gel is used which is made by Millipore (named: Granula Silica Si-60A 35-70 μm) or C-18 RP-silica gel (RP-phase) made by Macherey Nagel (named: Polygoprep 100-50 C18). The thin layer chromatography is carried out on ready-made silica gel 60 TLC plates on glass (with fluorescence indicator F-254) made by Merck.

For the preparative high pressure chromatography (HPLC) columns made by Waters (named: XTerra Prep. MS C18, 5 μM, 30×100 mm or XTerra Prep. MS C18, 5 μm, 50×100 mm OBD or Symmetrie C18, 5 μm, 19×100 mm) are used, the analytical HPLC (reaction control) is carried out with columns made by Agilent (named: Zorbax SB-C8, 5 μm, 21.2×50 mm).

HPLC Mass Spectroscopy/UV Spectrometry

The retention times/MS-ESI$^+$ for characterising the examples are obtained using an HPLC-MS apparatus (high performance liquid chromatography with mass detector) made by Agilent. Compounds that elute with the injection peak are given the retention time $t_{Ret.}$=0.0 min.

The apparatus has the following specification:

| | |
|---|---|
| Column: | Waters, Xterra MS C18, 2.5 μm, 2.1 × 30 mm, Part. No. 186000592 |
| Eluant: | A: H$_2$O with 0.1% HCOOH; B: acetonitrile (HPLC grade) |
| Detection: | MS: Positive and negative mode |
| Mass range: | 120-900 m/z |
| Fragmentor: | 120 |
| EMV Gain: | 1; Threshold: 150; Stepsize: 0.25; UV: 254 nm; Bandwide: 1 |
| Injection: | Inj. Vol. 5 μL |
| Separation: | Flow rate 1.10 mL/min |
| Column temp.: | 40° C. |
| Gradient: | 0.0 min: 5% solvent B |
| | 0.0-2.50 min: 5% → 95% solvent B |
| | 2.50-2.80 min: 95% solvent B |
| | 2.81-3.10 min: 95% → 5% solvent B |

Retention times marked *$^1$ to *$^4$ are obtained with the same HPLC-MS apparatus and solvents, but using Agilent Zorbax SB-C8, 2.1×50 mm, 3.5 μm columns and the following parameters:

| Designation | gradient | column temperature | flow rate |
|---|---|---|---|
| *$^1$ | 0.00-0.07 min: 20% solvent B<br>0.07-1.75 min: 20 → 95% solvent B | 45° C. | 1.1 mL/min |
| *$^2$ | 0.00-0.26 min: 5% solvent B<br>0.26-2.01 min: 5 → 95% solvent B | 35° C. | 1.2 mL/min |
| *$^3$ | 0.00-0.01 min: 10% solvent B<br>0.01-3.00 min: 10 → 90% solvent B | 45° C. | 0.6 mL/min |
| *$^4$ | 0.00-1.50 min: 5 → 95% solvent B<br>1.50-1.51 min: 95 → 100% solvent B<br>1.51-2.00 min: 100% solvent B | 35° C. | 1.2 mL/min |

The compounds according to the invention may be prepared by the methods of synthesis described below. These methods are intended to illustrate the invention without restricting it to their content or limiting the scope of the compounds claimed to these Examples. Where the preparation of the starting compounds is not described, they are commercially obtainable or may be prepared analogously to known compounds or methods described herein. Substances described in the literature are prepared according to the published methods of synthesis.

Scheme A
The designations $R^{1a}$-$R^{1i}$ used in Scheme A-D are defined analogously to $R^{4a}$ hereinbefore.
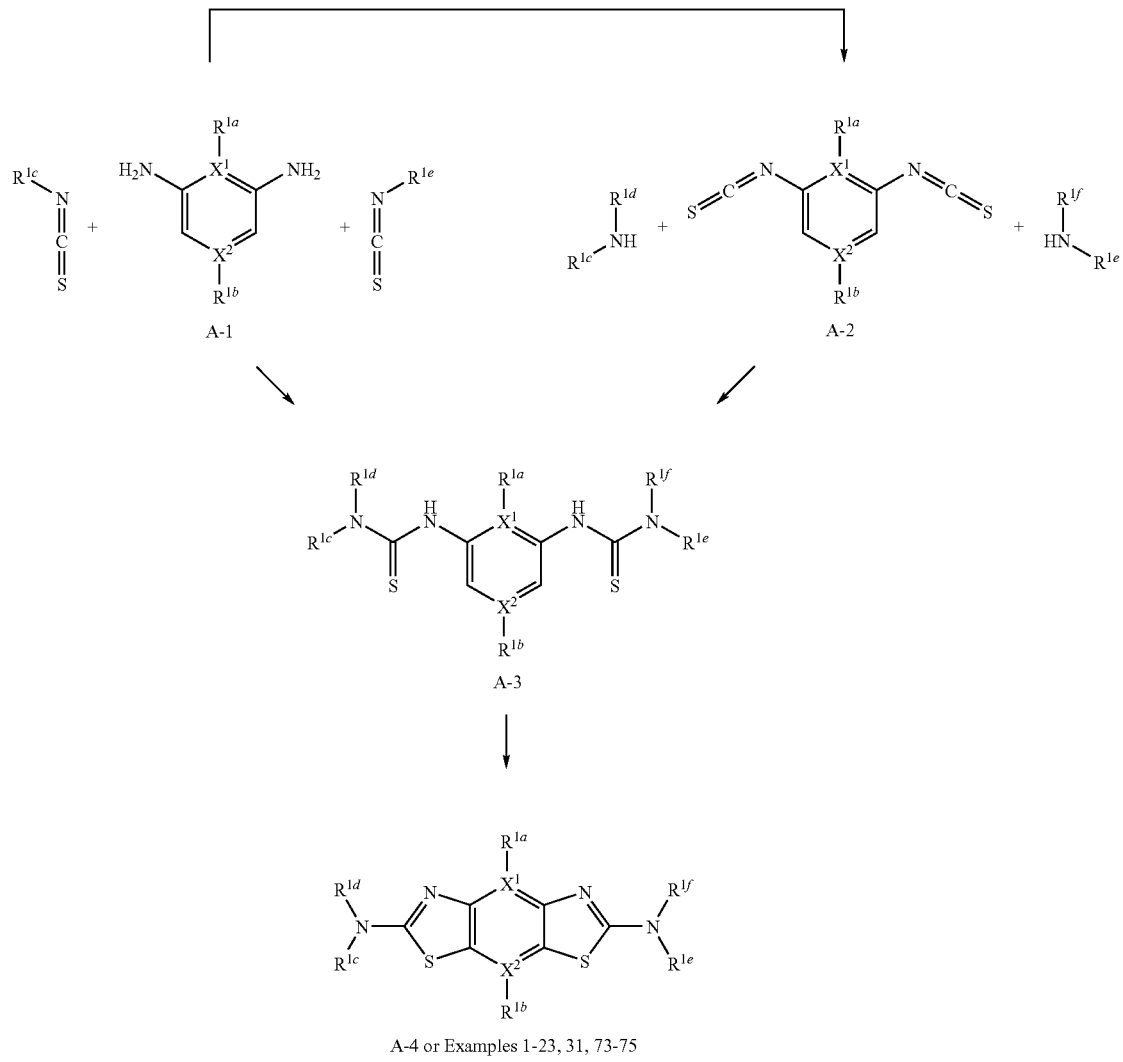
A-4 or Examples 1-23, 31, 73-75
Optionally, additional transformation of functional groups is also possible according to the synthesis of A-4, cE also Scheme C-D.
Scheme B
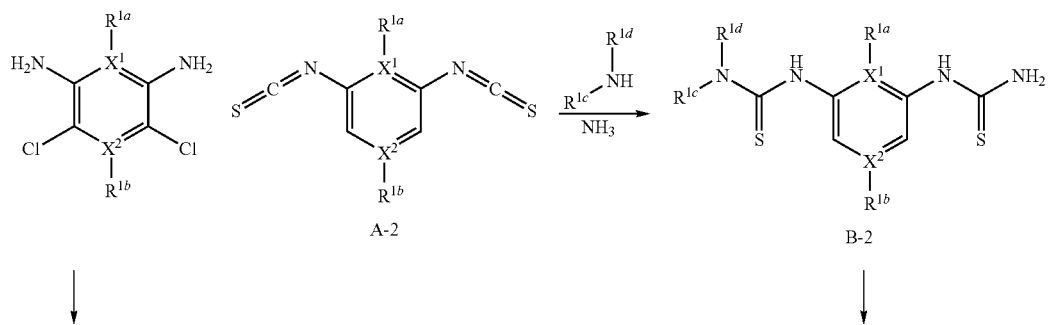

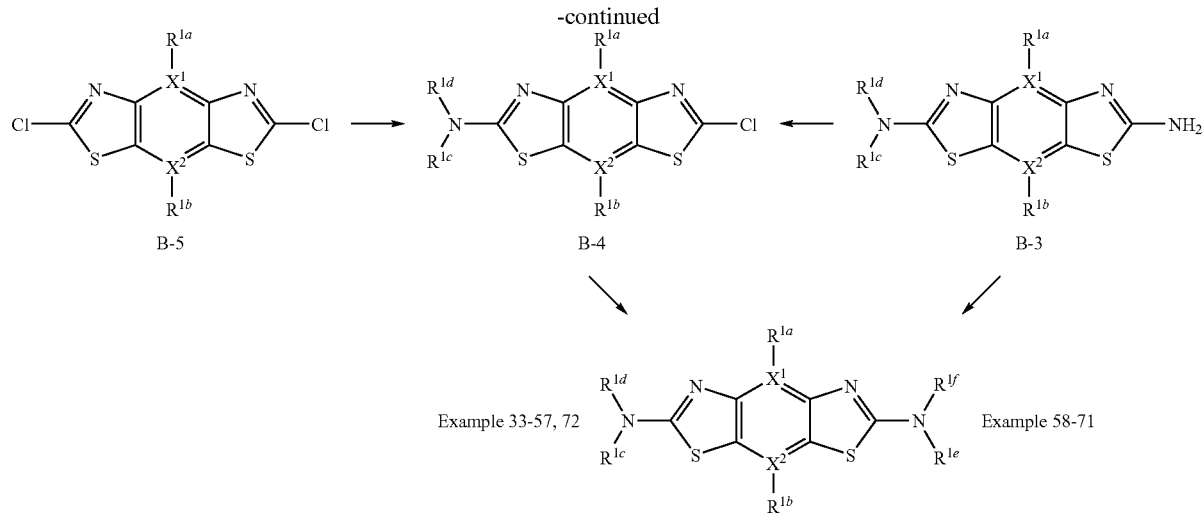
B-5 → B-4 ← B-3
Example 33-57, 72    Example 58-71
Scheme C
The linker group used in Scheme C and D is preferably Z as hereinbefore defined.
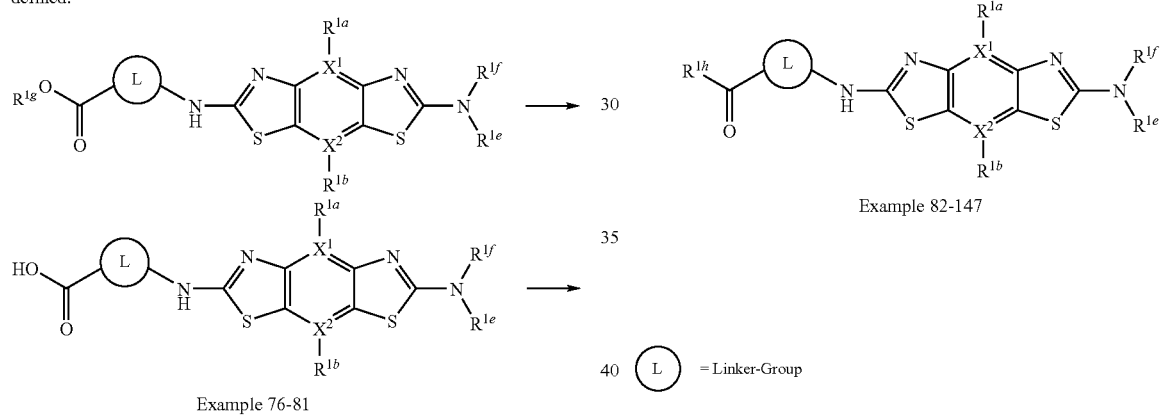
Example 76-81
Example 82-147
○L○ = Linker-Group
Scheme D
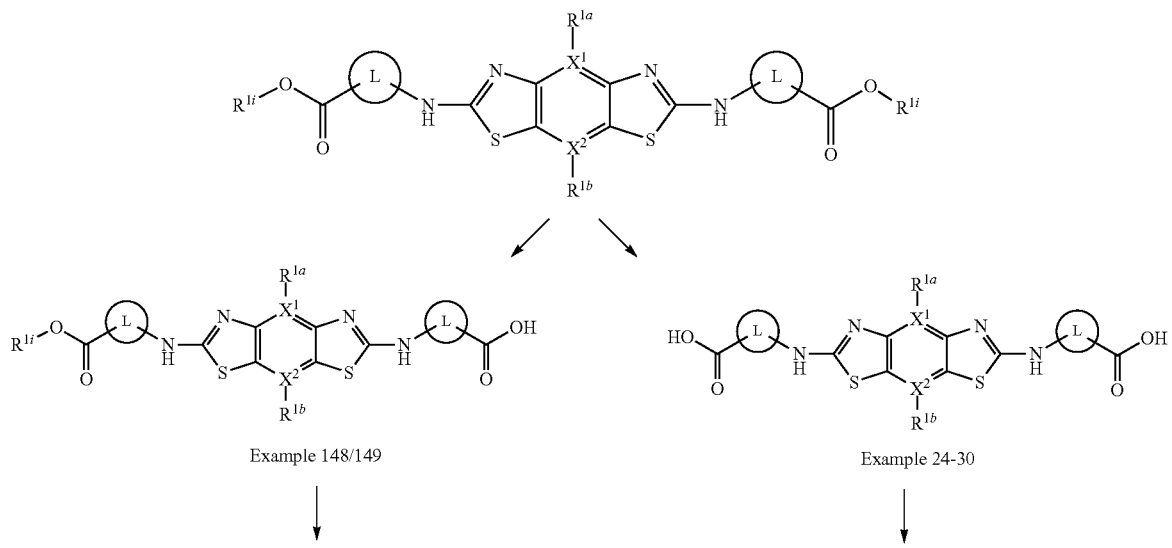
Example 148/149    Example 24-30

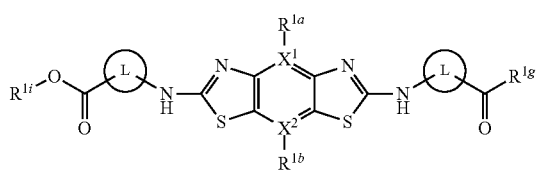

Example 150/152

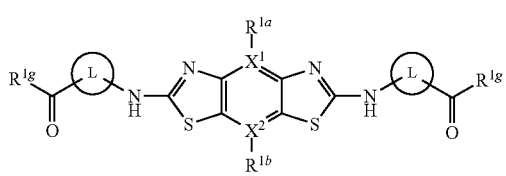

Example 32, 156-163

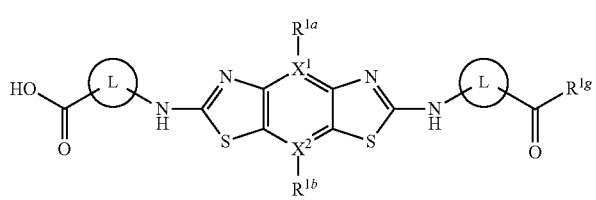

Example 153/155

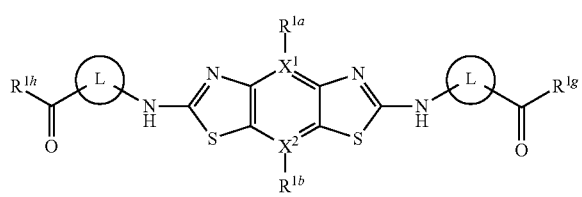

Example 164/177

(L) = Linker Group

Preparation of the Starting Compounds

Preparation of A-1a:

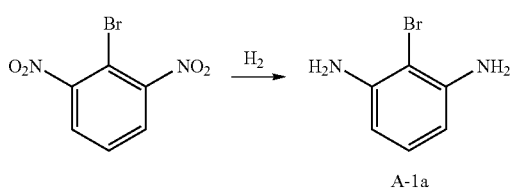

A-1a

A solution of 2-bromo-1,3-dinitrobenzene (2 g, 8.1 mmol) in 100 mL THF is combined with 0.5 g Raney nickel and shaken overnight at RT under 6 bar $H_2$ atmosphere. The reaction mixture is filtered, the filtrate is freed from the volatile constituents in vacuo and the crude product is further used directly. (HPLC $t_{Ret.}$=0.34 min*[1]; MS [M+H]$^+$: m/z=187/189)

Preparation of A-1b:

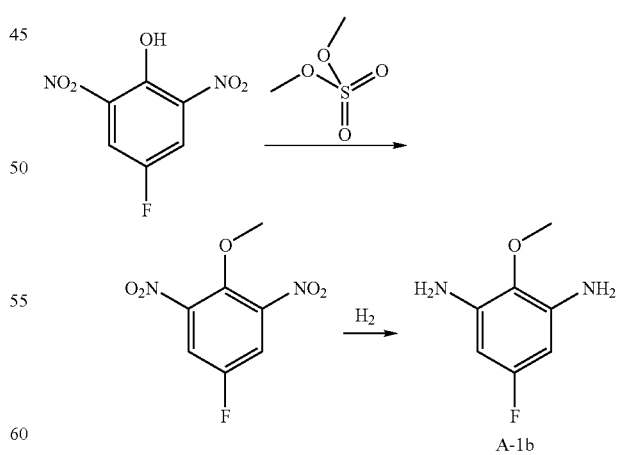

A-1b $K_2CO_3$ (376 mg, 2.37 mmol) and dimethylsulphate (370 µL, 3.88 mmol) is added to a solution of 2,6-dinitro-4-fluorophenol (0.5 g, 202 mmol) in 4.5 mL acetone. After 20 h stirring at 60° C. the reaction mixture is diluted with DCM and extracted with water. The organic phase is dried. After elimination of the volatile constituents the methylated intermediate product is obtained, which is taken up in 100 mL methanol and combined with 100 mg Raney nickel. After 1.5 h shaking under 8 bar H$_2$-atmosphere the reaction mixture is filtered and combined with an HCl solution in dioxane. After elimination of the volatile constituents the product A-1b is obtained.

(HPLC t$_{Ret.}$=0.0 min; MS [M+H]$^+$: m/z=157)

Preparation of A-1c:

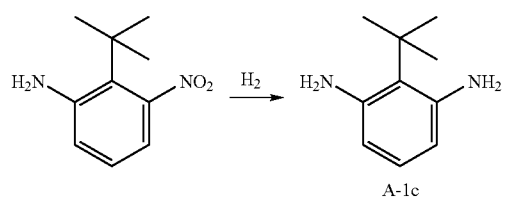

A-1c

A solution of 2-tert.-butyl-3-nitroaniline (500 mg, 2.57 mmol) in 100 mL THF is combined with 700 mg Raney nickel and stirred for 16 h at 8 bar H$_2$-atmosphere. The catalyst is filtered off and the filtrate is combined with 10 mL 4N HCl in dioxane. The volatile constituents are eliminated in vacuo and the product A-1c is further used directly. (HPLC t$_{Ret.}$=0.0 min; MS [M+H]$^+$: m/z=165)

Preparation of A-1d:

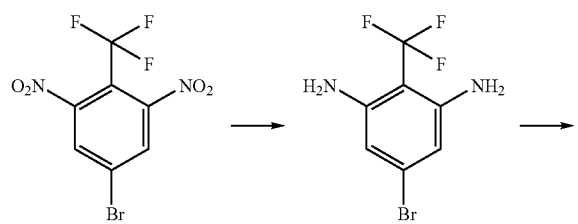

A-1d

A solution of 4-bromo-2,6-dinitro-α,α,α-trifluorotoluene (1.5 g, 4.76 mmol) in 75 mL of a mixture of methanol/THF is added at 60° C. to a mixture of 2 g iron powder, 1.6 g NH$_4$Cl and 30 mL water. After 3 h stirring the reaction mixture is filtered and freed from the volatile constituents. Using a mixture of DCM and heptane the reduced intermediate product is extracted. This is dissolved in 25 mL methanol and hydrogenated with Pd/C at 1 bar H$_2$ pressure. The product A-1d is obtained from the reaction mixture by filtration and chromatography (MS [M+H]$^+$: m/z=177)

General Preparation of Bisisothiocyanates A-2:

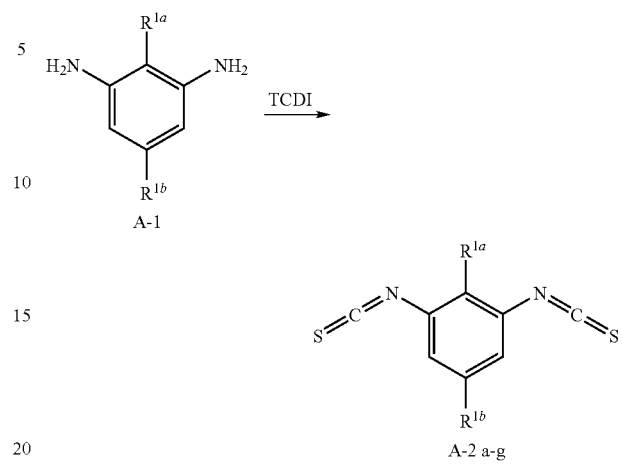

A solution of the corresponding phenylenediamine and 2-3 eq TCDI in DCM is stirred at RT until the reaction is complete. After elimination of the volatile components the crude product is obtained. The product is isolated by chromatography.

TABLE 1

| # | R$^{1a}$ | R$^{1b}$ | t$_{Ret.}$ (HPLC) [min] |
|---|---|---|---|
| A-2a | CF$_3$ | H | n.a. |
| A-2b | Me | H | 2.64*$^2$ |
| A-2c | H | CF$_3$ | n.a. |
| A-2d | H | H | n.a. |
| A-2e | Cl | H | 2.43 |
| A-2f | F | H | 2.43 |
| A-2g | tBu | H | n.a. |

General Method for Synthesising the Compounds A-3a-f:

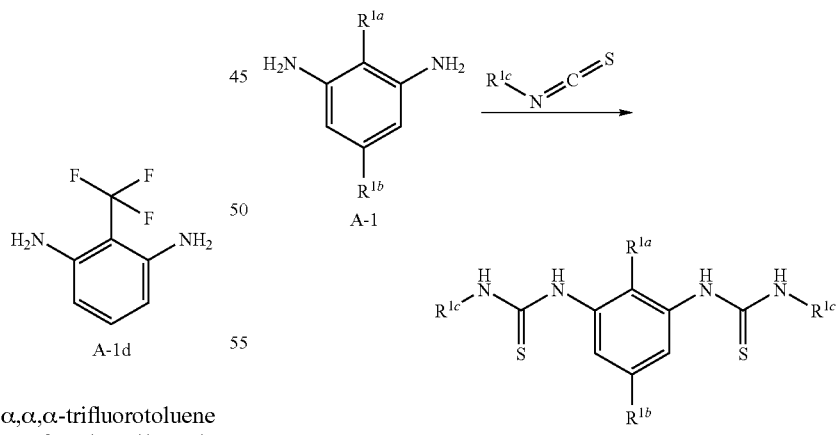

A solution of the corresponding phenylenediamine A-1 and the corresponding isothiocyanate (2.1-2.6 eq) is stirred in a suitable solvent at a defined temperature. After it has been established that the reaction is complete the solvents are eliminated in vacuo and the reaction product is used in the next step without further purification.

TABLE 2

| # | $R^{1a}$ | $R^{1b}$ | $R^{1c}$ | conditions | $t_{Ret.}$ (HPLC) [min] | MS (ESI+) $[M + H]^+$ |
|---|---|---|---|---|---|---|
| A-3a | H | H | ethyl 2-methylpropanoate group | dioxane, 50° C. | 1.87 | 427 |
| A-3b | H | H | methyl butanoate group | dioxane, 50° C. | 1.51 | 399 |
| A-3c | Br | H | methyl propanoate group | dioxane, 45° C. | 1.32 | 449 |
| A-3d | H | H | methyl propanoate group | dioxane, 50° C. | 1.37 | 371 |
| A-3e | Me | H | methyl propanoate group | dioxane, 60° C. | 1.32 | 385 |
| A-3f | $NMe_2$ | H | methyl propanoate group | dioxane, RT | n.a. | 382 |

Preparation of A-3g:

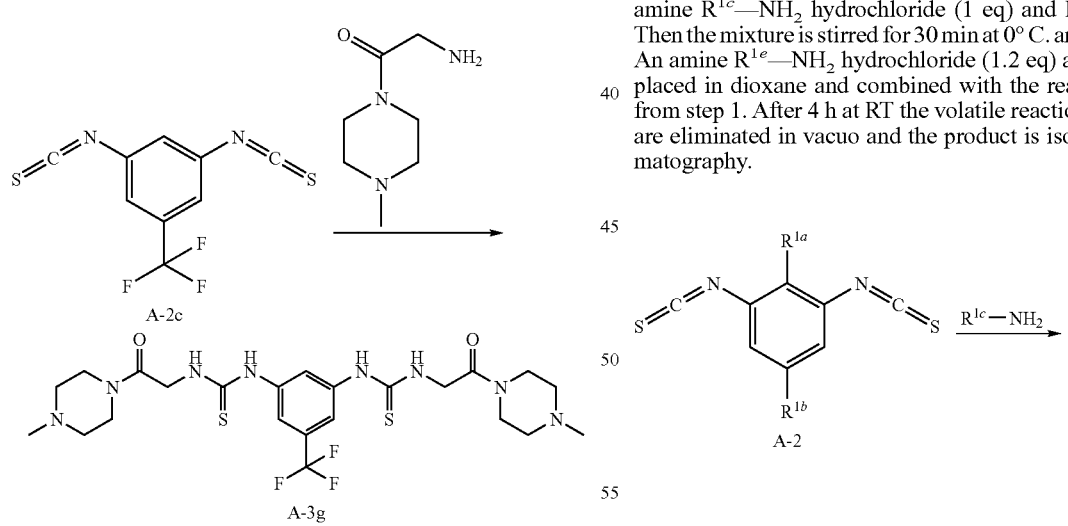

A solution of A-2c (250 mg, 0.961 mmol) and 2-amino-1-(4-methyl-piperazin-1-yl)-ethanone dihydrochloride (480 mg, 2.086 mmol) in dry DMA is combined with DIPEA (0.74 mL, 4.264 mmol) under protective gas and stirred for 16 h at RT. After elimination of the volatile reaction components the residue is purified by RP phase (eluant: $ACN/H_2O$). The title compound is obtained as a solid. (MS $[M+H]^+$: m/z=575)

Compound A-3h is prepared analogously to compound A-3g.

General Method for Synthesising the Compounds A-3 i-p:

A solution of A-2 in dry DMA is combined at 0° C. with an amine $R^{1c}$—$NH_2$ hydrochloride (1 eq) and DIPEA (1 eq). Then the mixture is stirred for 30 min at 0° C. and for 1 h at RT. An amine $R^{1e}$—$NH_2$ hydrochloride (1.2 eq) and DIPEA are placed in dioxane and combined with the reaction solution from step 1. After 4 h at RT the volatile reaction components are eliminated in vacuo and the product is isolated by chromatography.

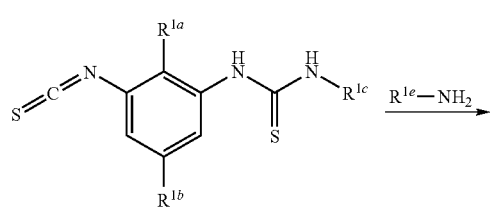

-continued
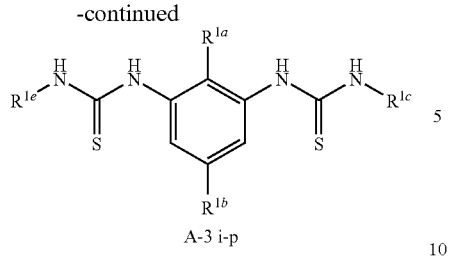
A-3 i-p
TABLE 3
| # | $R^{1a}$ | $R^{1b}$ | $R^{1c}$-NH$_2$ | $R^{1e}$-NH$_2$ | $t_{Ret.}$ (HPLC) [min] | MS (ESI+) [M + H]$^+$ |
|---|---|---|---|---|---|---|
| A-3g | H | CF$_3$ | | | n.a. | 575 |
| A-3h | H | CF$_3$ | | | 2.20*$^3$ | 439 |
| A-3i | Me | H | | | n.a. | 423 |
| A-3j | CF$_3$ | H | | | 1.34 | 546 |
| A-3k | Me | H | | | 1.87 | 496 |
| A-3l | Me | H | | | n.a. | 500 |

TABLE 3-continued

| # | $R^{1a}$ | $R^{1b}$ | $R^{1c}$-NH$_2$ | $R^{1e}$-NH$_2$ | $t_{Ret.}$ (HPLC) [min] | MS (ESI+) [M + H]$^+$ |
|---|---|---|---|---|---|---|
| A-3m | Me | H | (H$_2$N-CO-CH(NH$_2$)-CH$_2$-CO-N-methylpiperazine) | (pyrrolidine-CO-CH$_2$-NH$_2$) | n.a. | 549 |
| A-3n | Me | H | (BocHN-CH$_2$-CH(NH$_2$)-CO-pyrrolidine) | (pyrrolidine-CO-CH$_2$-NH$_2$) | 1.85 | 592 |
| A-3o | Me | H | (iPr-CH(NH$_2$)-CO-N-methylpiperazine) | (pyrrolidine-CO-CH$_2$-NH$_2$) | n.a. | 534 |
| A-3p | H | H | (N-methylpiperazine-CO-CH$_2$-NH$_2$) | (2-oxo-pyrrolidine-N-CH$_2$CH$_2$-NH$_2$) | n.a. | 478 |

General Method for Synthesising the Compounds A-3 q-v:

A solution of phenylenediamine-dihydrochloride A-1 in DMA and DIPEA (3 eq) is combined with a solution of 2-isothiocyanato-1-pyrrolidin-1-yl-ethanone in DMA (1 eq) and shaken for 16 h at RT. Then a solution of 2-isothiocyanato-1-(4-methyl-piperazin-1-yl)-ethanone (1.1 eq) in DMA is added and the mixture is shaken for 16 h at 55° C. After chromatography through RP-phase (eluant: ACN/H$_2$O) the title compound A-3 is obtained as a solid.

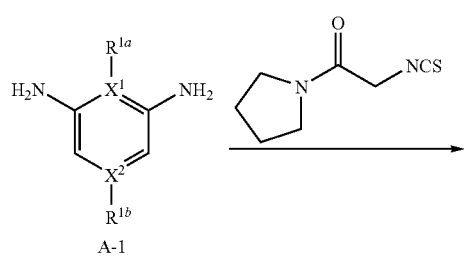

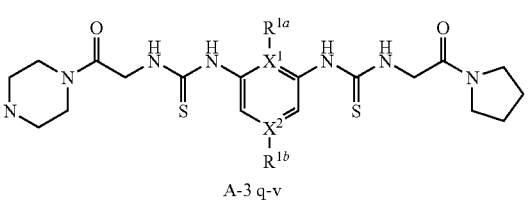

A-3 q-v

TABLE 4

| # | $R^{1a}$ | $R^{1b}$ | $X^1$ | $X^2$ | $t_{Ret.}$ (HPLC) [min] | MS (ESI+) $[M + H]^+$ |
|---|---|---|---|---|---|---|
| A-3q | tBu | H | C | C | 1.281 | 534 |
| A-3r | H | $NH_2$ | C | C | 0.0 | 493 |
| A-3s | OMe | Me | C | C | 0.0 | 522 |
| A-3t | OMe | F | C | C | 0.0 | 526 |
| A-3u | H | H | C | N | 0.0 | 479 |
| A-3v | Cl | Me | C | C | 0.0 | 526 |

Preparation of A-3w:

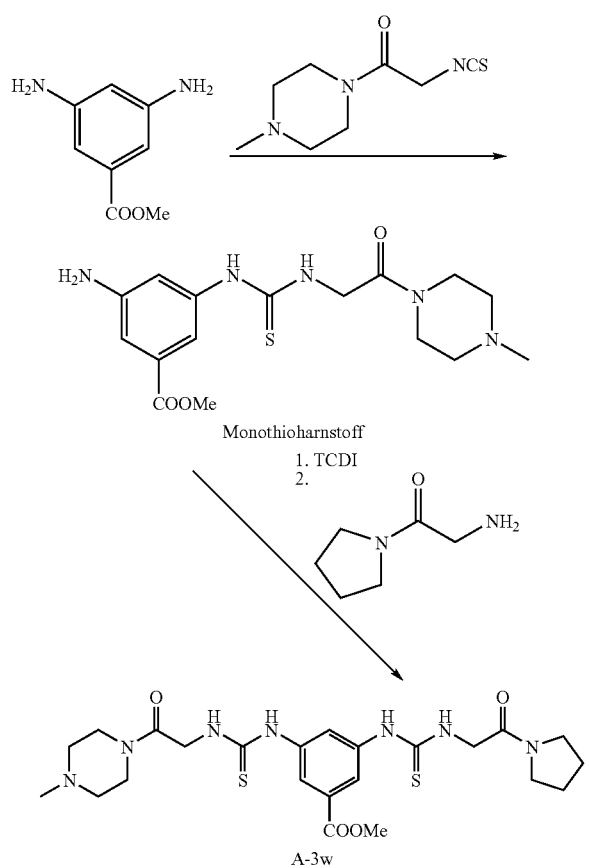

Methyl 3,5-diaminobenzoate (58.4 mg, 0.351 mmol) is added to a solution of 2-isothiocyanato-1-(4-methyl-piperazin-1-yl)-ethanone (70.0 mg, 0.351 mmol) in THF (0.6 mL) and stirred for 2 h at RT. After elimination of the volatile solvent in vacuo the residue is purified by RP phase. The monothiourea intermediate product (32 mg, 0.088 mmol) is dissolved in DCM (0.5 mL), combined with TCDI (17.9 mg, 0.096 mmol) and shaken for 4 h at 35° C. The volatile reaction components are eliminated in vacuo and the residue is dissolved in DMA (0.5 mL). At 0° C. 2-amino-1-pyrrolidin-1-yl-ethanone hydrochloride (17.9 mg, 0.109 mmol) and DIPEA (30 μL, 0.186 mmol) are added and the mixture is shaken for 30 min at RT. The reaction mixture is mixed with water (0.3 mL) and chromatographed through RP-phase. A-3w is obtained as a solid. (HPLC $t_{Ret.}$=0.0 min; MS $[M+H]^+$: m/z=536)

General Method for Synthesising the Compounds A-3x-ac:

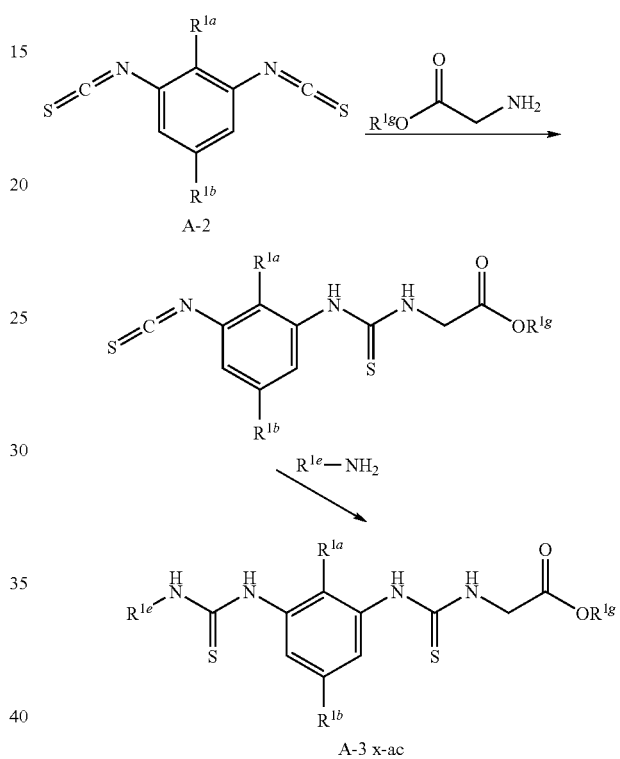

A solution of bisisothiocyanate A-2 and glycine ester (1.0-1.2 eq) is stirred in a suitable solvent at RT. Equimolar amounts of DIPEA are additionally added for glycine ester hydrochlorides. Once it has been established that the reaction is complete the solvents are eliminated in vacuo. The crude intermediate product is dissolved in a suitable solvent, combined with amine $R^{1e}$—$NH_2$ and stirred at RT. In the case of $R^{1e}$—$NH_2$ hydrochlorides equimolar amounts of DIPEA are additionally added. Once it has been established that the reaction is complete the solvents are eliminated in vacuo and the product A-3 is purified by chromatography.

TABLE 5

| # | $R^{1a}$ | $R^{1b}$ | $R^{1g}$ | $R^{1e}$-$NH_2$ | solvent | $t_{Ret.}$ (HPLC) [min] | MS (ESI+) $[M + H]^+$ |
|---|---|---|---|---|---|---|---|
| A-3x | Me | H | Me | (piperidinyl-C(O)-CH2-NH2) | dioxane | 0.74*[1] | 438 |

TABLE 5-continued

| # | $R^{1a}$ | $R^{1b}$ | $R^{1g}$ | $R^{1e}$-NH$_2$ | solvent | $t_{Ret.}$ (HPLC) [min] | MS (ESI+) [M + H]$^+$ |
|---|---|---|---|---|---|---|---|
| A-3y | Cl | H | Me | 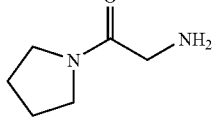 | dioxane | 0.73*$^1$ | 444 |
| A-3z | F | H | Me | 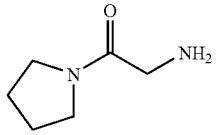 | dioxane | 1.60 | 428 |
| A-3aa | Me | H | tBu | 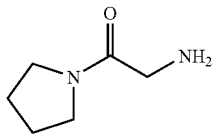 | cyclo-hexane, DCM | 1.71*$^4$ | 466 |
| A-3ab | Me | H | tBu | 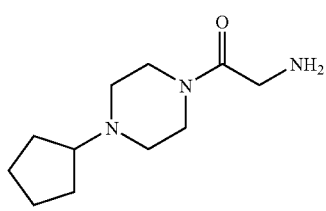 | dioxane | 1.38 | 549 |
| A-3ac | tBu | H | tBu | 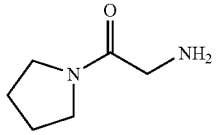 | DCM | 2.16*$^2$ | 508 |

Preparation of A-4:

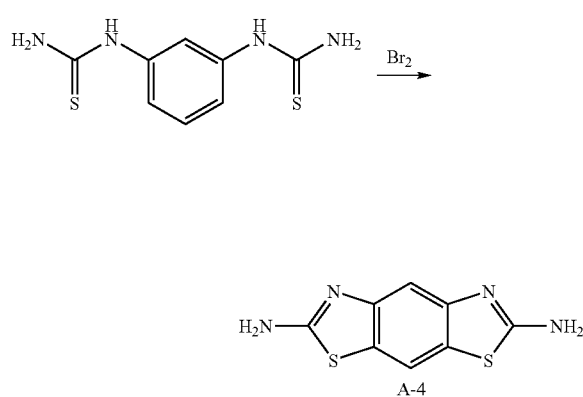

Bromine (6 mL, 116.8 mmol) is added dropwise at RT to a solution of 1,3-bis-thioureido-benzene (5.0 g, 22.09 mmol) in chloroform (100 mL). Then the mixture is refluxed and stirred for 1 h. After cooling to RT the precipitate is filtered off, washed with chloroform and stirred in aqueous sodium bisulphite solution (20 wt. %, 100 mL) for 3 h at 90° C. After cooling to RT the precipitate is filtered off and dissolved in warm 1 N HCl (200 mL). After neutralisation with aqueous NH$_4$OH the title compound is precipitated and can be recrystallised from EE. (MS [M+H]$^+$: m/z=223)

Preparation of B-2a:

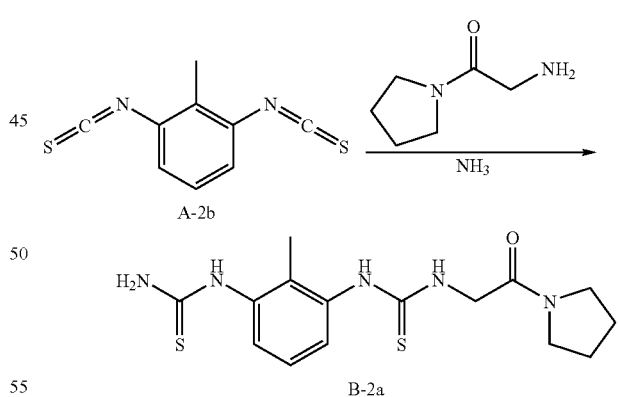

A solution of A-2b (3.02 g, 14.64 mmol) in dry DMA (50 mL) is combined with a solution of 2-amino-1-pyrrolidin-1-yl-ethanone hydrochloride (2.40 g, 14.58 mmol) and DIPEA (2.6 mL, 14.93 mmol) in DMA (50 mL) under protective gas at 0° C. After 30 min stirring at 0° C. an aqueous ammonia solution (1 mL, 32% w/w) is added and the mixture is stirred for a further 10 min at RT. The reaction mixture is purified by RP-phase (eluant: ACN:H$_2$O; gradient: ACN:H$_2$O 10:90→50:50). The product-containing fractions are combined and lyophilised. The title compound is obtained as a solid.

The starting compound B-2b is prepared analogously.

TABLE 6

| # | Structure | $t_{Ret.}$ (HPLC) [min] | MS (ESI+) [M + H]⁺ |
|---|---|---|---|
| B-2a | 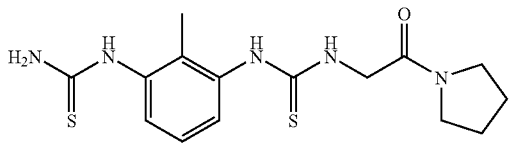 | 0.3-1.2 | 352 |
| B-2b | 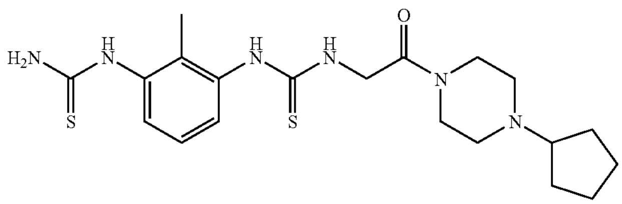 | n.a. | n.a. |

Preparation of B-3a:

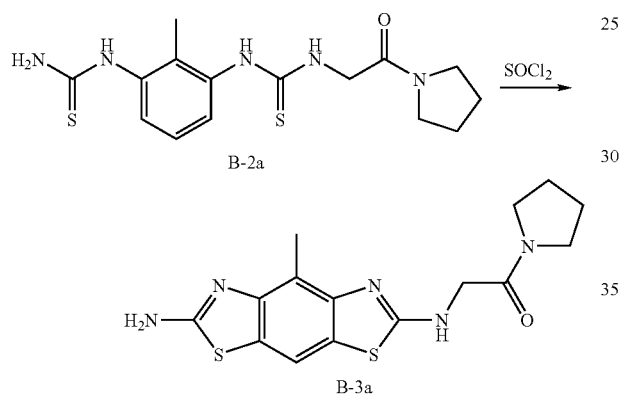

A solution of B-2a (640 mg, 1.473 mmol) in thionyl chloride (5 mL) is stirred for 1 h at 80° C. under protective gas. The volatile reaction components are eliminated in vacuo and the residue is chromatographed on silica gel (gradient elution: eluant DCM:MeOH 9:1→7:3). The product-containing fractions are combined and evaporated down. The title compound is obtained as a solid.

The starting compound B-3b is prepared analogously.

TABLE 7

| # | Structure | $t_{Ret.}$ (HPLC) [min] | MS (ESI+) [M + H]⁺ |
|---|---|---|---|
| B-3a | 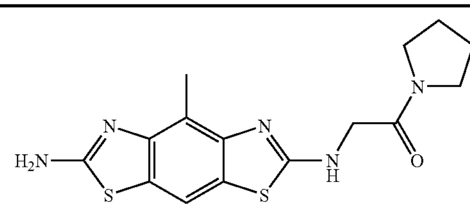 | 1.31 | 348 |
| B-3b | 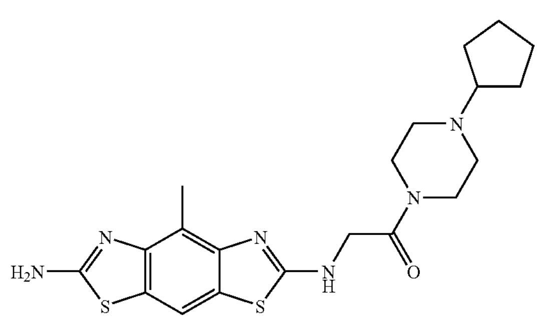 | 0.0 | 431 |

Preparation of B-4-a:

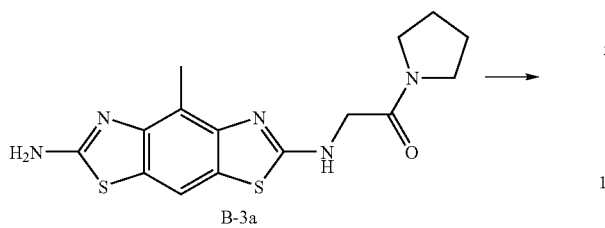

Preparation of B-5a:

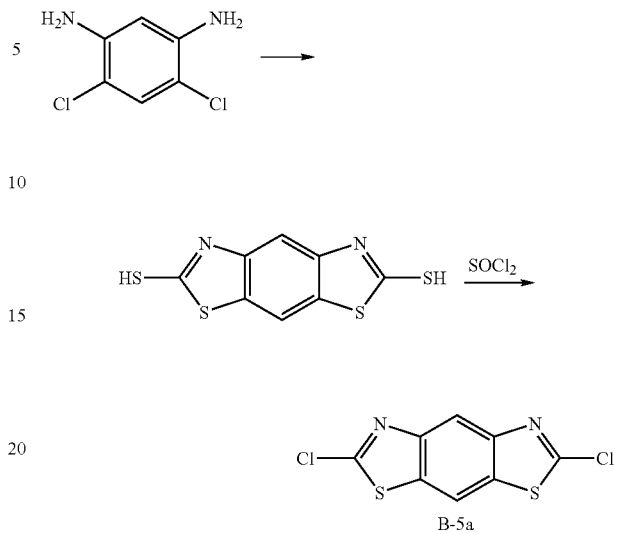

CuCl$_2$ (269 mg, 1.94 mmol) and isoamylnitrite (1015 µL, 7.25 mmol) are placed in ACN (12 mL) and a suspension of B-3a (337 mg, 0.97 mmol) in ACN (24 mL) and DMA (6 mL) is added dropwise. Then the mixture is stirred for 1 h at 40° C. After cooling to RT the volatile reaction components are eliminated in vacuo and the residue is chromatographed by RP-phase (ACN+0.2% HCOOH:H$_2$O+0.2% HCOOH; gradient: 5:95→95:5). The product-containing fractions are combined and freeze-dried. The title compound B-4a is obtained as a solid.

The starting compound B-4b is prepared analogously.

A solution of 2,4-dichloro-5-amino-aniline (4.1 g, 23.2 mmol) in DMF (50 mL) is combined with potassium-ethylxanthogenate and stirred for 3 days at 150° C. After cooling to RT the mixture is diluted with ice water and acidified with aqueous HCl. The precipitate is filtered off and dried in vacuo until a constant weight is obtained. The title compound is used in the next reaction without further purification (HPLC $t_{Ret.}$=3.9 min; MS [M+H]$^+$: m/z=261).

TABLE 8

| # | Structure | $t_{Ret.}$ (HPLC) [min] | MS (ESI+) [M + H]$^+$ |
|---|---|---|---|
| B-4a | 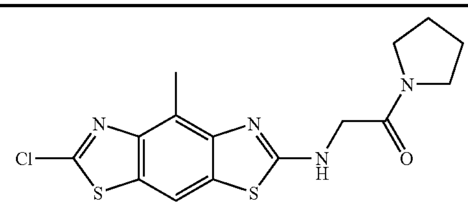 | 2.09 | 367 |
| B-4b | 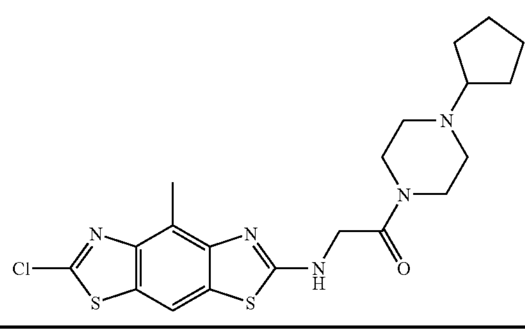 | 1.63 | 449 |

Preparation of B-4c:

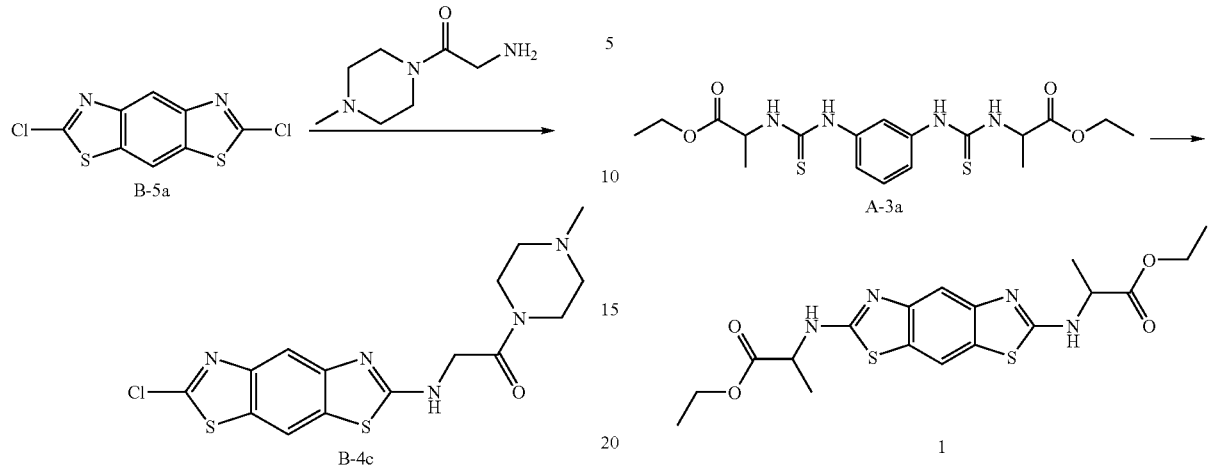

2-amino-1-(4-methyl-piperazin-1-yl)-ethanone dihydrochloride (176 mg, 0.766 mmol) and DIPEA (166.8 µL, 1.532 mmol) are added to a solution of B-5a (200 mg, 0.766 mmol) in NMP (2 mL) and the reaction mixture is stirred for 30 min at 150° C. (microwave). After cooling to RT the mixture is divided between EE and water and filtered. The organic phase is dried on sodium sulphate and evaporated down. The product B-4c is used in the next reaction without further purification.

Example 1

Table 9 (Synthesis Scheme A)

A solution of A-3a (2.0 g, 4.689 mmol) in chloroform (20 mL) is combined at RT with a solution of bromine (506 µL, 10 mmol) in chloroform (30 mL) or the corresponding amount of benzyltrimethylammonium tribromide (3.90 g, 10 mmol) and after it has all been added the mixture is refluxed for 1 h. After cooling to RT the solvent is eliminated in vacuo and the residue is divided between aqueous ammonia and EE. The organic phase is dried and concentrated in vacuo. The crude product is purified by chromatography.

Example 2-12 are prepared analogously (Table 9)

TABLE 9

| # | Structure | $t_{Ret.}$ (HPLC) [min] | MS (ESI+) [M + H]$^+$ |
|---|---|---|---|
| 1 | 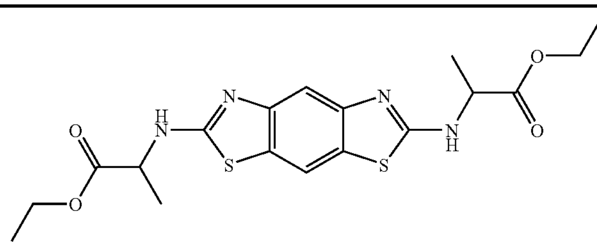 | 1.79 | 423 |
| 2 | 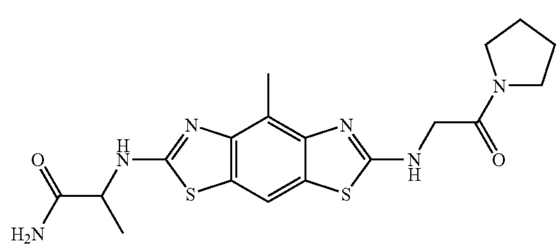 | 1.39 | 419 |
| 3 | 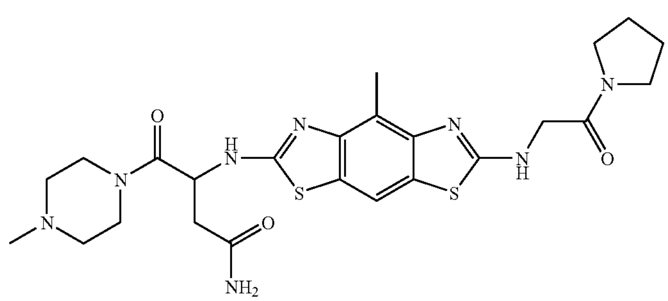 | 0.0 | 545 |

TABLE 9-continued

| # | Structure | $t_{Ret.}$ (HPLC) [min] | MS (ESI+) $[M + H]^+$ |
|---|---|---|---|
| 4 | 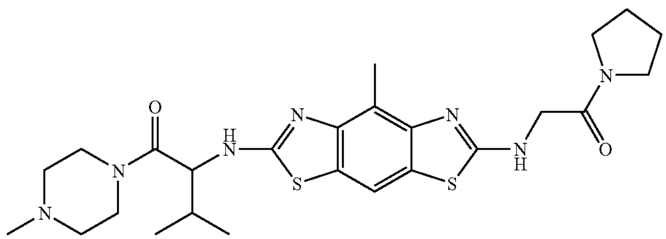 | 1.44 | 530 |
| 5 | 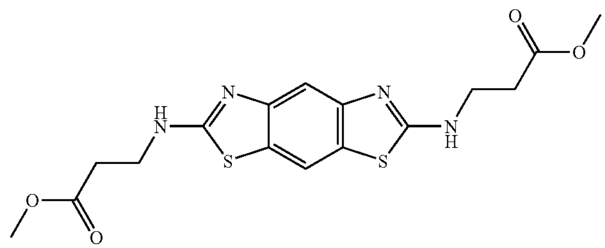 | 1.39 | 395 |
| 6 | 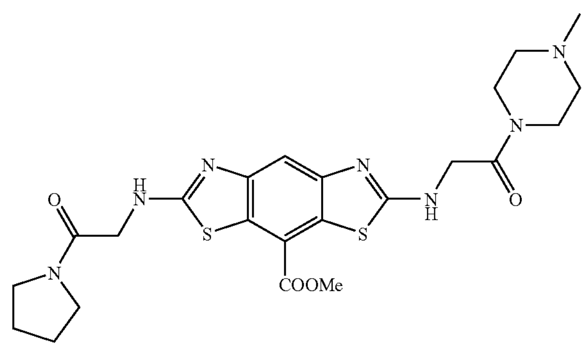 | 1.31 | 532 |
| 7 | 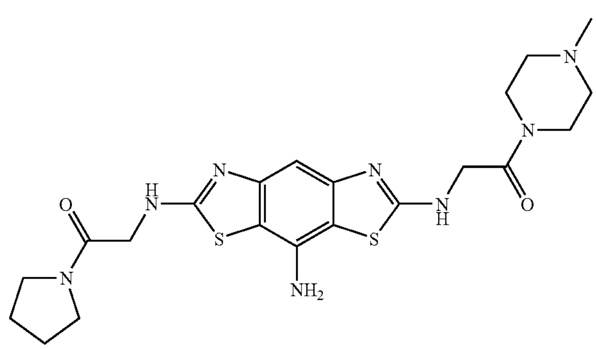 | 0.0 | 489 |
| 8 | 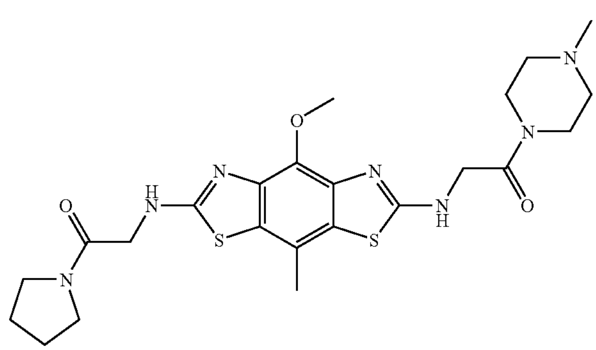 | 1.29 | 518 |

TABLE 9-continued

| # | Structure | t$_{Ret.}$ (HPLC) [min] | MS (ESI+) [M + H]$^+$ |
|---|---|---|---|
| 9 | 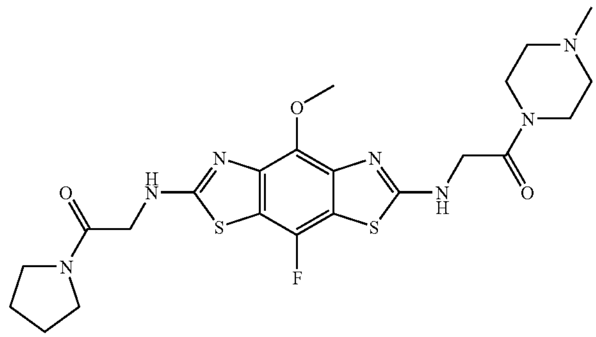 | 0.0 | 522 |
| 10 | 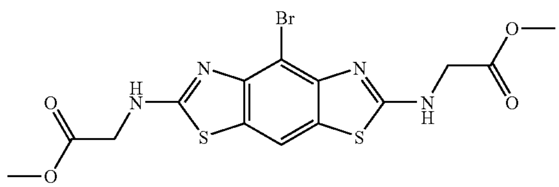 | 1.65 | 445/447 |
| 11 | 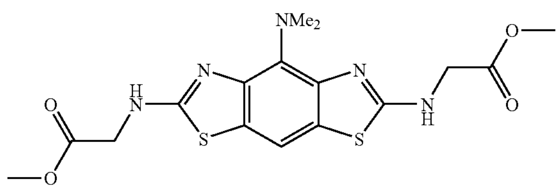 | 0.0 | 410 |
| 12 | 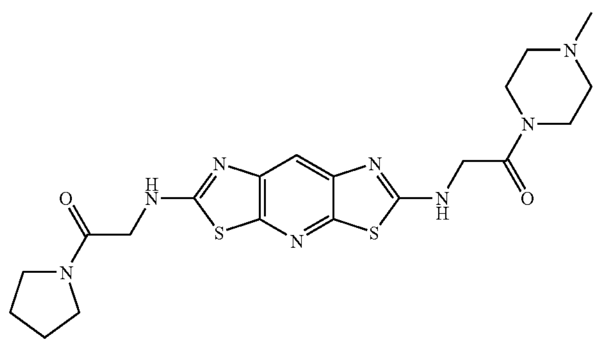 | 1.33 | 475 |
| 13 | 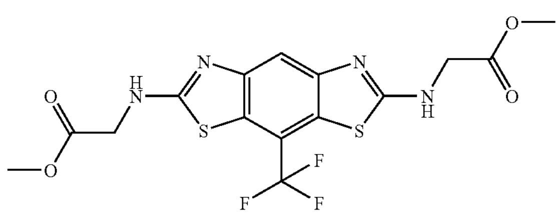 | 1.77 | 435 |
| 14 | 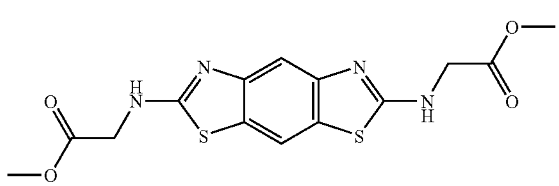 | 1.35 | 367 |

TABLE 9-continued

| # | Structure | $t_{Ret.}$ (HPLC) [min] | MS (ESI+) [M + H]$^+$ |
|---|-----------|---|---|
| 15 | 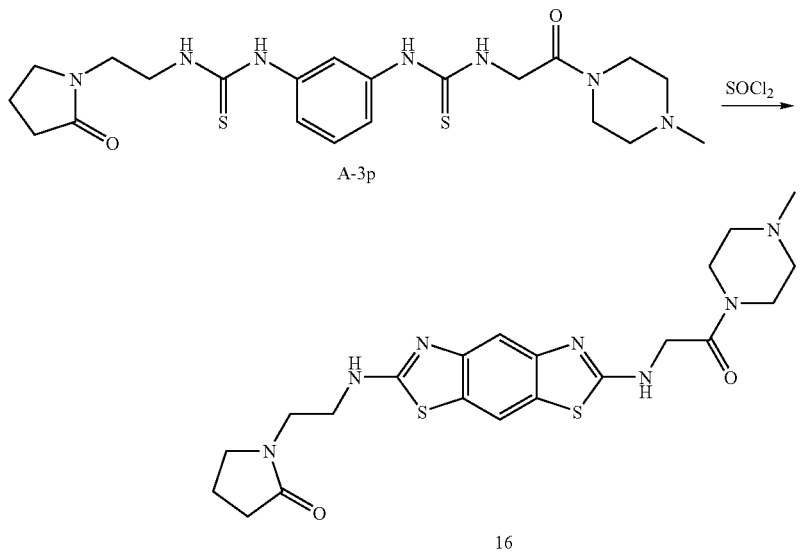 | 1.55 | 381 |

Example 16

Table 10 (Synthesis Scheme A)

A solution of A-3p (512 mg, 1.072 mmol) in thionyl chloride is stirred for 1 h at 55° C. under protective gas. The volatile reaction components are eliminated in vacuo and the residue is chromatographed using RP-phase (eluant ACN: H$_2$O; gradient: ACN:H$_2$O 5:95→95:5). The product-containing fractions are combined and freeze-dried.

Examples 17-23 are prepared analogously (Table 10)

TABLE 10

| # | Structure | $t_{Ret.}$ (HPLC) [min] | MS (ESI+) [M + H]$^+$ |
|---|-----------|---|---|
| 16 | 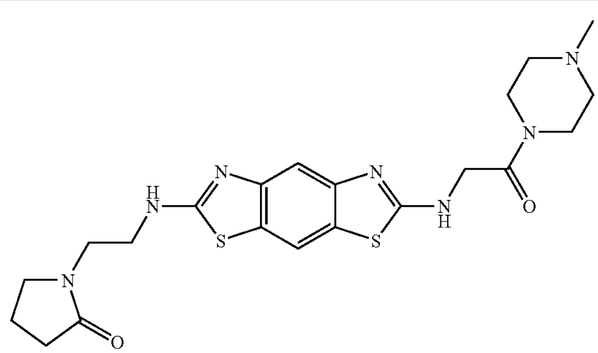 | 0.0 | 474 |

TABLE 10-continued

| # | Structure | t_{Ret.} (HPLC) [min] | MS (ESI+) [M + H]+ |
|---|---|---|---|
| 17 | 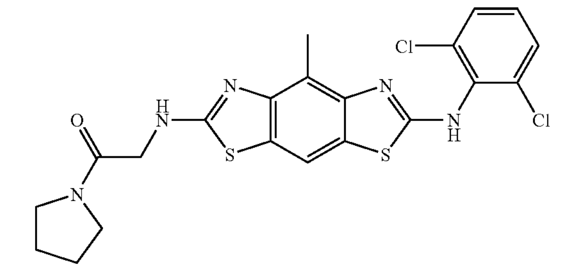 | 2.10 | 492 |
| 18 | 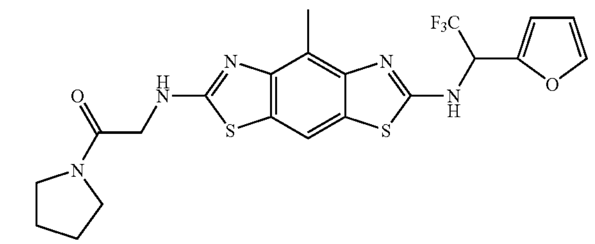 | 2.14 | 496 |
| 19 | 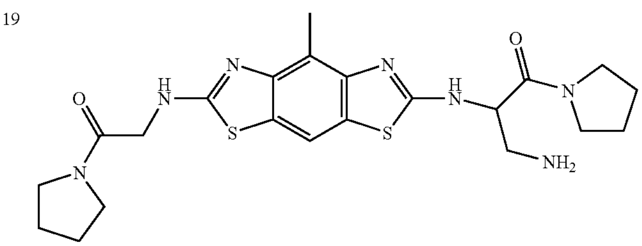 | 0.0 | 488 |
| 20 | 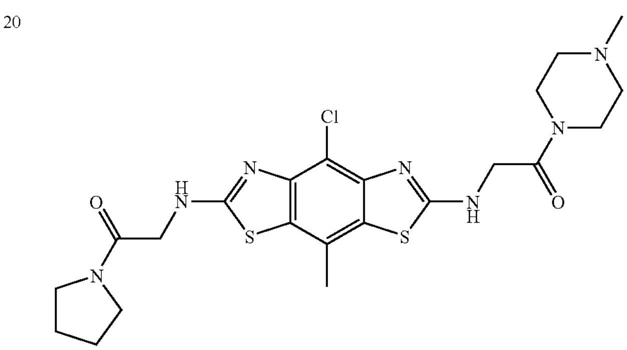 | 0.0 | 522 |
| 21 | 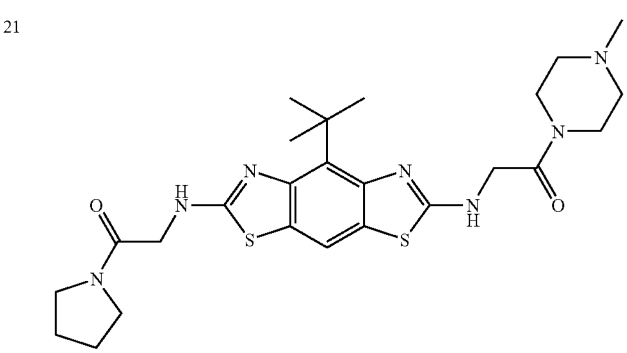 | 1.43 | 530 |

TABLE 10-continued
| # | Structure | t_{Ret.} (HPLC) [min] | MS (ESI+) [M + H]+ |
|---|---|---|---|
| 22 | 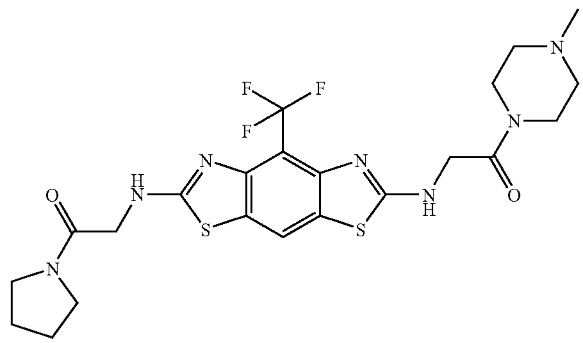 | 1.37 | 542 |
| 23 | 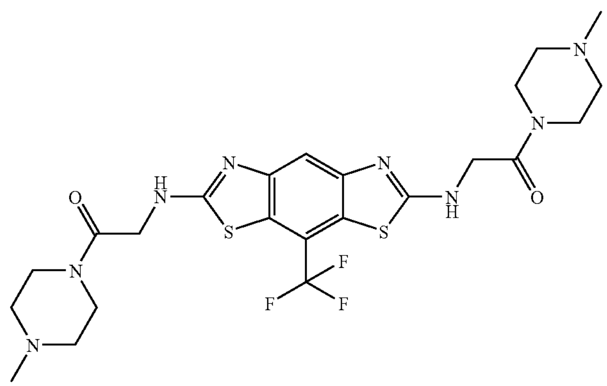 | 0.0 | 571 |
General Method for Synthesising Examples 24-30
Table 11 (Synthesis Scheme D)
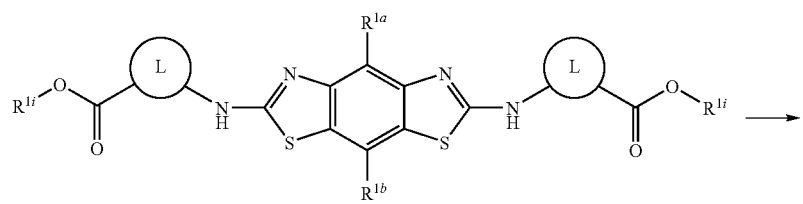
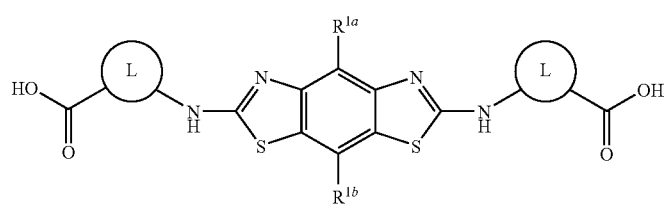
L = Linker Group The corresponding bis-ester is used directly as specified in the Table or dissolved in a little solvent beforehand. 1-10 eq NaOH or KOH are added in the form of an aqueous 0.1-1 M solution and stirred at the specified temperature until the reaction is complete. The reaction mixture may optionally be neutralised by the addition of hydrochloric acid. The crude product is obtained by filtration or evaporation of the reaction mixture and may be further used directly or purified by chromatography.

TABLE 11

| # | Structure | $R^{1i}$ | conditions | $t_{Ret.}$ (HPLC) [min] | MS (ESI+) $[M + H]^+$ |
|---|---|---|---|---|---|
| 24 | 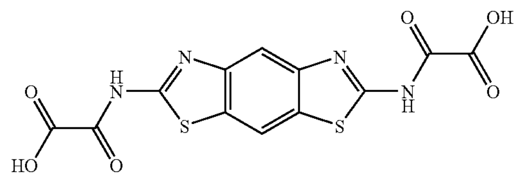 | Me | MeOH, NaOH in H$_2$O, RT | n.a. | n.a. |
| 25 | 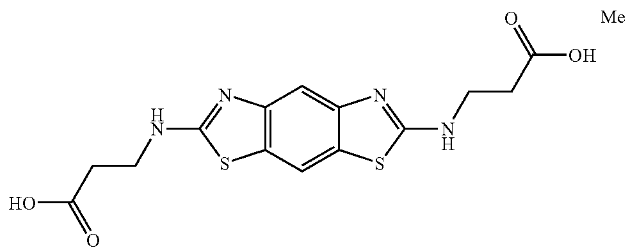 | Me | MeOH, KOH in H$_2$O, 70° C. | 0.2 | 367 |
| 26 | 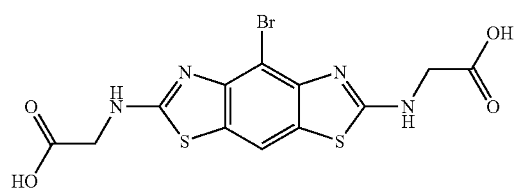 | Me | MeOH, NaOH in H$_2$O, RT | 0.43*[1] | 417/ 419 |
| 27 | 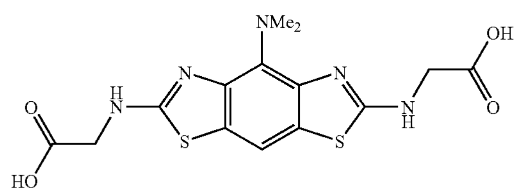 | Me | without solvent, NaOH in MeOH, RT | n.a. | n.a. |
| 28 | 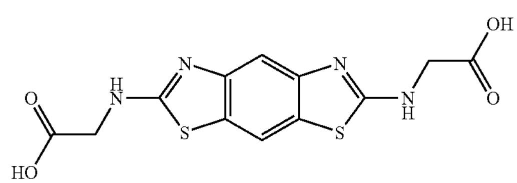 | Me | MeOH, KOH in H$_2$O, 70° C. | 0.2 | 339 |
| 29 | 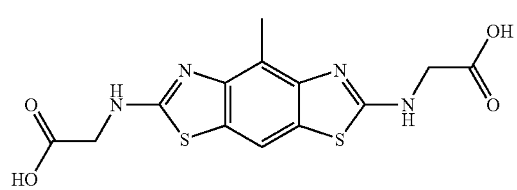 | Me | MeOH, NaOH in H$_2$O, RT | 0.2 | 353 |
| 30 | 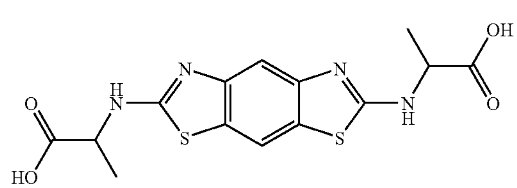 | Et | EtOH, NaOH in H$_2$O, 70° C. | 1.00 | 367 |

Example 31

Table 12 (Synthesis Scheme A)

Example 32

Table 12 (Synthesis Scheme D)

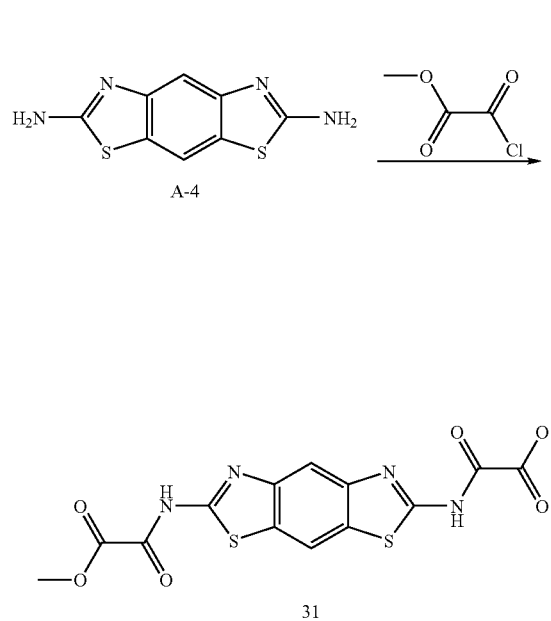

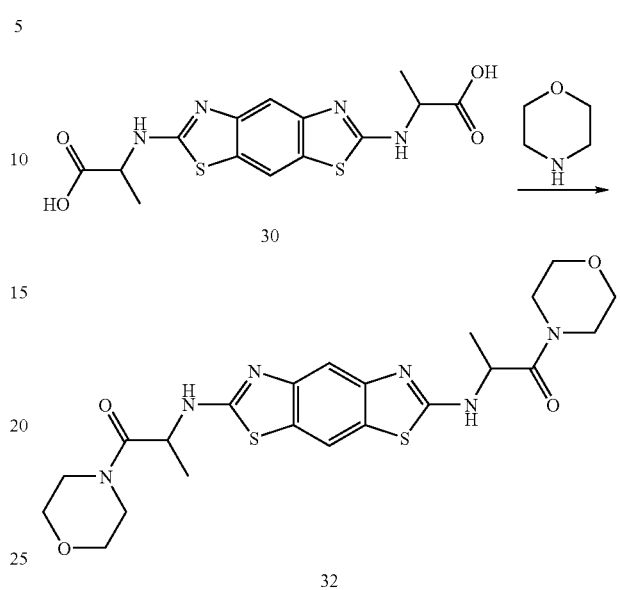

A solution of A-4 (300 mg, 1.35 mmol) in pyridine (326.8 µL, 4.05 mmol) and dry DCM (1 mL) is combined with methyl chloro-oxoacetate (372.4 µL, 4.05 mmol) and stirred for 5 min at RT. The precipitate is filtered off, washed with DCM and dried until a constant weight is obtained. The title compound 31 is obtained as a solid.

TBTU (131.4 mg, 0.409 mmol) is added to a suspension of 30 (50 mg, 0.136 mmol) in DMF (0.5 mL), pyridine (33 µL, 0.409 mmol) and morpholine (47.6 µL, 0.546 mmol) and stirred for 2 h at RT. Then the mixture is divided between EE and water and the organic phase is dried, evaporated down and chromatographed by RP-phase (eluant: ACN:H$_2$O; gradient: ACN:H$_2$O 5:95→95:5). The product-containing fractions are combined and freeze-dried. The title compound 32 is obtained as a solid.

TABLE 12

| # | Structure | $t_{Ret.}$ (HPLC) [min] | MS (ESI+) [M + H]$^+$ |
|---|---|---|---|
| 31 | 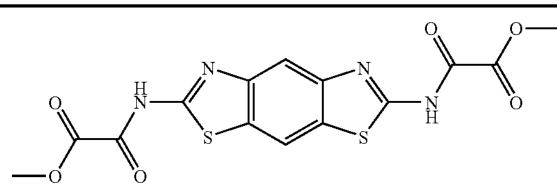 | 1.62 | 395 |
| 32 | 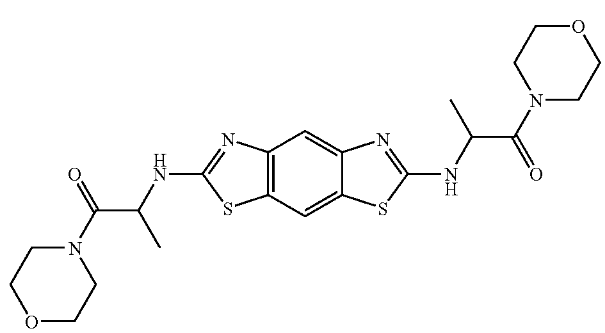 | 1.39 | 505 |

Example 33

Table 13 (Synthesis Scheme B)

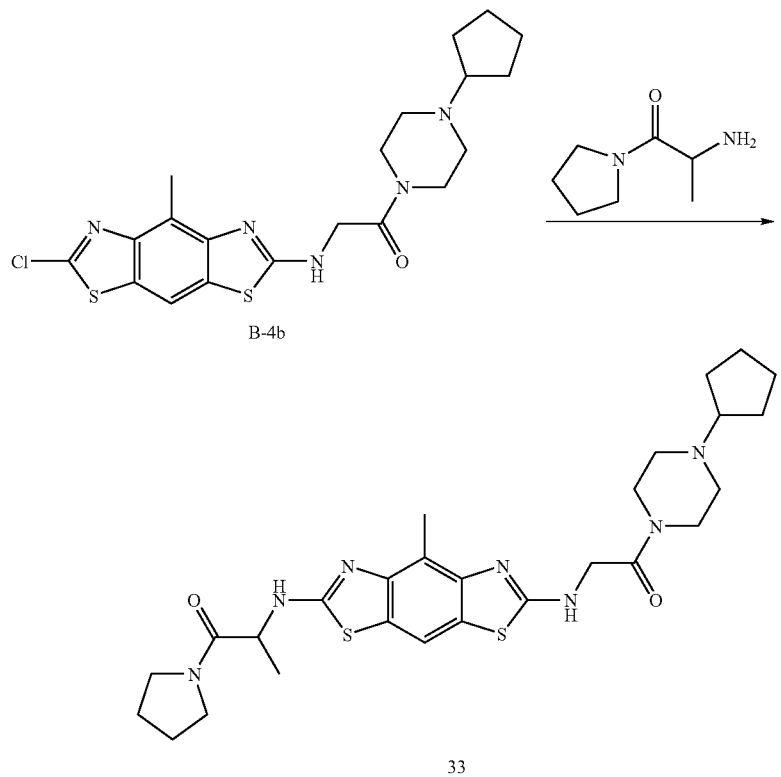

B-4-b (30 mg, 0.067 mmol) in NMP (0.5 mL) is combined with 2-amino-1-pyrrolidin-1-yl-propanone hydrochloride (36 mg, 0.202 mmol) and DIPEA (147 μL, 0.858 mmol) and stirred for 32 h at 110° C. After cooling to RT the reaction mixture is chromatographed by RP-phase (eluant: ACN/H$_2$O). The product-containing fractions are combined and freeze-dried. The title compound 33 is obtained as a solid.

Example 34-52 are prepared analogously or by obvious transformations from similar Examples. (Table 13)

TABLE 13

| # | Structure | t$_{Ret.}$ (HPLC) [min] | MS (ESI+) [M + H]$^+$ |
|---|---|---|---|
| 33 | 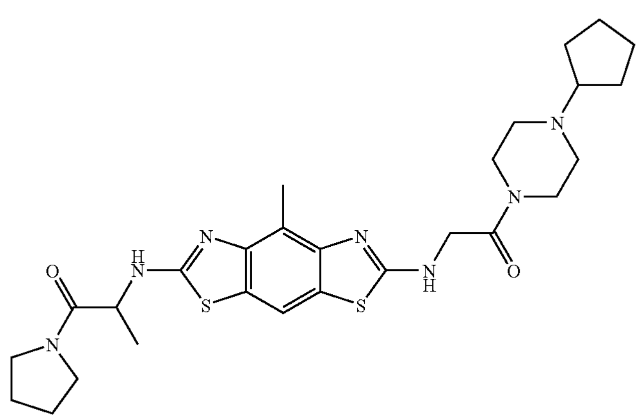 | 0.0 | 556 |

TABLE 13-continued

| # | Structure | t_Ref. (HPLC) [min] | MS (ESI+) [M + H]+ |
|---|---|---|---|
| 34 | 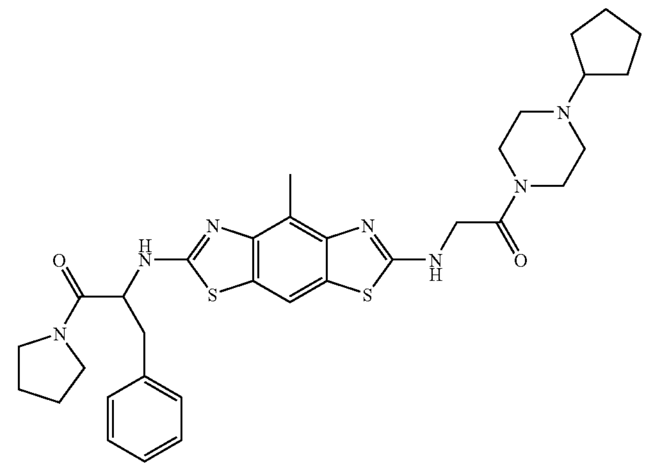 | 1.60 | 632 |
| 35 | 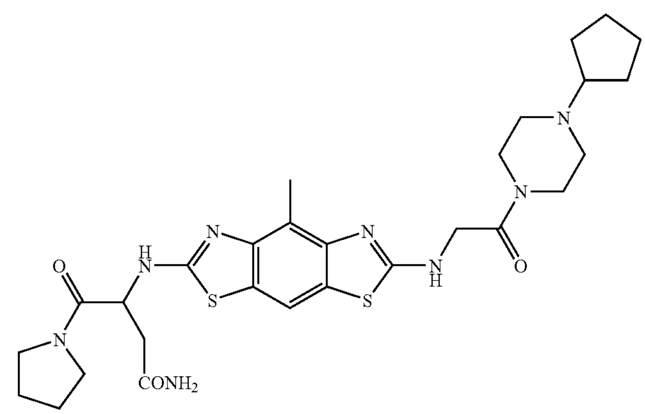 | 0.0 | 599 |
| 36 | 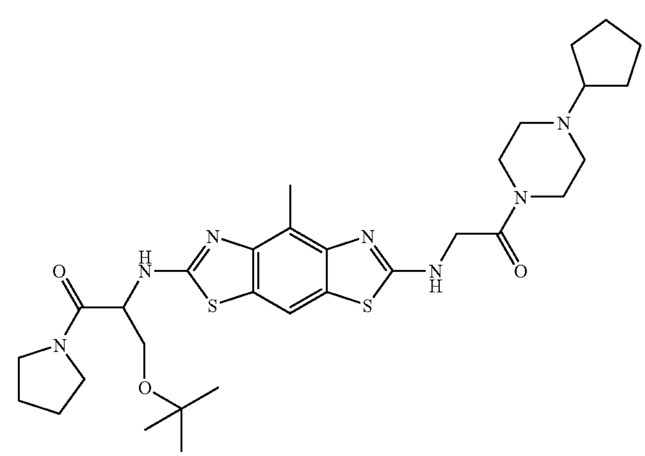 | 1.58 | 628 |

TABLE 13-continued
| # | Structure | $t_{Ret.}$ (HPLC) [min] | MS (ESI+) [M + H]$^+$ |
|---|---|---|---|
| 37 | 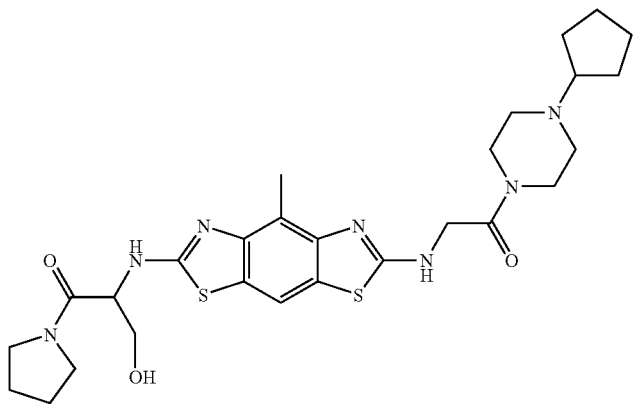 | 1.28 | 572 |
| 38 | 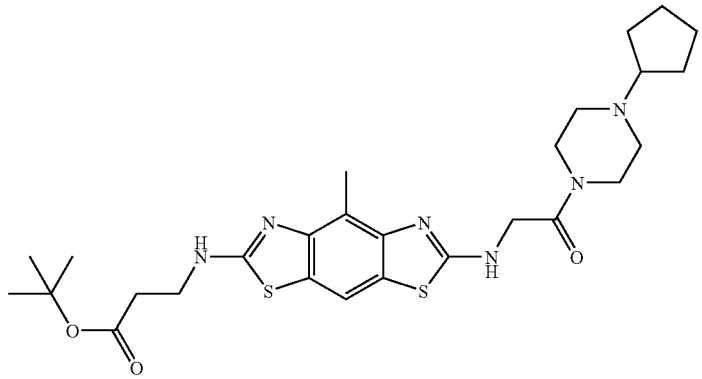 | 1.47 | 559 |
| 39 | 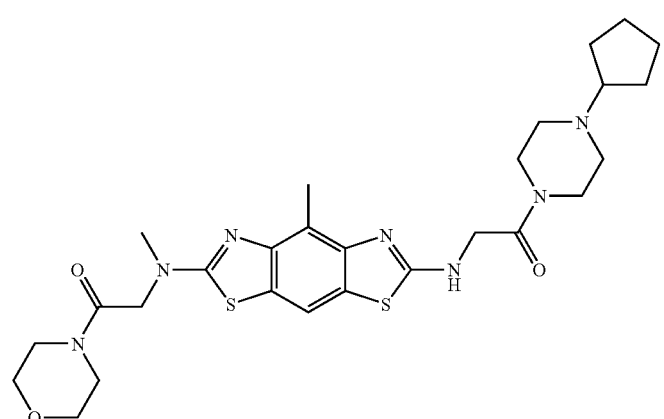 | 1.35 | 572 |

TABLE 13-continued

| # | Structure | $t_{Ret.}$ (HPLC) [min] | MS (ESI+) $[M + H]^+$ |
|---|---|---|---|
| 40 | 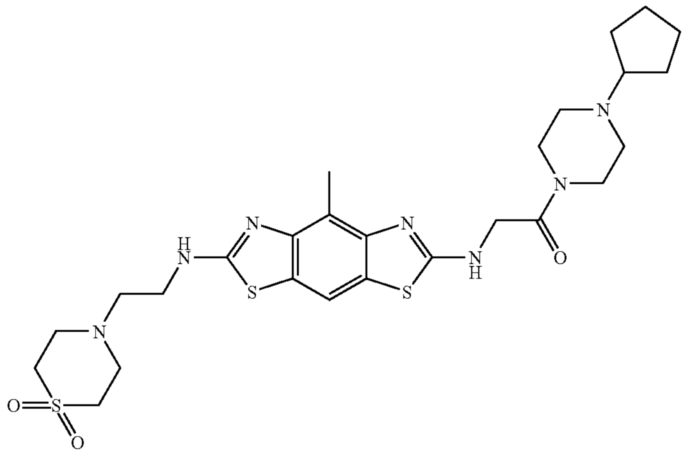 | 0.0 | 592 |
| 41 | 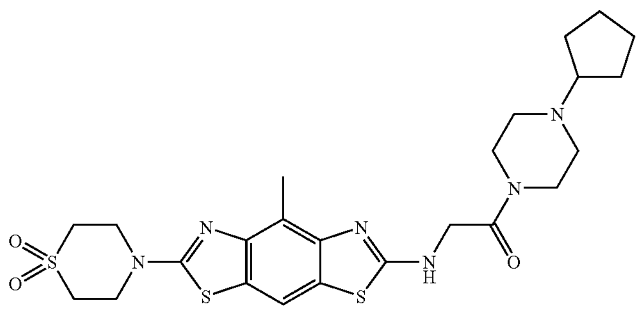 | n.v | n.a. |
| 42 | 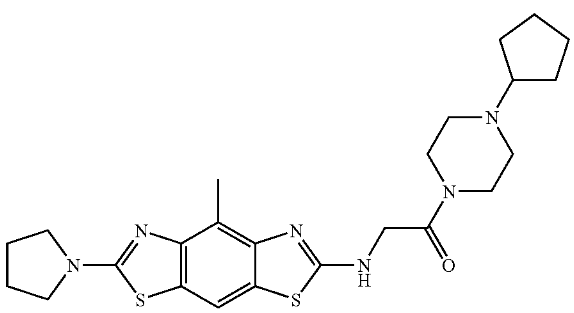 | 0.0 | 485 |
| 43 | 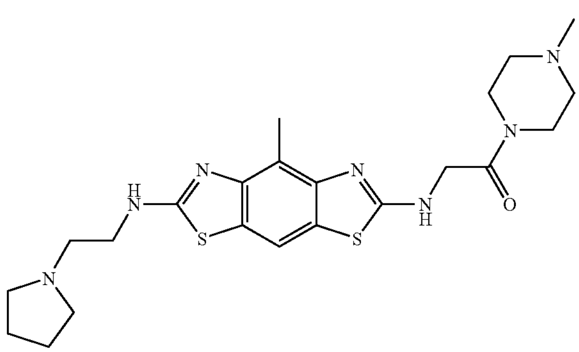 | 0.0 | 460 |

TABLE 13-continued
| # | Structure | t_Ret. (HPLC) [min] | MS (ESI+) [M + H]+ |
|---|---|---|---|
| 44 | 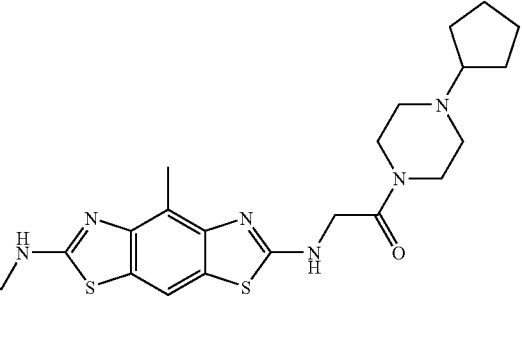 | 1.50 | 535 |
| 45 | 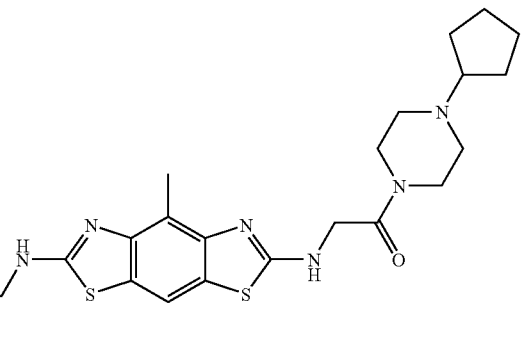 | 1.39 | 551 |
| 46 | 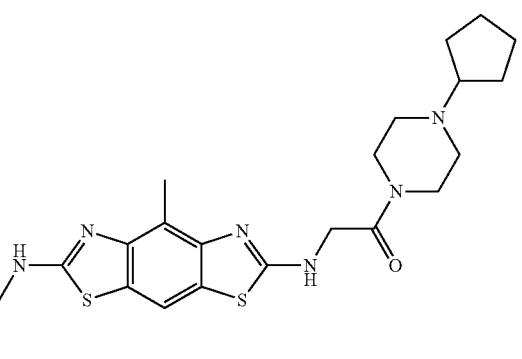 | 1.18 | 543 |
| 47 | 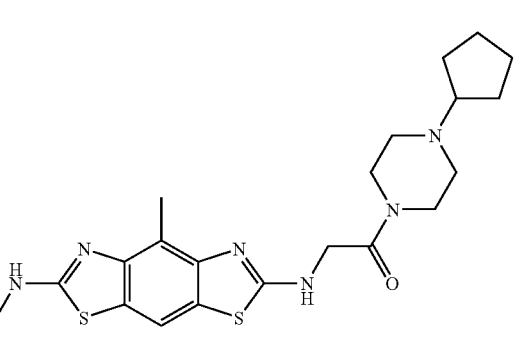 | 0.0 | 536 |

TABLE 13-continued

| # | Structure | $t_{Ret.}$ (HPLC) [min] | MS (ESI+) [M + H]$^+$ |
|---|---|---|---|
| 48 | 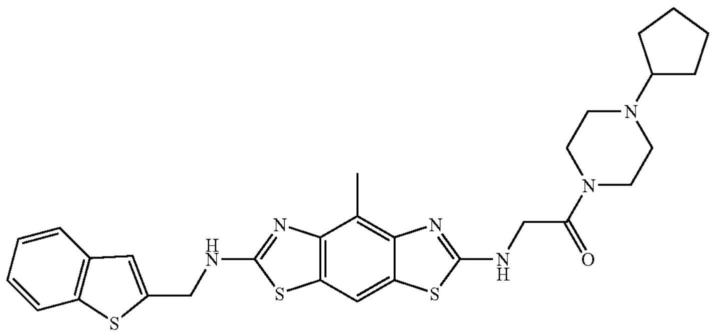 | 1.68 | 577 |
| 49 | 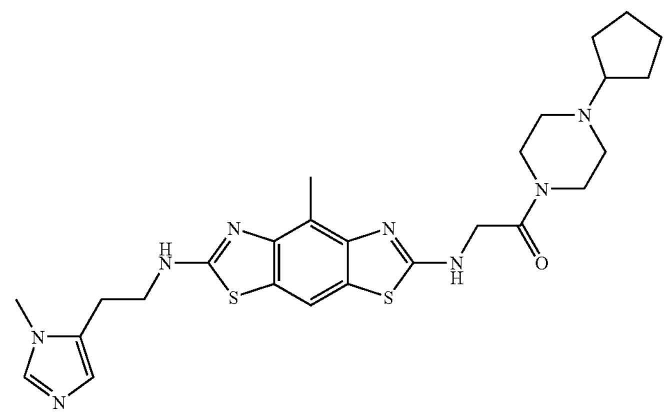 | 0.0 | 539 |
| 50 | 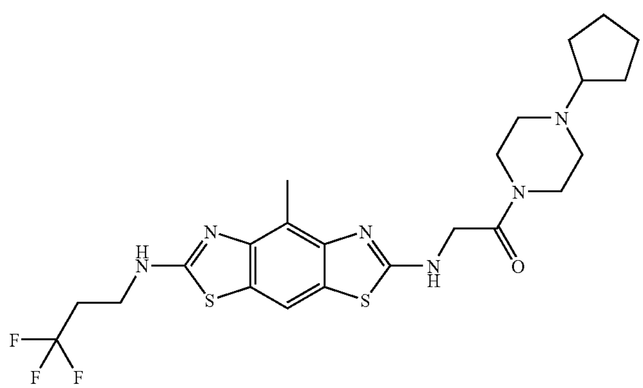 | 1.41 | 527 |
| 51 | 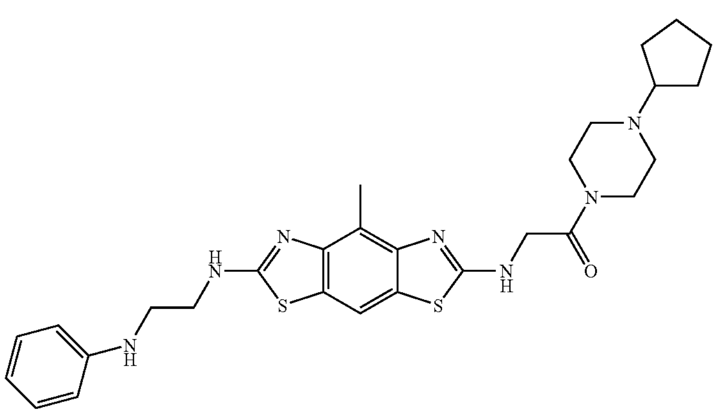 | 0.0 | 550 |

TABLE 13-continued

| # | Structure | $t_{Ret.}$ (HPLC) [min] | MS (ESI+) [M + H]$^+$ |
|---|---|---|---|
| 52 | 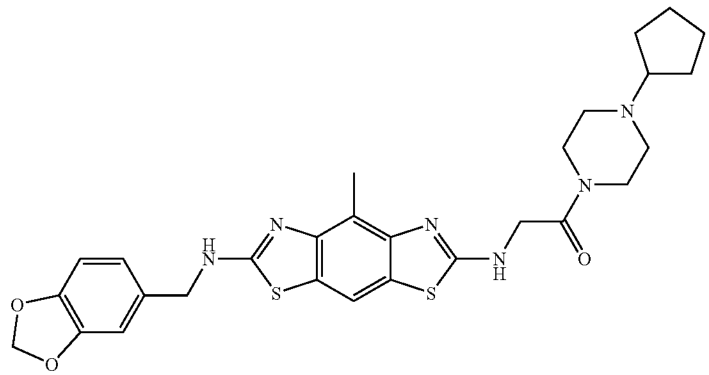 | 1.48 | 565 |

Example 53

Table 14 (Synthesis Scheme B)

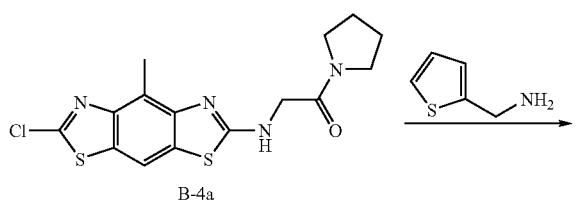

B-4-a (70 mg, 0.191 mmol) in dry NMP (50 µL) is combined with 2-thienyl-methylamine (44 mg, 0.389 mmol) and DIPEA (33 µL, 0.19 mmol) and stirred for 16 h at 110° C. After cooling to RT the reaction mixture is chromatographed by RP-phase (eluant: ACN/H$_2$O). The product-containing fractions are combined and freeze-dried. The title compound 53 is obtained as a solid.

Examples 54-57 are prepared analogously (Table 14)

TABLE 14

| # | Structure | $t_{Ret.}$ (HPLC) [min] | MS (ESI+) [M + H]$^+$ |
|---|---|---|---|
| 53 | 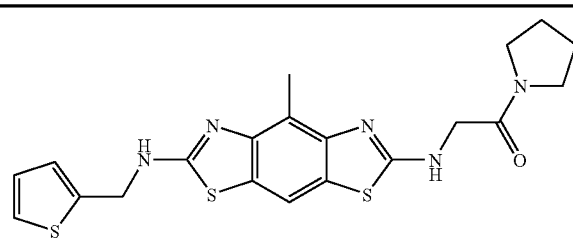 | 1.90 | 444 |
| 54 | 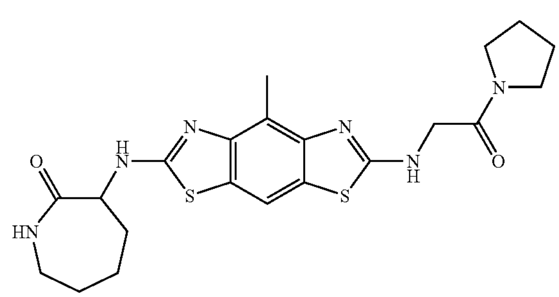 | 1.67 | 459 |

TABLE 14-continued
| # | Structure | t$_{Ret.}$ (HPLC) [min] | MS (ESI+) [M + H]$^+$ |
|---|---|---|---|
| 55 | 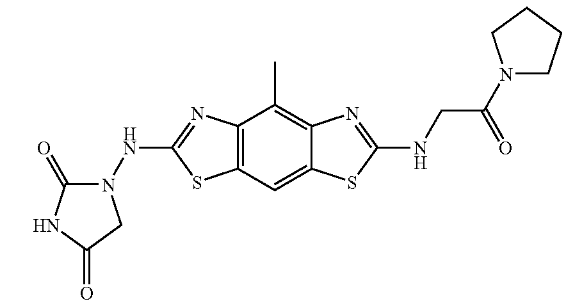 | 1.53 | 446 |
| 56 | 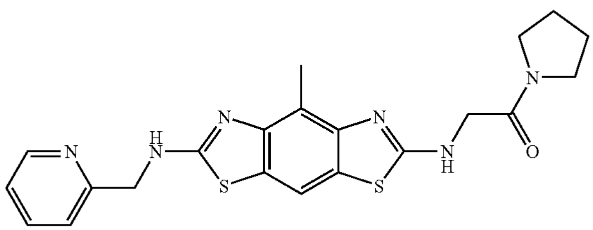 | 1.35 | 439 |
| 57 | 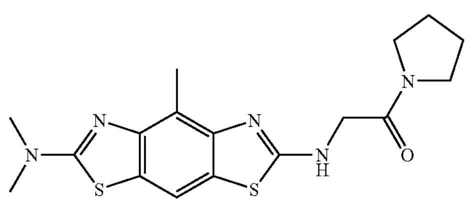 | 1.67 | 376 |
Example 58
Table 15 (Synthesis Scheme B)
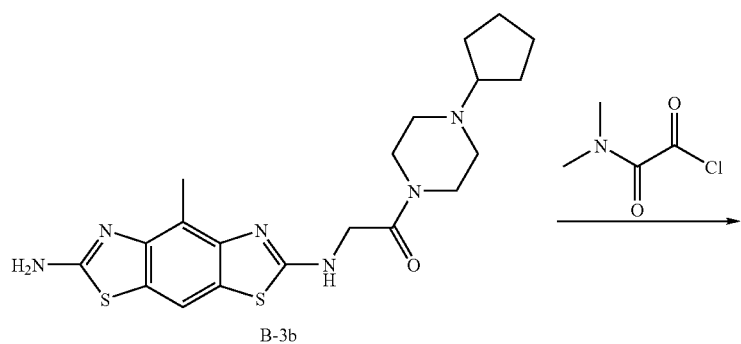
B-3b -continued

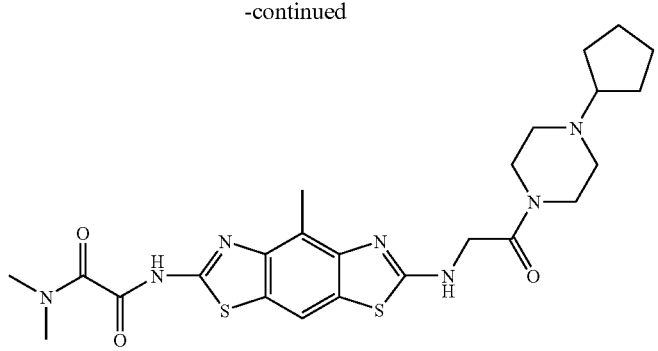

58

A solution of B-3b (35 mg, 0.081 mmol) in dry NMP (500 µL) and DIPEA (17 µL, 0.098 mmol) is combined with dimethylamino-oxo-acetyl chloride (13.2 mg, 0.098 mmol) and stirred for 30 min at RT. Then the reaction mixture is chromatographed by RP-phase (eluant: ACN/H$_2$O). The product-containing fractions are combined and freeze-dried. The title compound 58 is obtained as a solid.

Examples 59-66 are prepared analogously (Table 15)

TABLE 15

| # | Structure | $t_{Ret.}$ (HPLC) [min] | MS (ESI+) [M + H]$^+$ |
|---|-----------|-------------------------|------------------------|
| 58 | 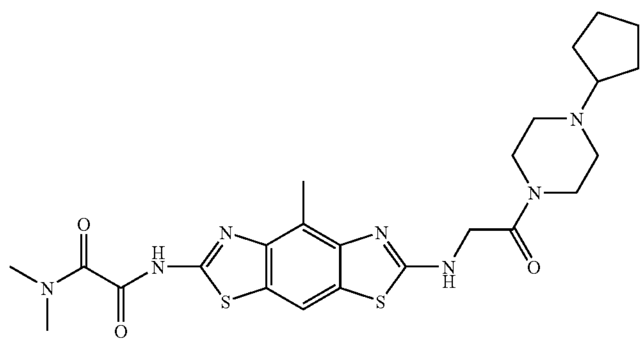 | 1.44 | 530 |
| 59 | 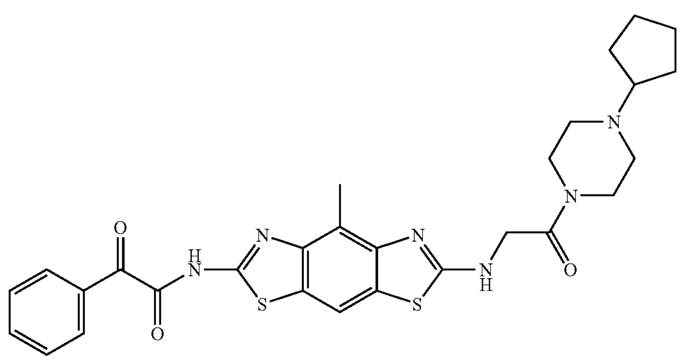 | 1.74 | 563 |
| 60 | 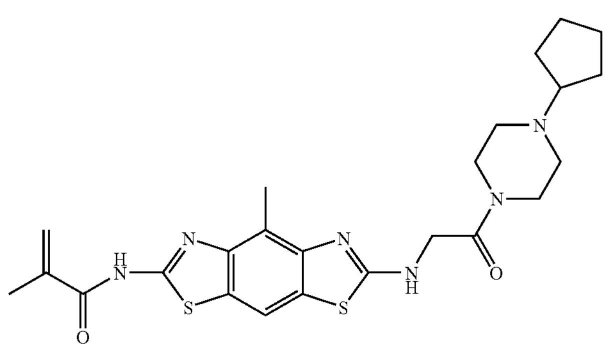 | 1.53 | 499 |

TABLE 15-continued

| # | Structure | $t_{Ret.}$ (HPLC) [min] | MS (ESI+) [M + H]+ |
|---|---|---|---|
| 61 | 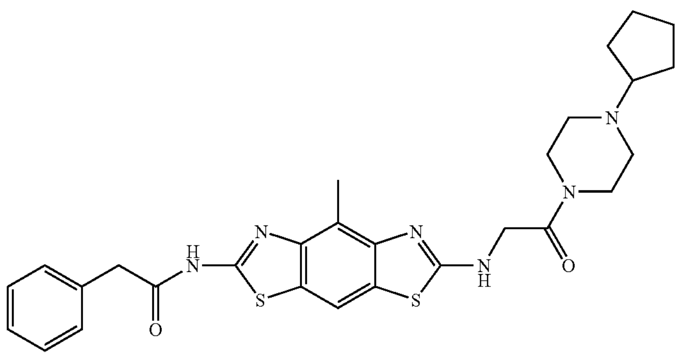 | 1.62 | 549 |
| 62 | 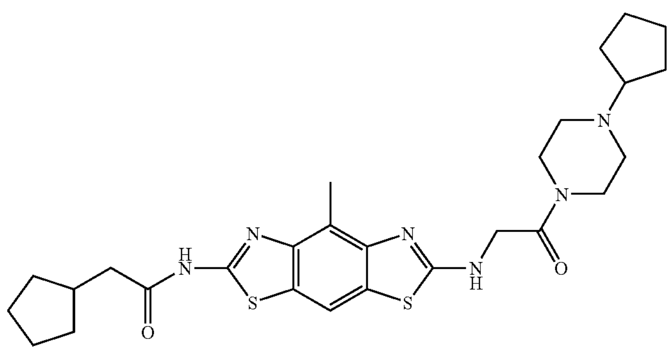 | 1.71 | 541 |
| 63 | 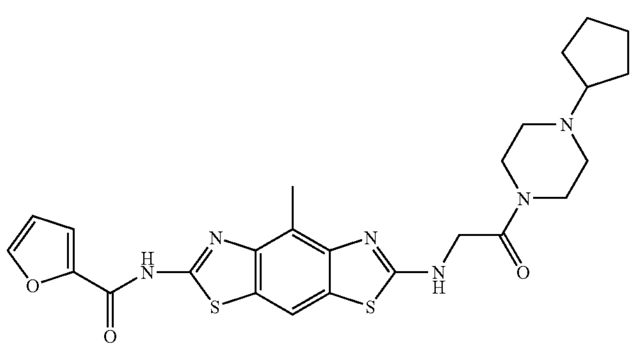 | 1.49 | 525 |
| 64 | 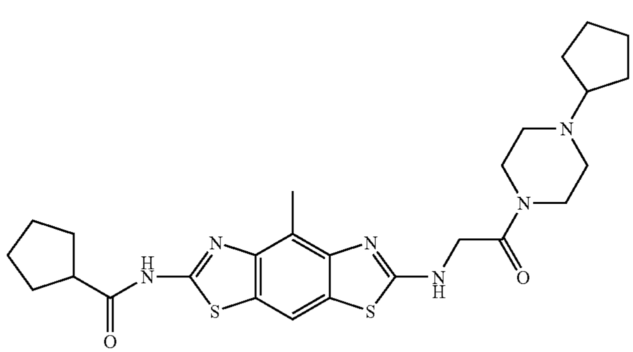 | 1.63 | 527 |

TABLE 15-continued

| # | Structure | $t_{Ret.}$ (HPLC) [min] | MS (ESI+) $[M + H]^+$ |
|---|---|---|---|
| 65 | 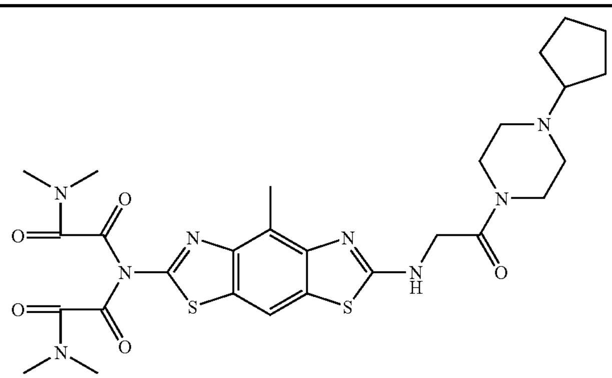 | 1.59 | 629 |
| 66 | 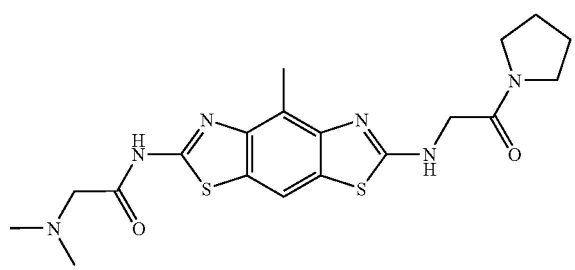 | 0.0 | 433 |

Example 67

Table 16 (Synthesis Scheme B)

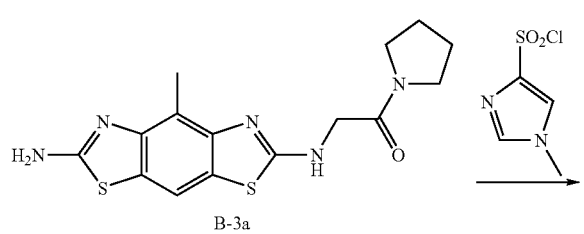

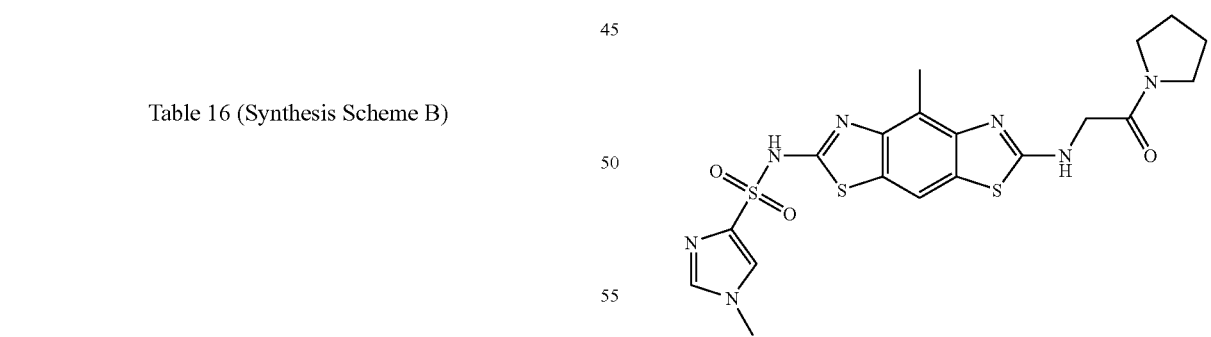

A solution of B-3a (50 mg, 0.144 mmol) in dry pyridine (200 µL, 2.453 mmol) is combined with 1-methylimidazol-4-sulphonyl chloride (82 mg, 0.431 mmol) and stirred for 12 h at 70° C. Then the reaction mixture is chromatographed by RP-phase (eluant: ACN/$H_2O$). The product-containing fractions are combined and freeze-dried. The title compound 67 is obtained as a solid.

Examples 68-71 are prepared analogously (Table 16)

TABLE 16

| # | Structure | $t_{Ret.}$ (HPLC) [min] | MS (ESI+) [M + H]$^+$ |
|---|---|---|---|
| 67 | 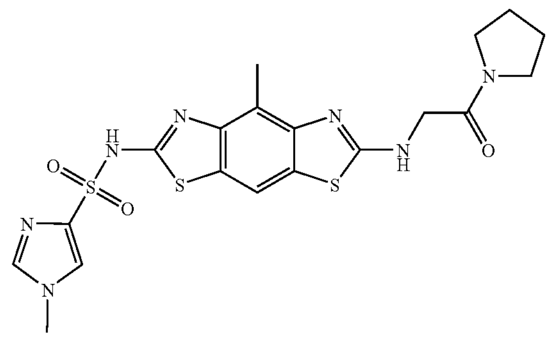 | 1.56 | 492 |
| 68 | 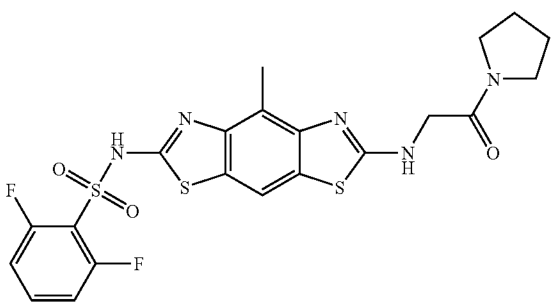 | 1.92 | 524 |
| 69 | 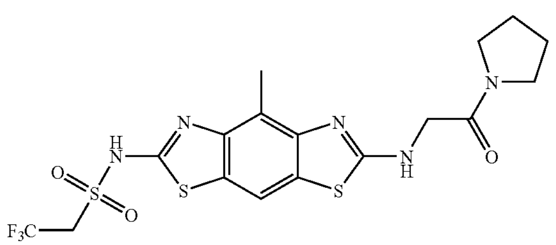 | 1.86 | 494 |
| 70 | 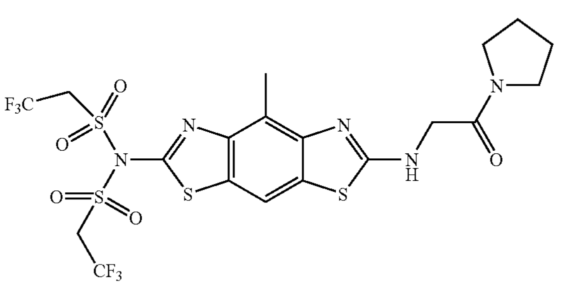 | 2.22 | 640 |
| 71 | 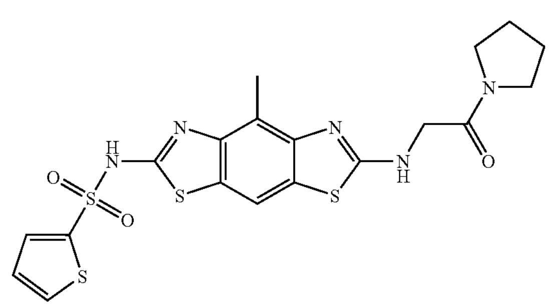 | 1.88 | 494 |

Example 72

Synthesis Scheme B

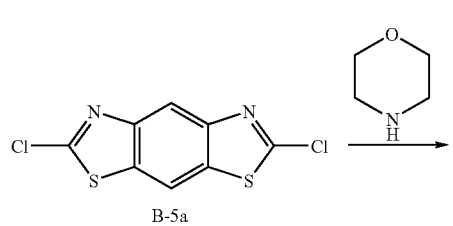

B-5a

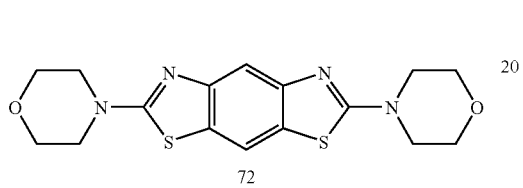

72

A solution of B-5a (50 mg, 0.191 mmol) in dry NMP (500 µL) is combined with morpholine (84 µL, 0.764 mmol) and stirred for 10 min at 170° C. (microwave). Then the reaction mixture is chromatographed by RP-phase (eluant: ACN/ H$_2$O). The product-containing fractions are combined and freeze-dried. The title compound 72 is obtained as a solid. (HPLC t$_{Ret.}$=1.68 min; MS [M+H]$^+$: m/z=363)

General Method for Synthesising the Examples 73-75 (Synthesis Scheme A):

A-3 x-z 73-75

2.1-2.2 eq bromine in the form of a bromine solution (approx. 1 M in chloroform) are in each case slowly added dropwise at RT to a solution of the corresponding bisthiourea A-3 x-z in chloroform or acetonitrile. Once it has been established that the reaction is complete the solvents are eliminated in vacuo and the product is obtained, which is optionally purified by chromatography.

TABLE 17

| # | Structure | t$_{Ret.}$ (HPLC) [min] | MS (ESI+) [M + H]$^+$ |
|---|-----------|-------------------------|------------------------|
| 73 | 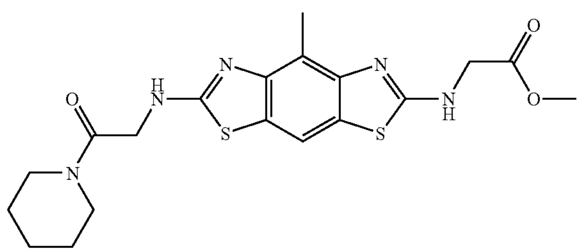 | 1.67 | 434 |
| 74 | 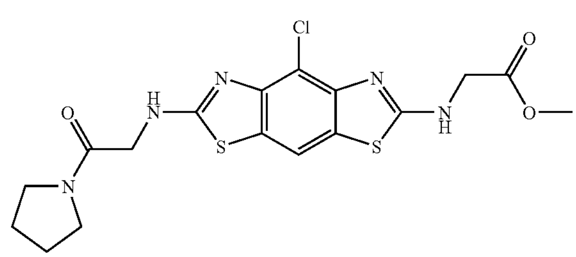 | 0.87*[1] | 440. |

TABLE 17-continued

| # | Structure | $t_{Ret.}$ (HPLC) [min] | MS (ESI+) [M + H]$^+$ |
|---|---|---|---|
| 75 | 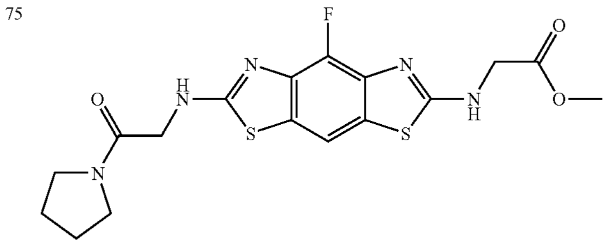 | 1.66 | 424 |

General Method for Synthesising Examples 76-78 (Synthesis Scheme C):

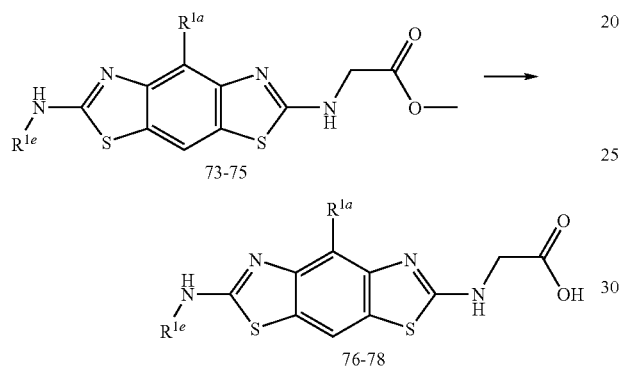

A solution of the corresponding ester 73-75 is stirred at RT under the conditions specified. Once the reaction is complete the solvents are eliminated in vacuo and the product is optionally purified by chromatography.

TABLE 18

| # | Structure | conditions | $t_{Ret.}$ (HPLC) [min] | MS (ESI+) [M + H]$^+$ |
|---|---|---|---|---|
| 76 | 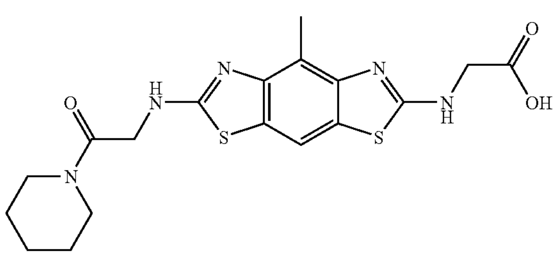 | 1 M NaOH in MeOH | 1.48 | 420 |
| 77 | 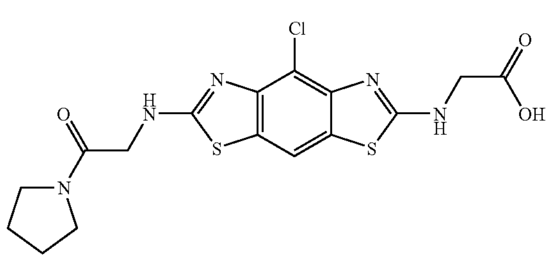 | 1 M KOH in MeOH | 0.71*[1] | 426 |

TABLE 18-continued

| # | Structure | conditions | $t_{Ret.}$ (HPLC) [min] | MS (ESI+) [M + H]$^+$ |
|---|---|---|---|---|
| 78 | 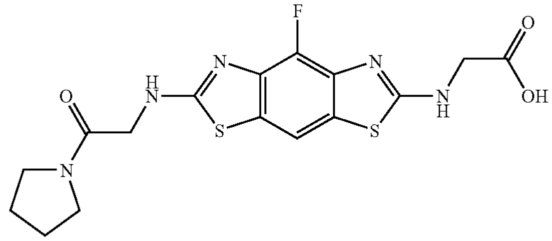 | 1 M NaOH in MeOH | 1.53 | 410 |

General Method for Synthesising Examples 79-81 (Synthesis Scheme A or C):

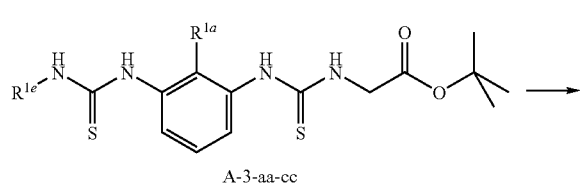

A-3-aa-cc

-continued

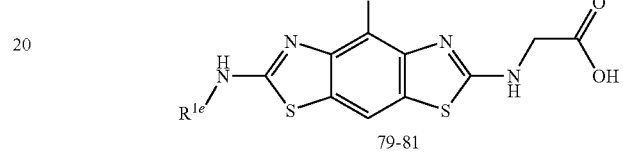

79-81

2.1-2.2 eq bromine in the form of a solution in chloroform are slowly added dropwise at RT to a solution of the corresponding bisthiourea A-3 aa-ac in chloroform or acetonitrile. Once it has been established that the reaction is complete the solvents are eliminated in vacuo and the product is isolated by chromatography.

TABLE 19

| # | Structure | $t_{Ret.}$ (HPLC) [min] | MS (ESI+) [M + H]$^+$ |
|---|---|---|---|
| 79 | 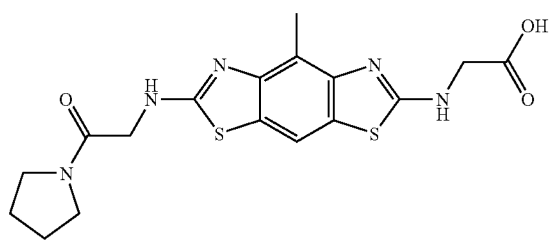 | 1.43 | 406 |
| 80 | 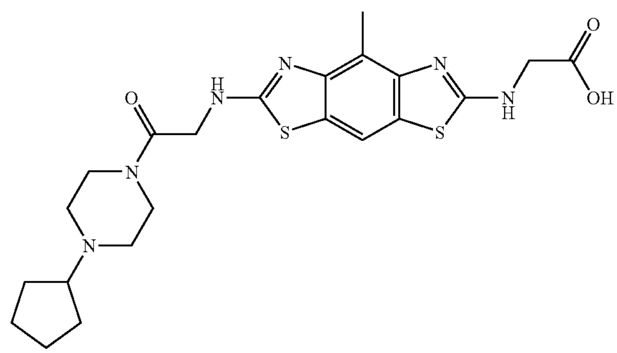 | 0.0 | 489 |

TABLE 19-continued

| # | Structure | $t_{Ret.}$ (HPLC) [min] | MS (ESI+) $[M + H]^+$ |
|---|-----------|---------------------|---------------------|
| 81 | 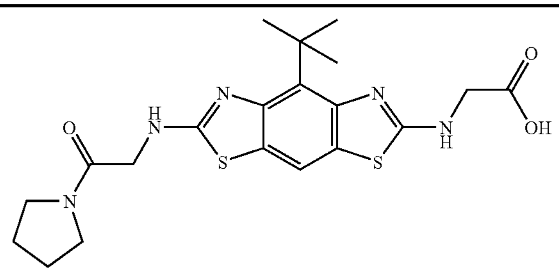 | 1.87 | n.a. |

Example 82

Table 20 (Synthesis Scheme C)

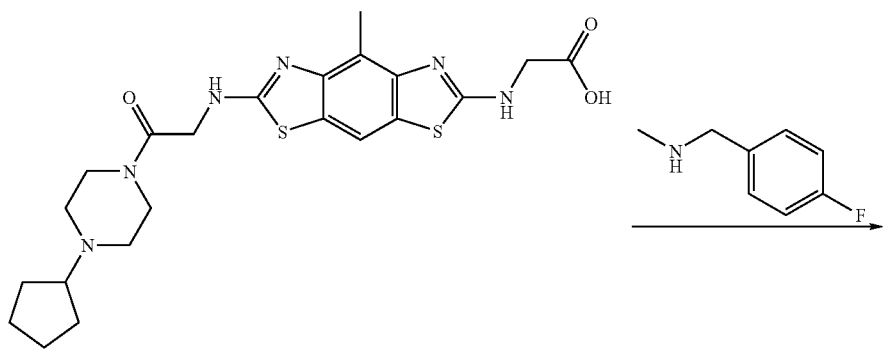

80

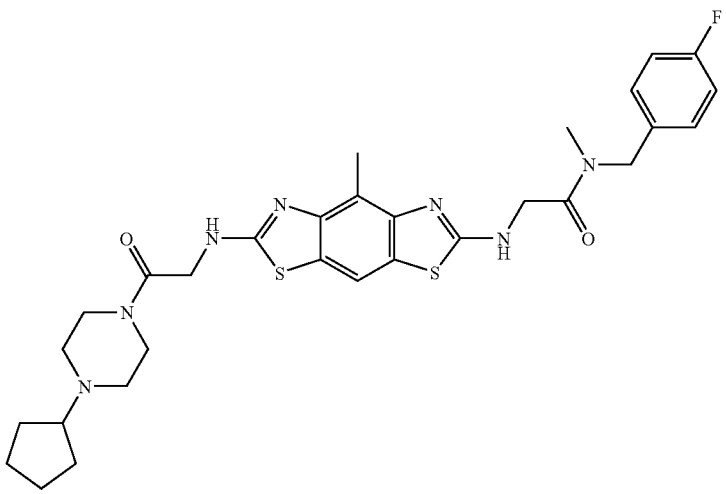

82

1.5 eq TBTU, 6 eq DIPEA and 1.5 eq N-(4-fluorobenzyl)-methylamine are added to 80 (68 mg; 140 μmol) in 0.4 mL NMP and the mixture is stirred at RT. After the reaction is complete the solvent is eliminated in vacuo and the product is isolated by chromatography.

Examples 83-147 are prepared analogously, for example from the carboxylic acids in Tables 18 and 19, or obtained by obvious transformations from similar Examples.

TABLE 20

| # | Structure | t_Ret. (HPLC) [min] | MS (ESI+) [M + H]+ |
|---|---|---|---|
| 82 | 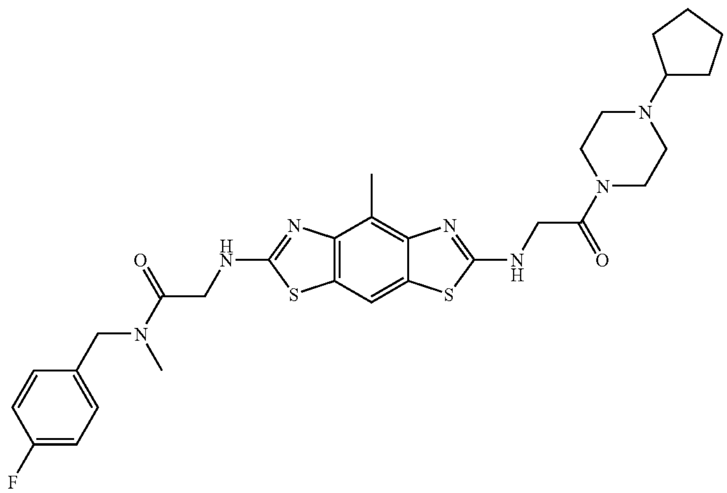 | 1.50 | 610 |
| 83 | 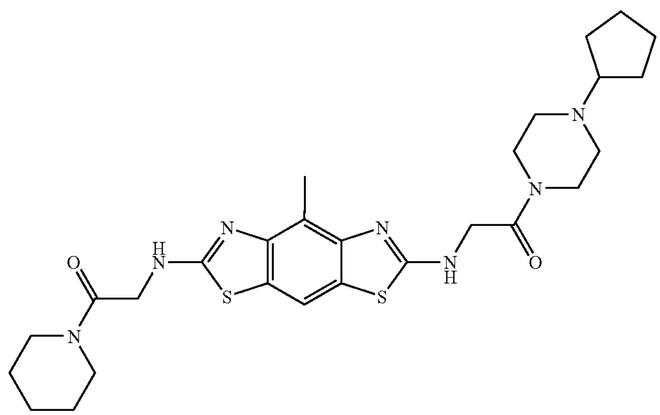 | 1.34 | 556 |
| 84 | 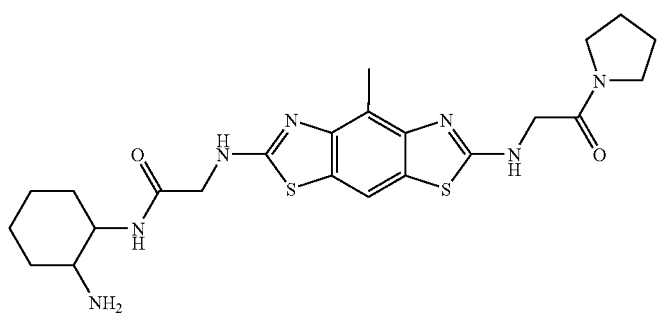 | 1.33 | 502 |
| 85 | 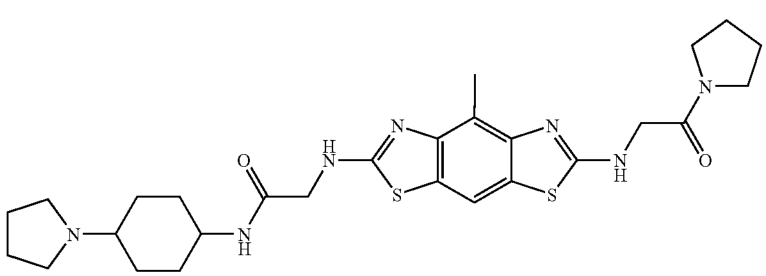 | 1.28 | 556 |

TABLE 20-continued

| # | Structure | $t_{Ret.}$ (HPLC) [min] | MS (ESI+) $[M + H]^+$ |
|---|---|---|---|
| 86 | 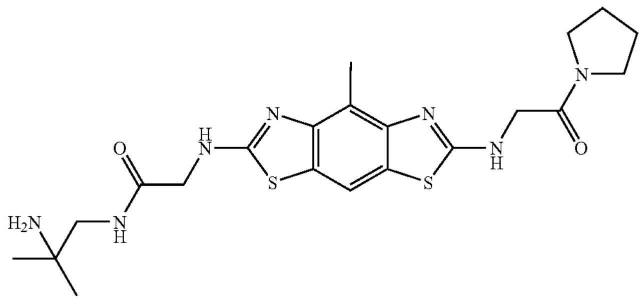 | 1.25 | 476 |
| 87 | 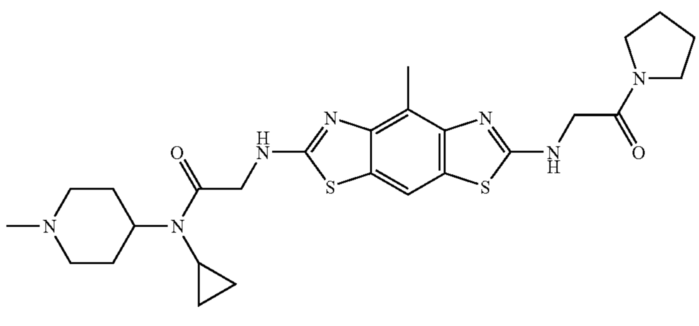 | 1.38 | 542 |
| 88 | 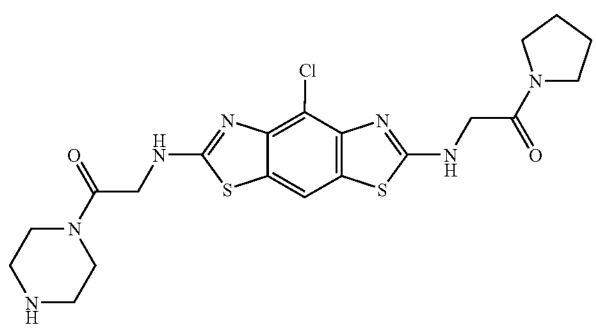 | 1.23 | 494 |
| 89 | 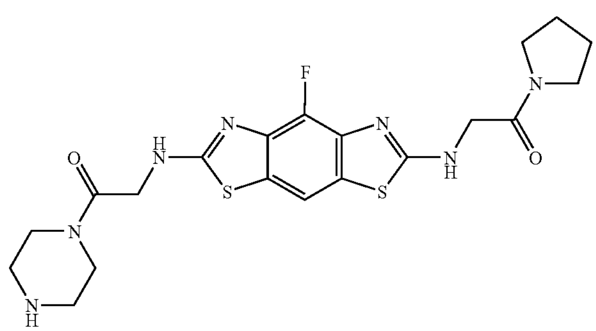 | 0.0 | 478 |

TABLE 20-continued
| # | Structure | t_Ret. (HPLC) [min] | MS (ESI+) [M + H]+ |
|---|---|---|---|
| 90 | 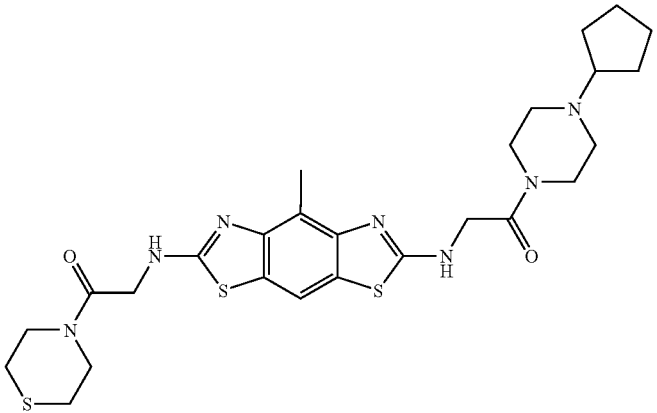 | 1.30 | 574 |
| 91 | 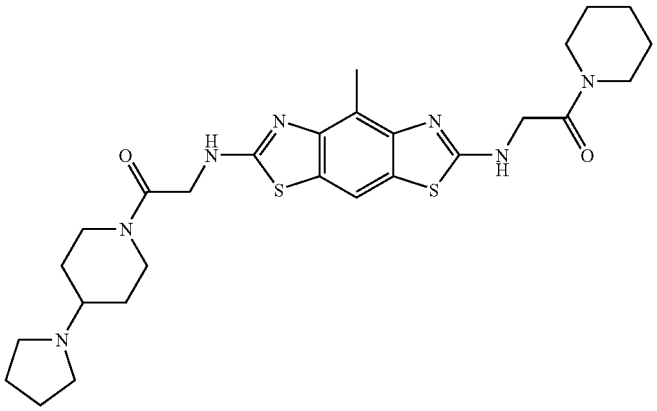 | 1.35 | 556 |
| 92 | 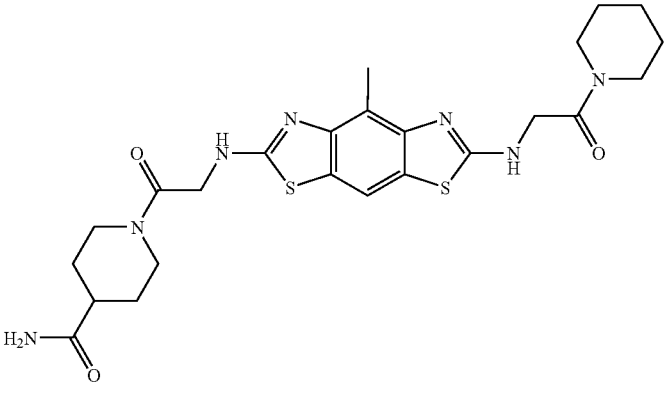 | 1.46 | 530 |

TABLE 20-continued

| # | Structure | t_Ret. (HPLC) [min] | MS (ESI+) [M + H]+ |
|---|---|---|---|
| 93 | 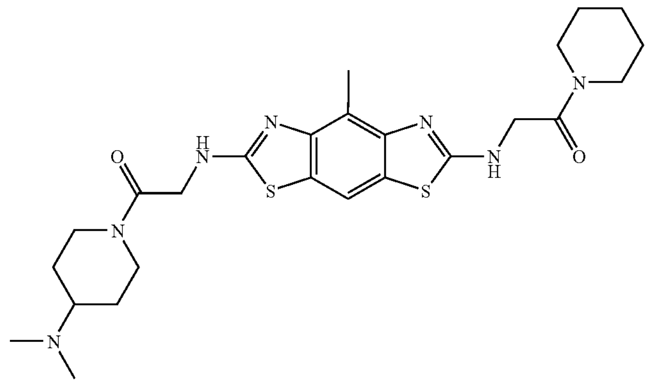 | 0.0 | 530 |
| 94 | 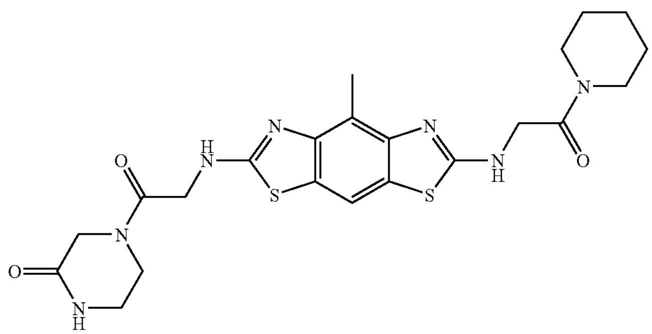 | 1.42 | 502 |
| 95 | 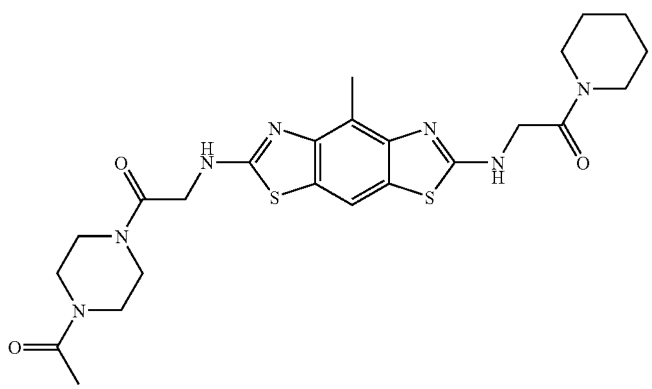 | 1.52 | 530 |
| 96 | 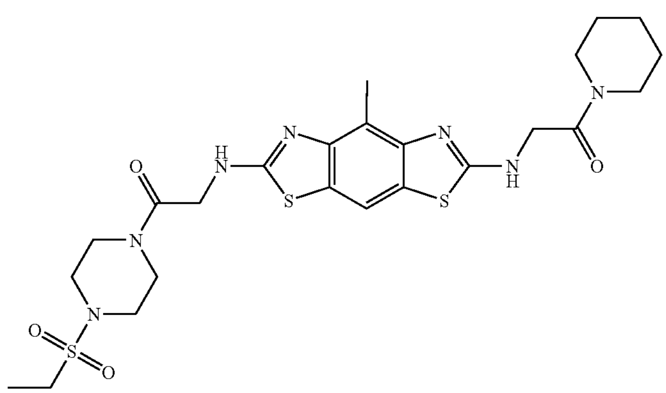 | 1.65 | 580 |

TABLE 20-continued

| # | Structure | $t_{Ret.}$ (HPLC) [min] | MS (ESI+) $[M + H]^+$ |
|---|---|---|---|
| 97 | 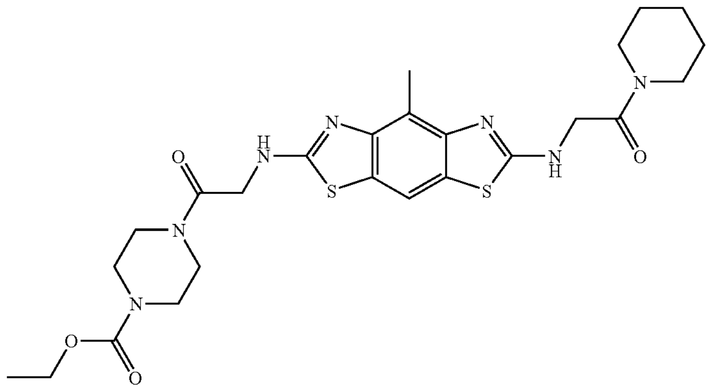 | 1.73 | 560 |
| 98 | 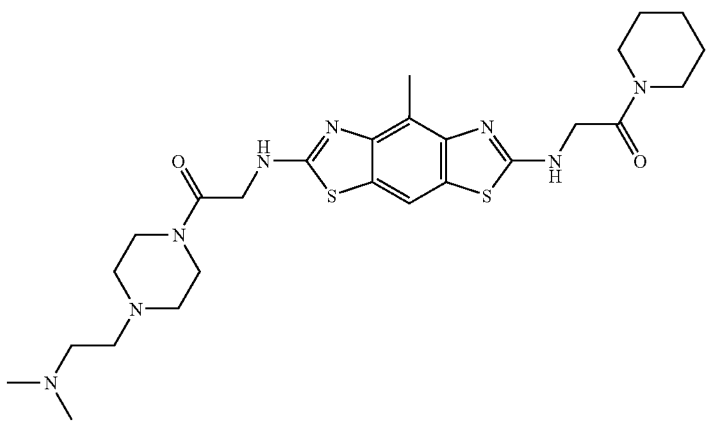 | 1.31 | 559 |
| 99 | 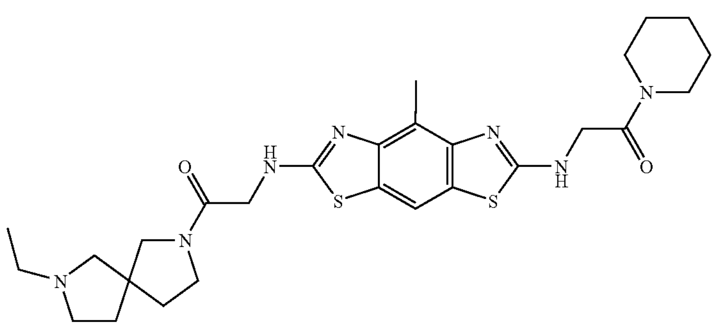 | 1.36 | 556 |
| 100 | 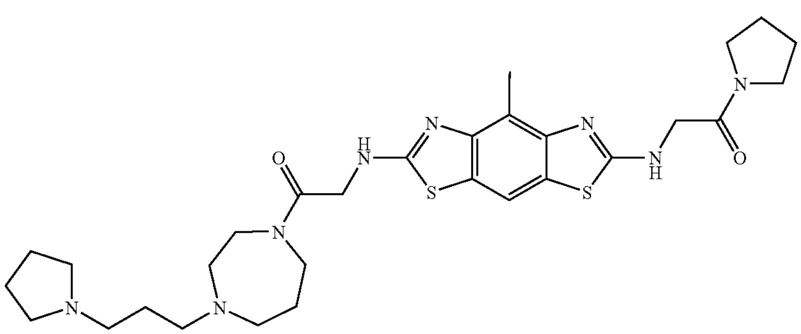 | 0.0 | 599 |

TABLE 20-continued

| # | Structure | t_Ret. (HPLC) [min] | MS (ESI+) [M + H]+ |
|---|---|---|---|
| 101 | 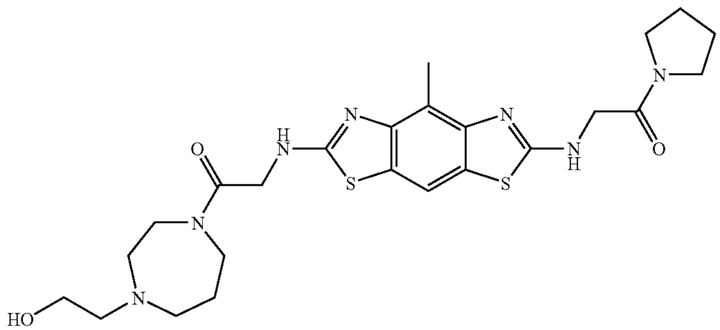 | 0.0 | 532 |
| 102 | 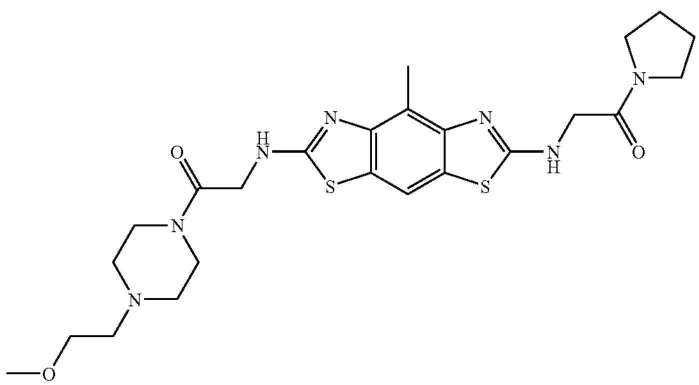 | 0.0 | 532 |
| 103 | 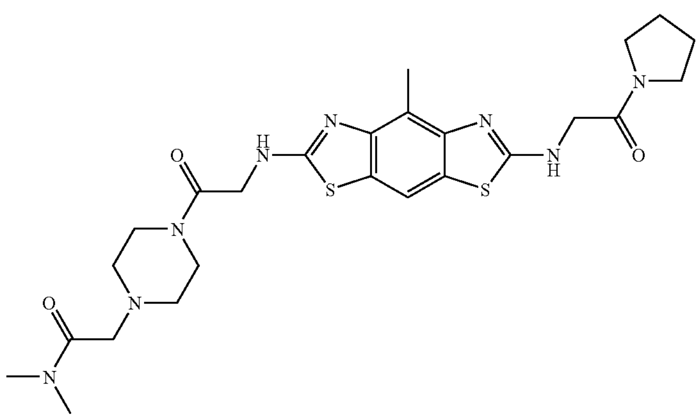 | 0.0 | 559 |
| 104 | 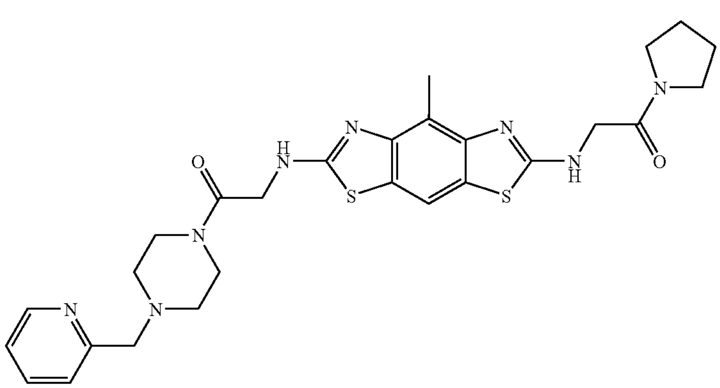 | 1.26 | 565 |

TABLE 20-continued

| # | Structure | t$_{Ret.}$ (HPLC) [min] | MS (ESI+) [M + H]$^+$ |
|---|---|---|---|
| 105 | 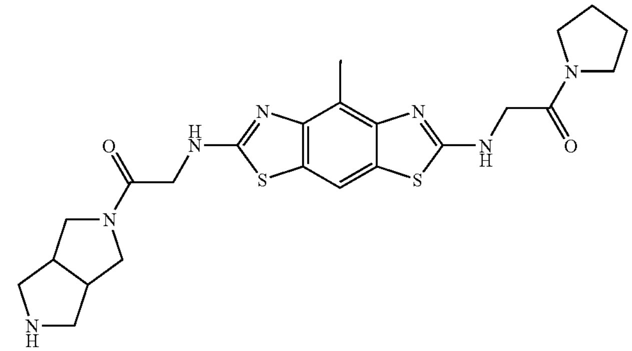 | 0.0 | 500 |
| 106 | 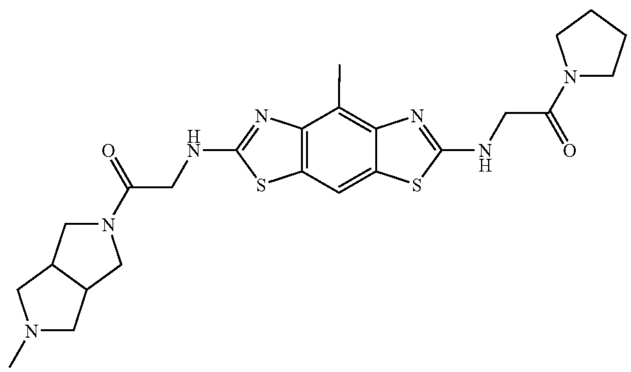 | 0.0*4 | 514 |
| 107 | 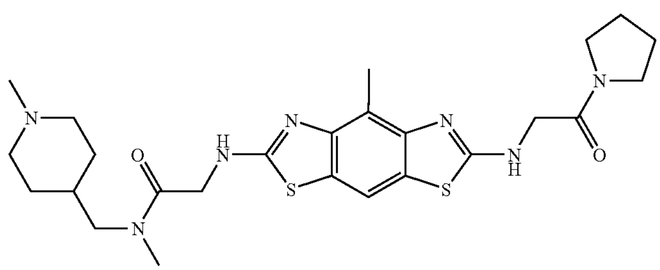 | 1.30 | 530 |
| 108 | 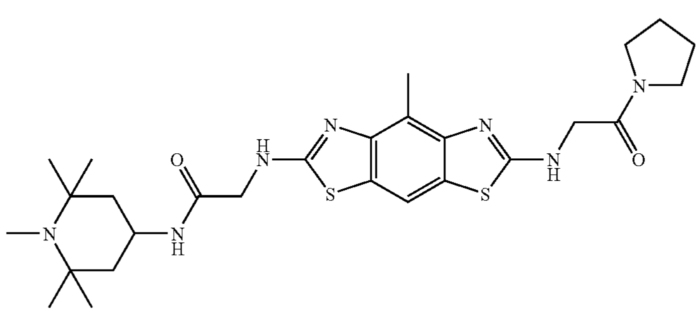 | 0.0 | 558 |

TABLE 20-continued
| # | Structure | t_Ret. (HPLC) [min] | MS (ESI+) [M + H]+ |
|---|---|---|---|
| 109 | 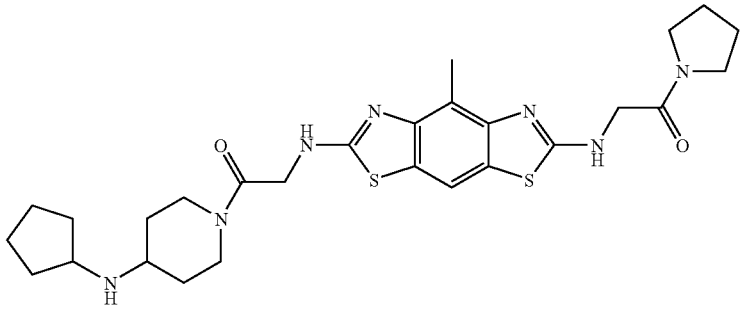 | 1.33 | 556 |
| 110 | 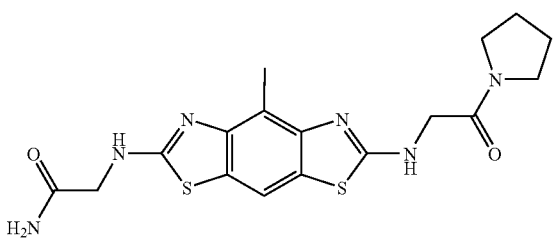 | 0.0 | 405 |
| 111 | 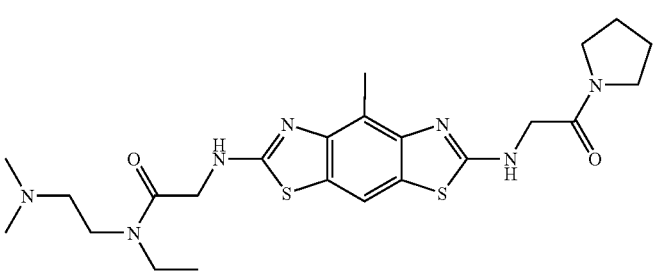 | 0.0 | 504 |
| 112 | 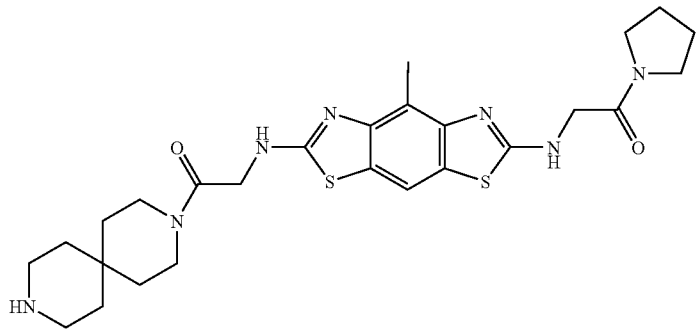 | 1.25 | 542 |
| 113 | 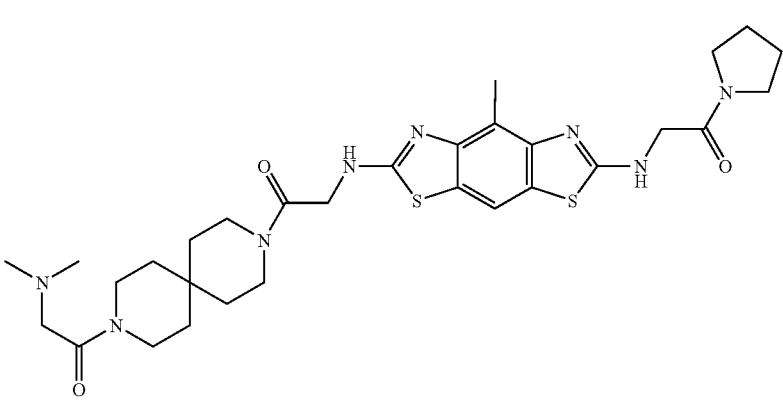 | 0.0 | 627 |

TABLE 20-continued

| # | Structure | t_Ret. (HPLC) [min] | MS (ESI+) [M + H]+ |
|---|---|---|---|
| 114 | 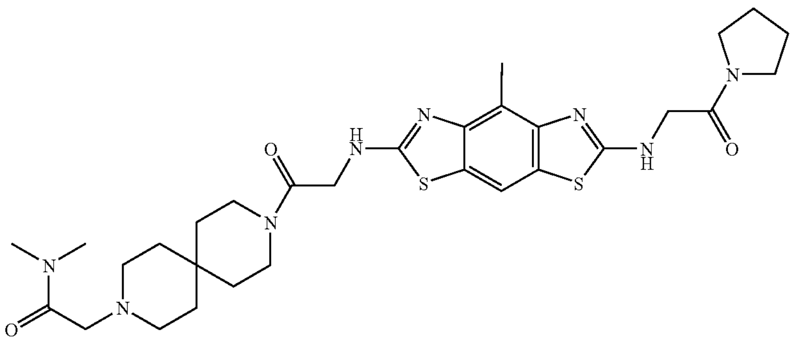 | 0.0 | 627 |
| 115 | 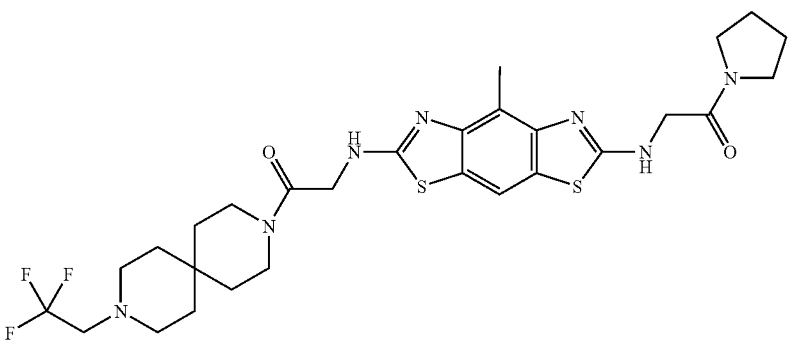 | 1.67 | 624 |
| 116 | 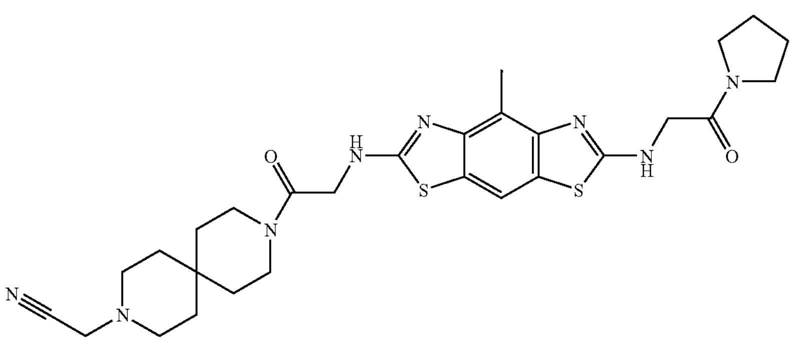 | 1.57 | 581 |
| 117 | 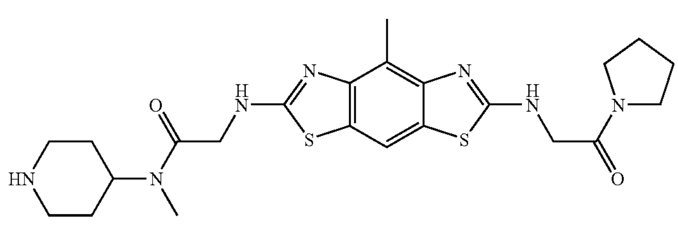 | n.a. | 502 |
| 118 | 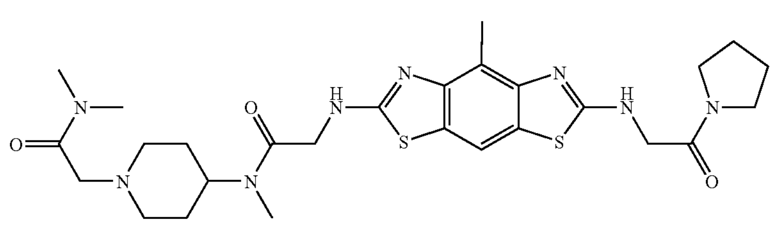 | 0.0 | 587 |

TABLE 20-continued
| # | Structure | t_Ret. (HPLC) [min] | MS (ESI+) [M + H]+ |
|---|---|---|---|
| 119 | 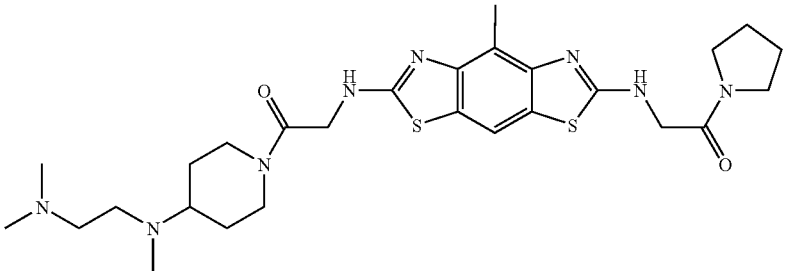 | 0.0 | 573 |
| 120 | 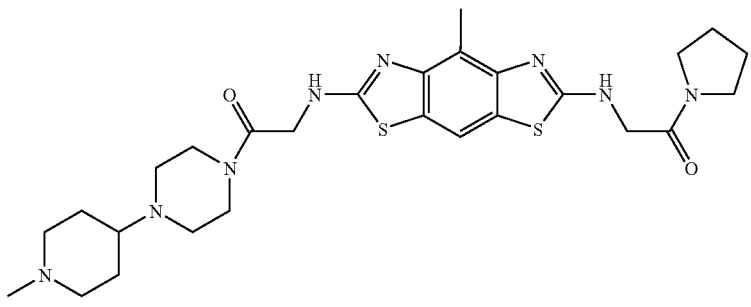 | 0.0 | 571 |
| 121 | 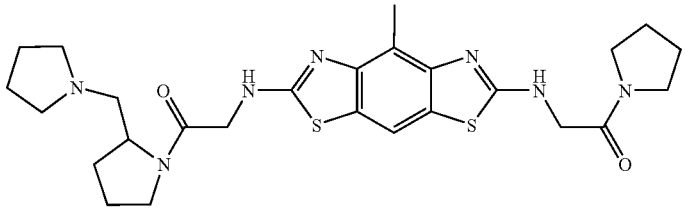 | 1.34 | 542 |
| 122 | 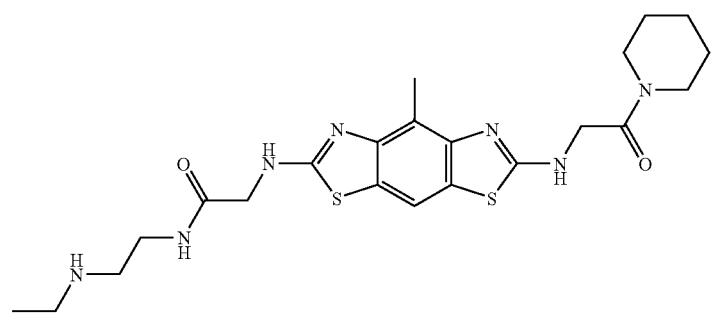 | 1.28 | 490 |
| 123 | 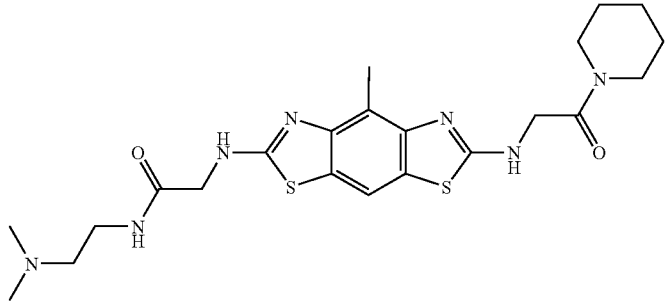 | 0.0 | 490 |

TABLE 20-continued

| # | Structure | t_{Ret.} (HPLC) [min] | MS (ESI+) [M + H]+ |
|---|---|---|---|
| 124 | 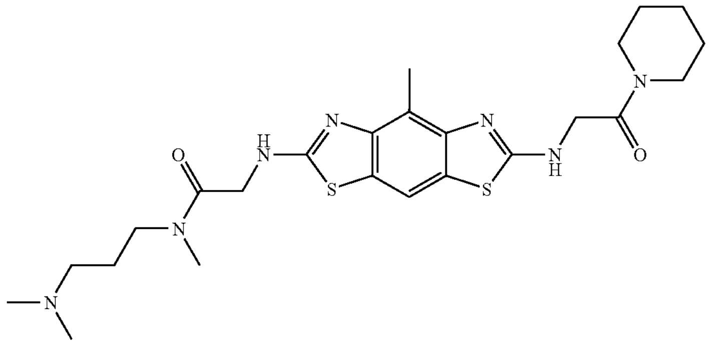 | 1.27 | 518 |
| 125 | 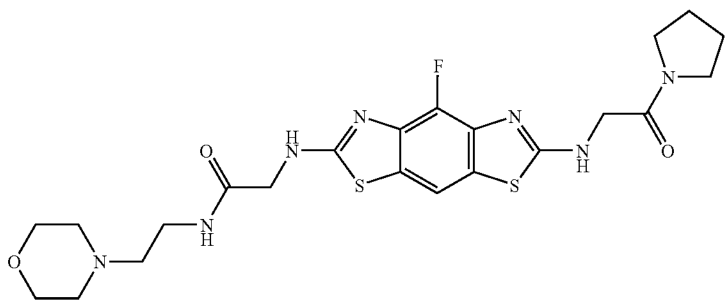 | 0.0 | 522 |
| 126 | 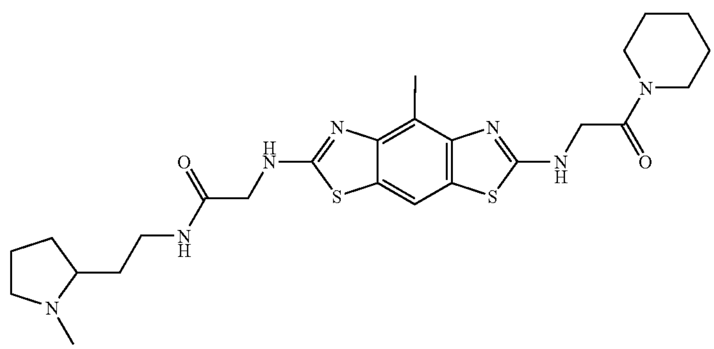 | 1.30 | 530 |
| 127 | 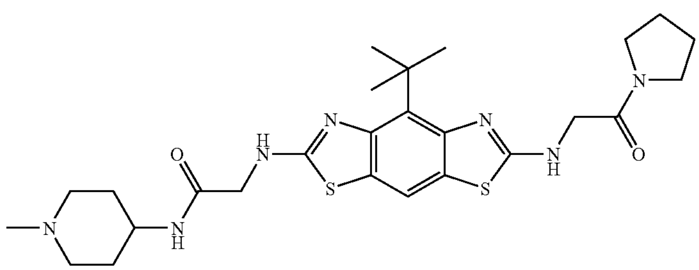 | 1.46 | 544 |
| 128 | 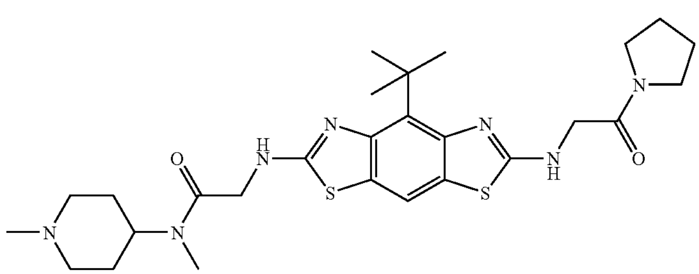 | 1.49 | 558 |

TABLE 20-continued

| # | Structure | $t_{Ret.}$ (HPLC) [min] | MS (ESI+) [M + H]$^+$ |
|---|---|---|---|
| 129 | 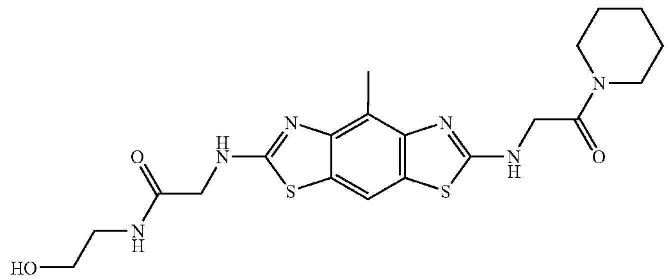 | 1.38 | 463 |
| 130 | 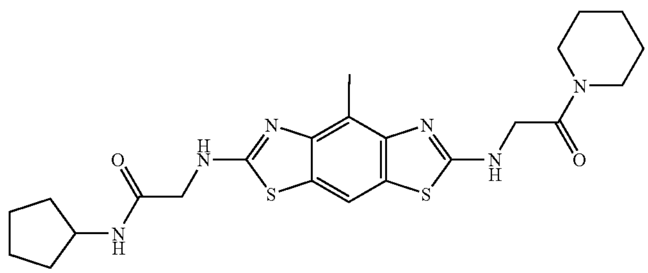 | 1.76 | 487 |
| 131 | 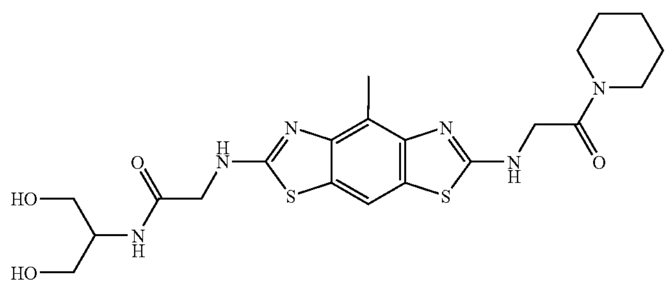 | 1.35 | 493 |
| 132 | 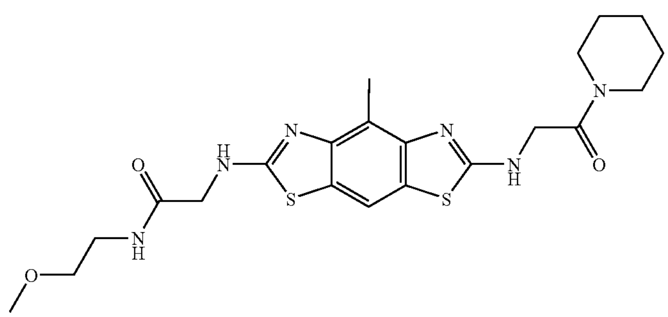 | 1.51 | 477 |
| 133 | 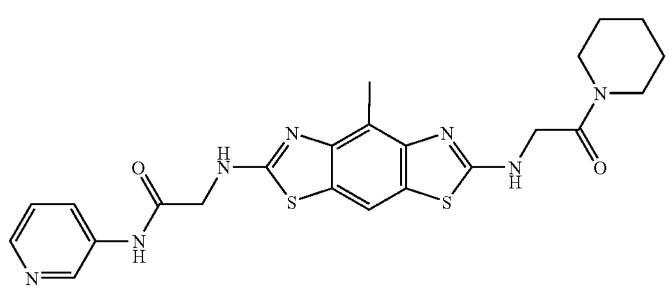 | 1.42 | 496 |

TABLE 20-continued

| # | Structure | t_Ret. (HPLC) [min] | MS (ESI+) [M + H]+ |
|---|---|---|---|
| 134 | 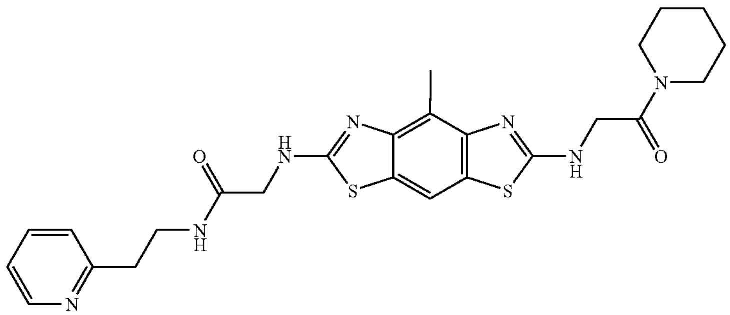 | 1.34 | 524 |
| 135 | 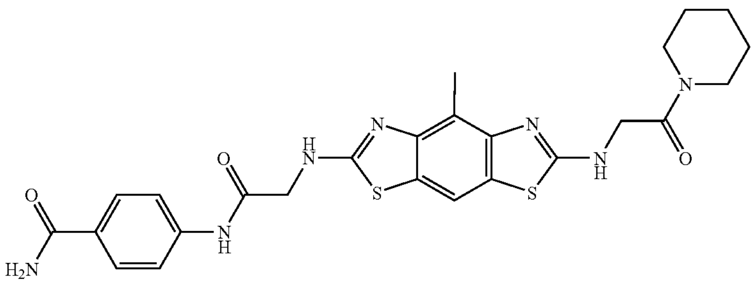 | 1.58 | 538 |
| 136 | 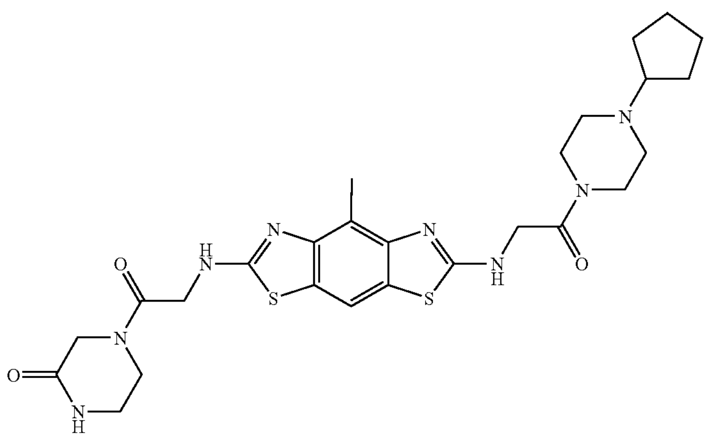 | 0.0 | 571 |
| 137 | 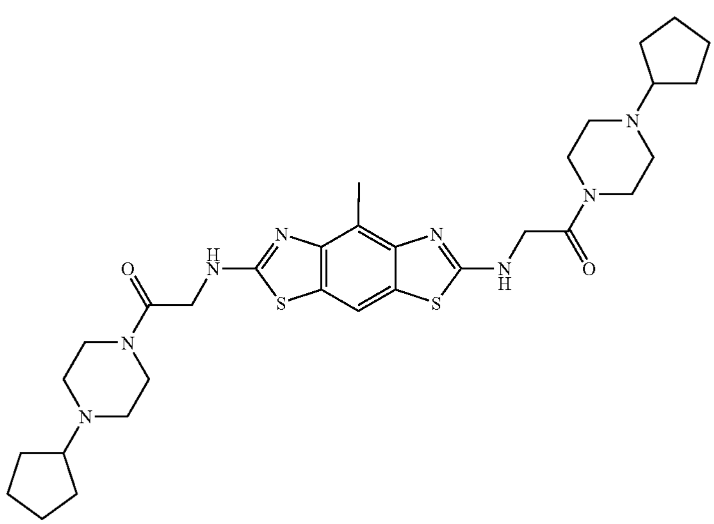 | 0.0 | 625 |

TABLE 20-continued

| # | Structure | $t_{Ret.}$ (HPLC) [min] | MS (ESI+) [M + H]+ |
|---|---|---|---|
| 138 | 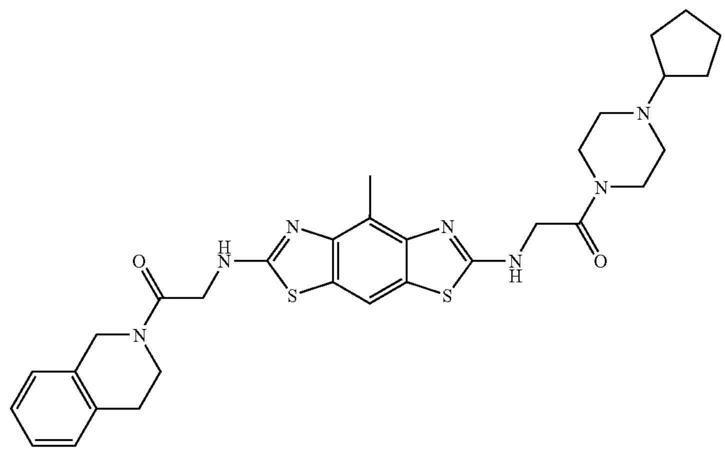 | 1.53 | 604 |
| 139 | 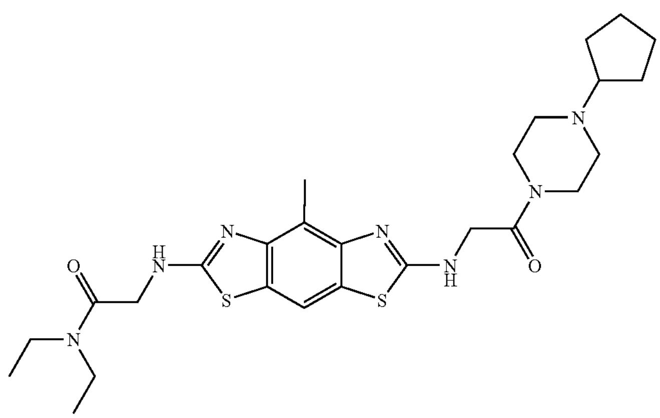 | 0.0 | 544 |
| 140 | 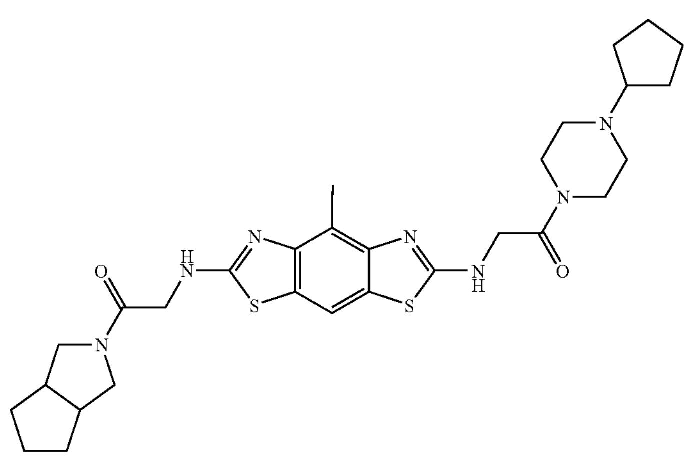 | 1.47 | 582 |

TABLE 20-continued
| # | Structure | t_Ret. (HPLC) [min] | MS (ESI+) [M + H]+ |
|---|---|---|---|
| 141 | 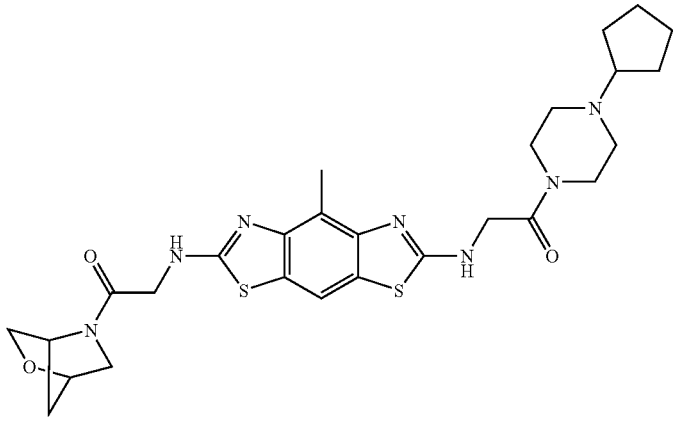 | 0.0 | 570 |
| 142 | 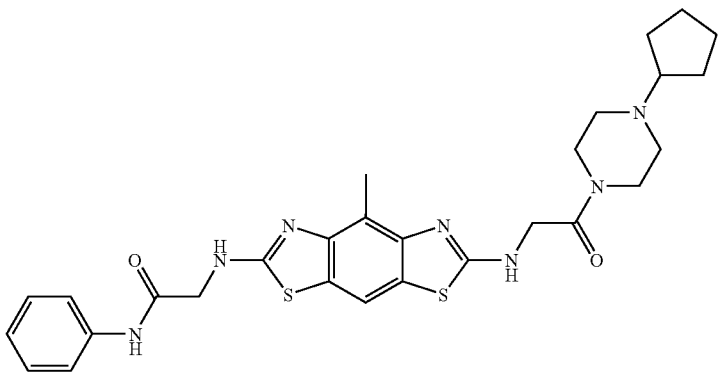 | 1.45 | 564 |
| 143 | 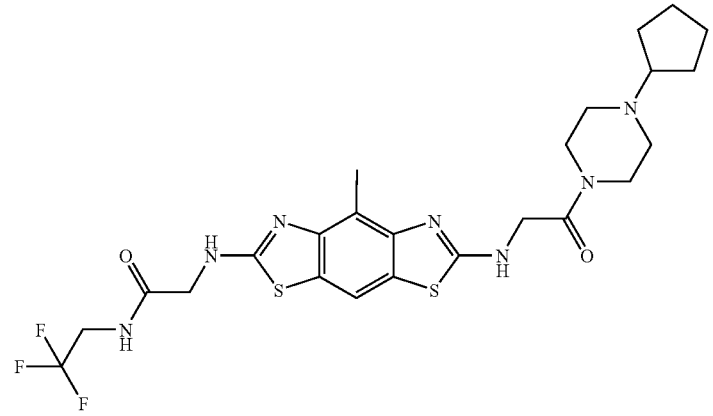 | 0.0 | 570 |
| 144 | 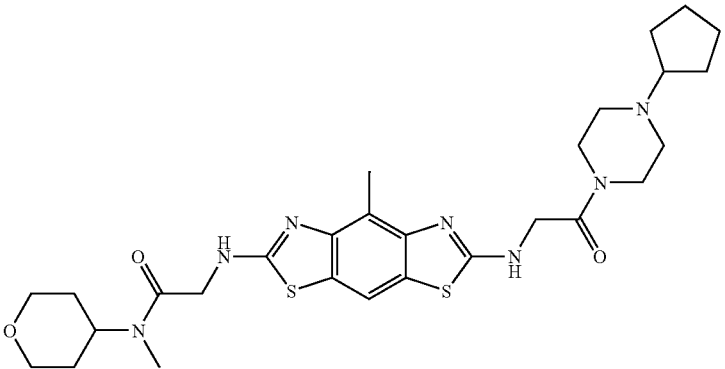 | 0.0 | 586 |

TABLE 20-continued

| # | Structure | $t_{Ret.}$ (HPLC) [min] | MS (ESI+) [M + H]$^+$ |
|---|---|---|---|
| 145 | 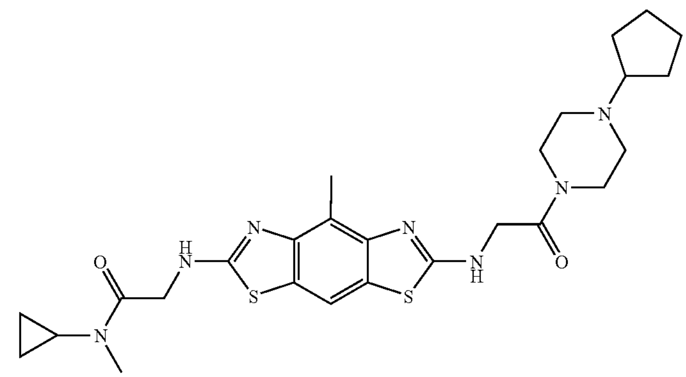 | 1.34 | 542 |
| 146 | 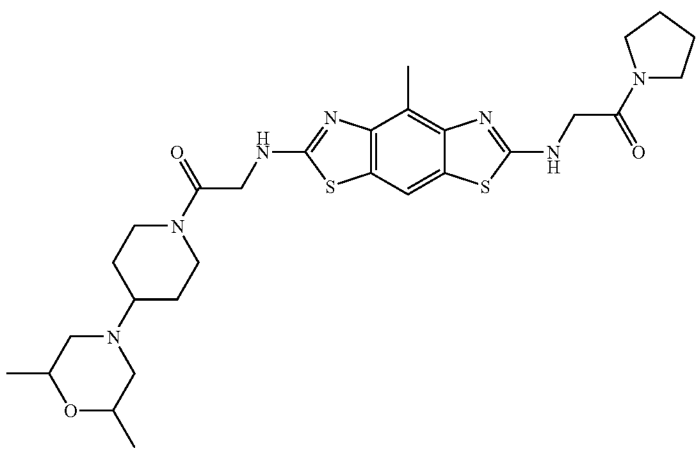 | 1.33 | 586 |
| 147 | 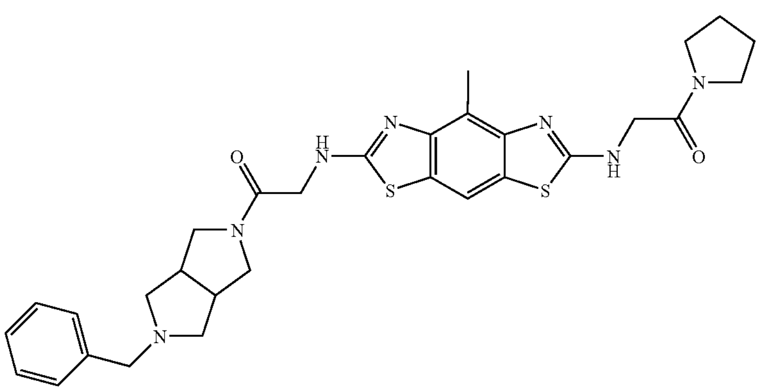 | 1.35 | 590 |

General Method for Synthesising Examples 148 and 149 (Synthesis Scheme D):

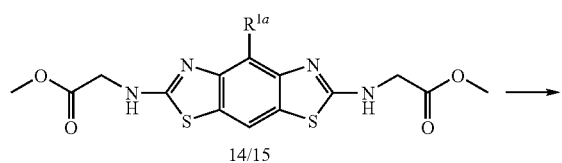

14/15

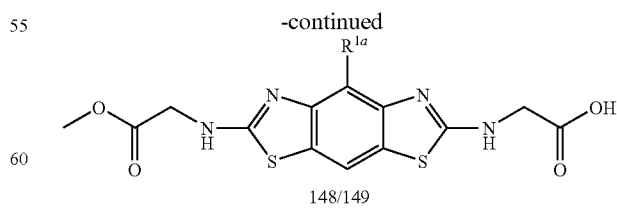

148/149

A solution of the respective bis-ester 14 or 15 in the solvent specified is combined with KOH (1-3 eq) and stirred at RT. At the moment of maximum concentration of product the reaction mixture is neutralised with hydrochloric acid and the volatile constituents are removed. The product is isolated by chromatography.

TABLE 21

| # | Structure | solvent | $t_{Ret.}$ (HPLC) [min] | MS (ESI+) [M + H]+ |
|---|---|---|---|---|
| 148 | 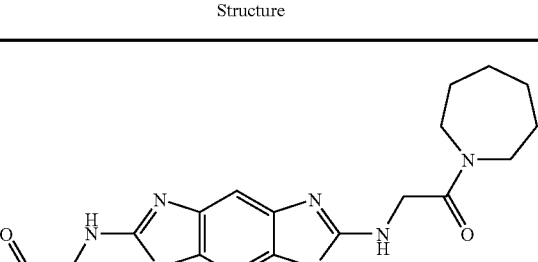 | MeOH, dioxane | 1.26 | — |
| 149 | 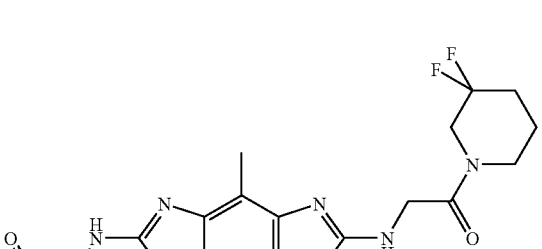 | dioxane | 1.30 | — |

General Method for Synthesising Examples 150-152 (Synthesis Scheme D):

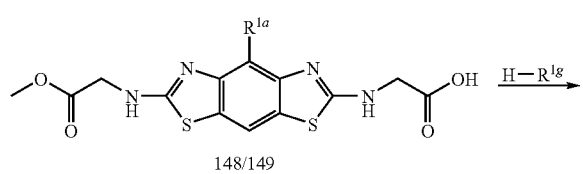

→ H—R$^{1g}$ →

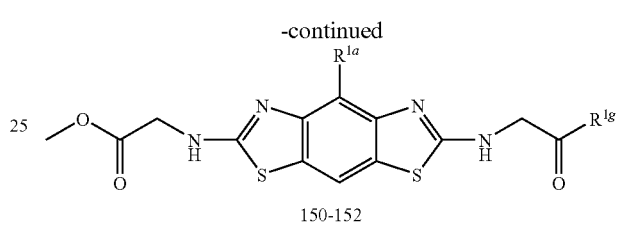

The amine H—R$^{1g}$ (1-2 eq), TBTU (1-2 eq) and DIPEA (0-6 eq) are added to the carboxylic acid 148 or 149 in DMF. The reaction mixture is stirred at RT until the reaction is complete. Then the volatile constituents are eliminated in vacuo and the product is optionally purified by chromatography.

TABLE 22

| # | Structure | $t_{Ret.}$ (HPLC) [min] | MS (ESI+) [M + H]+ |
|---|---|---|---|
| 150 | 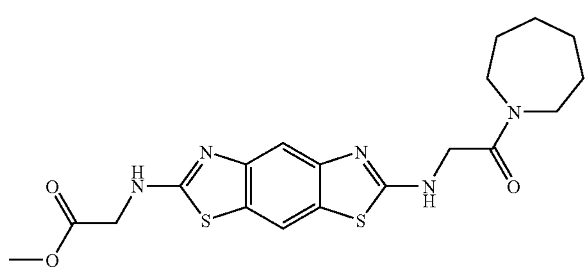 | 1.88*3 | 434 |
| 151 | 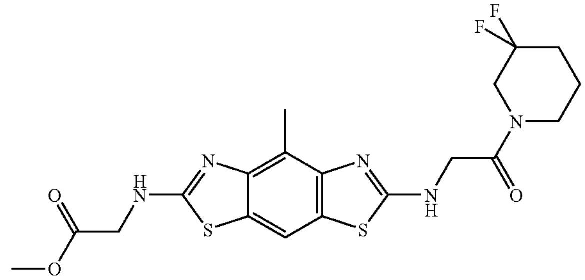 | n.a. | n.a. |

TABLE 22-continued

| # | Structure | t_Ret. (HPLC) [min] | MS (ESI+) [M + H]+ |
|---|---|---|---|
| 152 | 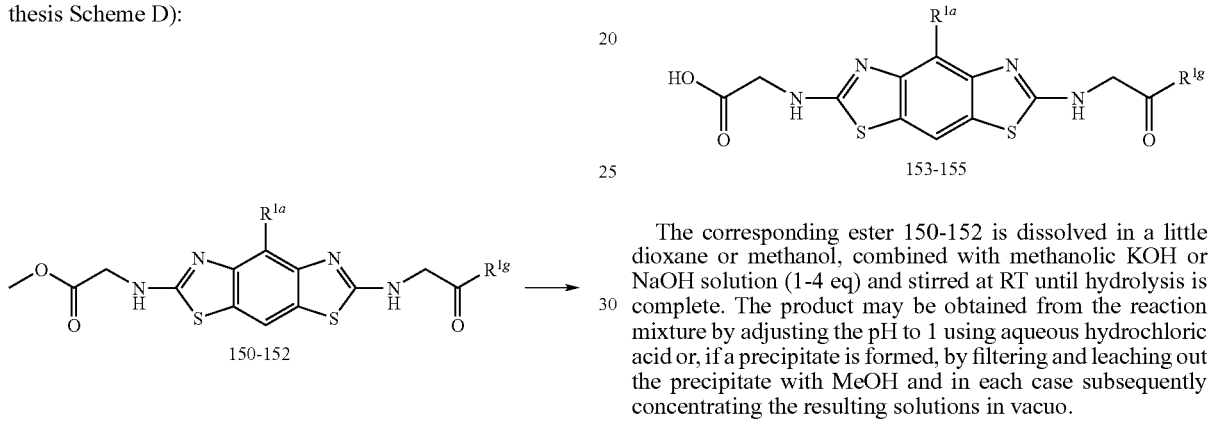 | n.a. | n.a. |

General Method for Synthesising Examples 153-155 (Synthesis Scheme D):

150-152 → 153-155

The corresponding ester 150-152 is dissolved in a little dioxane or methanol, combined with methanolic KOH or NaOH solution (1-4 eq) and stirred at RT until hydrolysis is complete. The product may be obtained from the reaction mixture by adjusting the pH to 1 using aqueous hydrochloric acid or, if a precipitate is formed, by filtering and leaching out the precipitate with MeOH and in each case subsequently concentrating the resulting solutions in vacuo.

TABLE 23

| # | Structure | t_Ret. (HPLC) [min] | MS (ESI+) [M + H]+ |
|---|---|---|---|
| 153 | 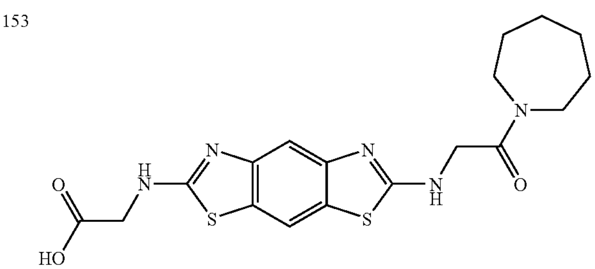 | 1.57*3 | 420 |
| 154 | 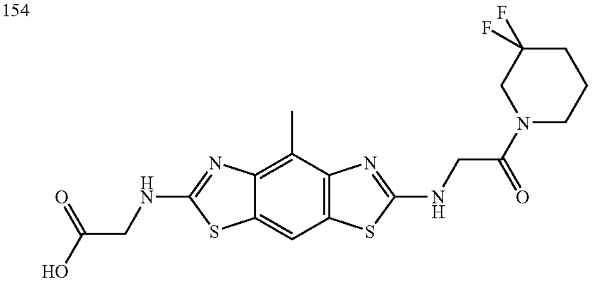 | 0.70*1 | 456 |

TABLE 23-continued
| # | Structure | $t_{Ret.}$ (HPLC) [min] | MS (ESI+) $[M + H]^+$ |
|---|---|---|---|
| 155 | 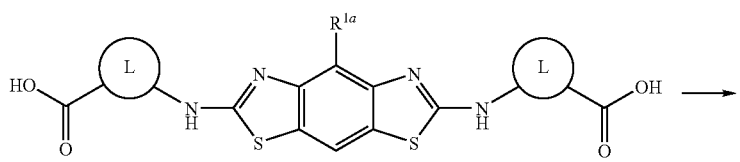 | 1.50 | 438 |
General Method for Synthesising Examples 156-177 (Synthesis Scheme D)
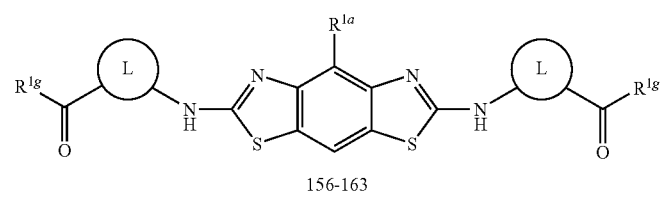 →
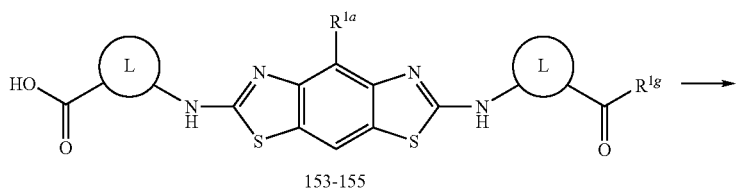
156-163
or
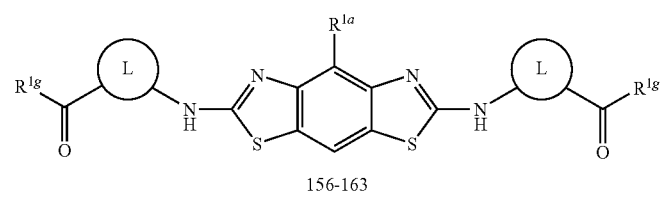 →
153-155
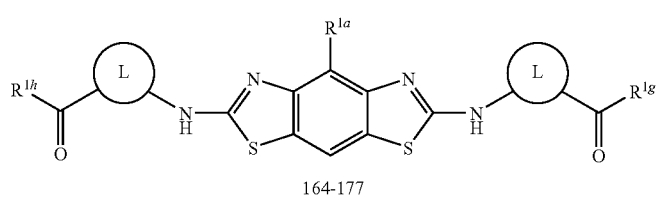
164-177

The corresponding mono- or bis-carboxylic acid (cf. for example Table 11, 18, 19, 21 or 23) is dissolved in DMF or NMP, and combined with 2-7 eq of the corresponding amine, 0-10 eq an auxiliary base, preferably DIPEA, and 1-3 eq TBTU. The reaction mixture is stirred at RT until the reaction is complete, the volatile constituents are removed and the product is isolated by chromatography.

TABLE 24

| # | Structure | $t_{Ret.}$ (HPLC) [min] | MS (ESI+) [M + H]+ |
|---|---|---|---|
| 156 | 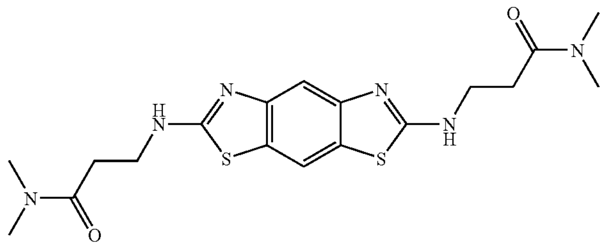 | 1.20 | 421 |
| 157 | 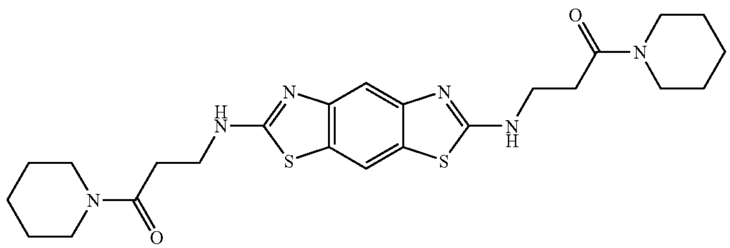 | 1.59 | 501 |
| 158 | 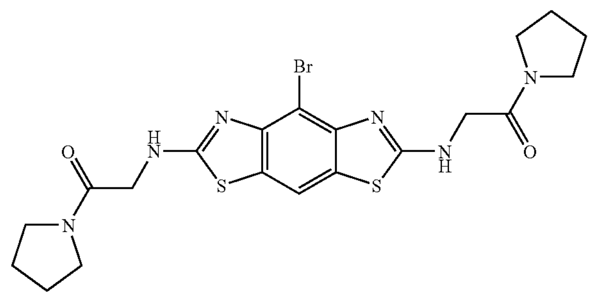 | 1.68 | 523/525 |
| 159 | 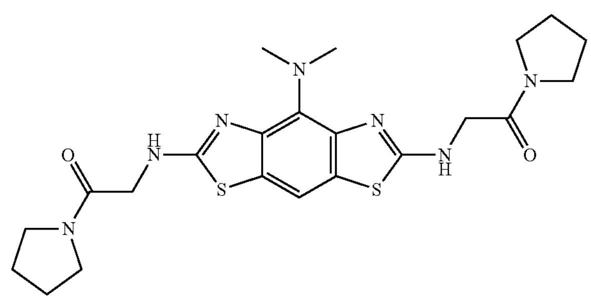 | 1.34 | 488 |
| 160 | 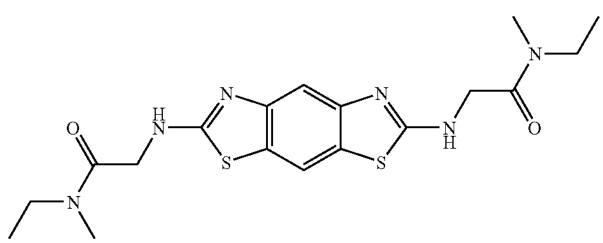 | 1.38 | 421 |

TABLE 24-continued

| # | Structure | t_Ret. (HPLC) [min] | MS (ESI+) [M + H]+ |
|---|---|---|---|
| 161 | 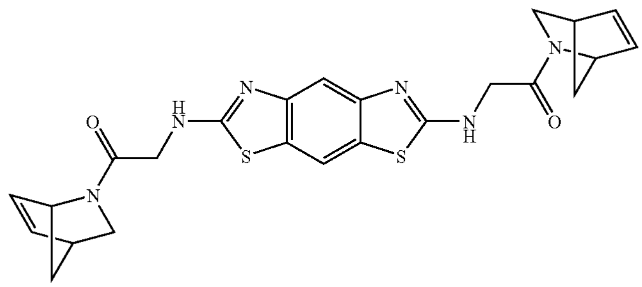 | 1.52 | 493 |
| 162 | 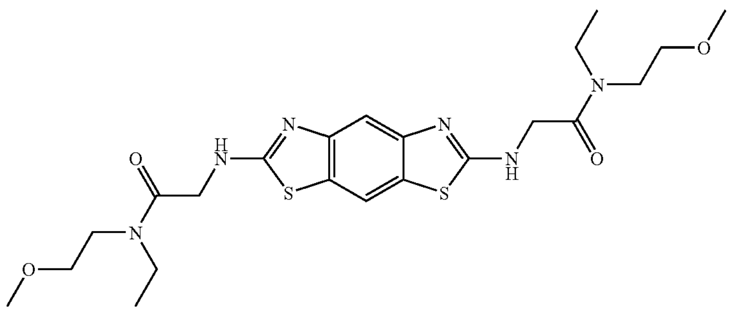 | 1.52 | 509 |
| 163 | 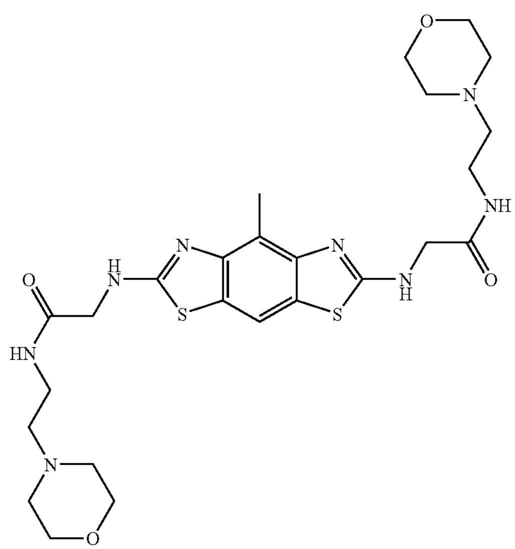 | 0.0 | 577 |
| 164 | 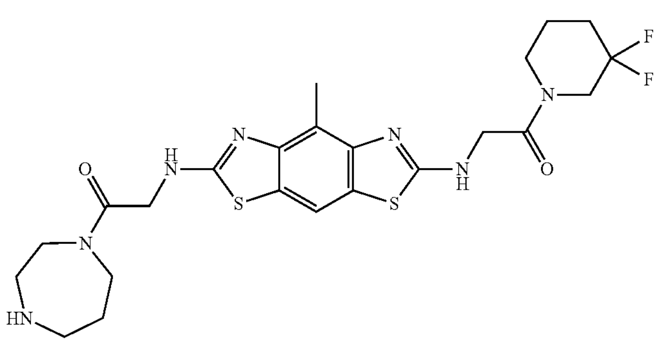 | 0.0 | 538 |

TABLE 24-continued

| # | Structure | $t_{Ret.}$ (HPLC) [min] | MS (ESI+) $[M + H]^+$ |
|---|---|---|---|
| 165 | 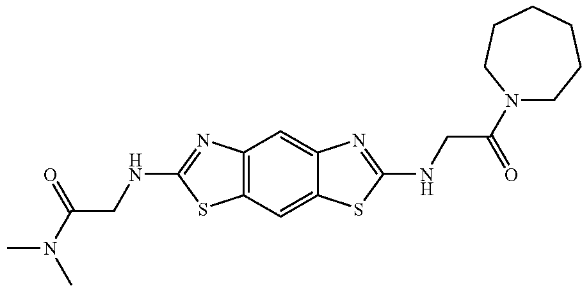 | 1.52 | n.a. |
| 166 | 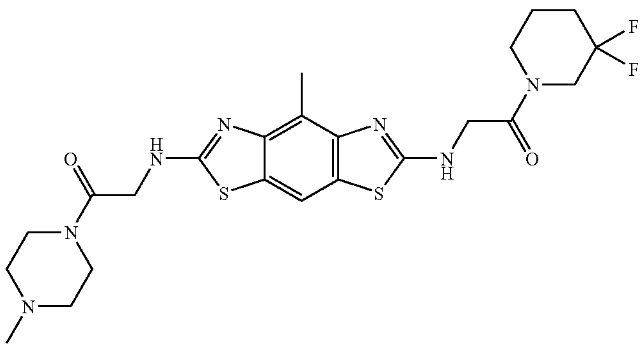 | 0.0 | 538 |
| 167 | 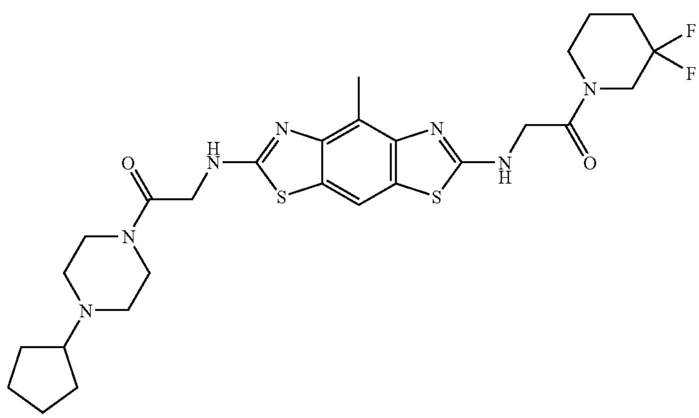 | 1.39 | 592 |
| 168 | 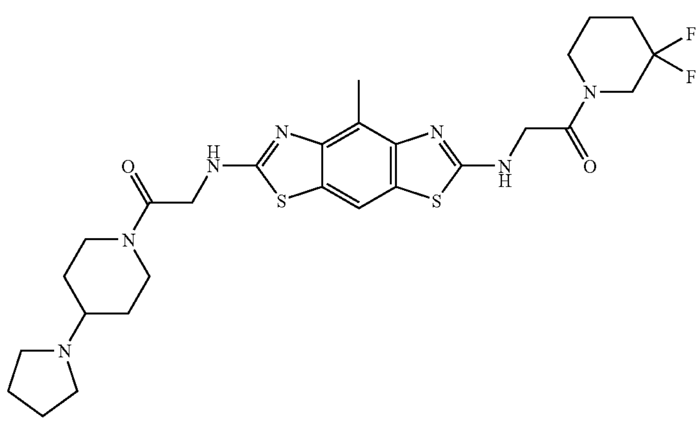 | 0.0 | 592 |

TABLE 24-continued
| # | Structure | t_Ret. (HPLC) [min] | MS (ESI+) [M + H]+ |
|---|---|---|---|
| 169 | 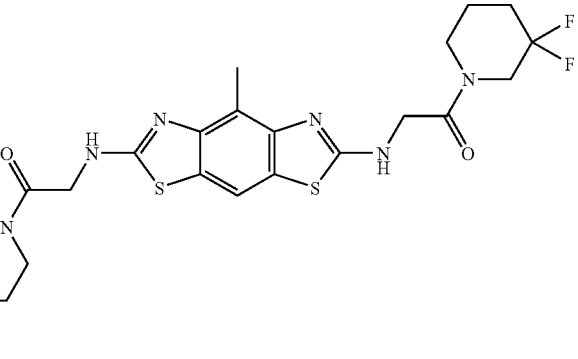 | 1.29 | 566 |
| 170 | 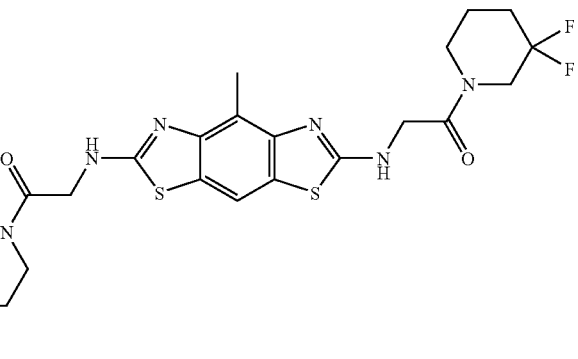 | 0.0 | 595 |
| 171 | 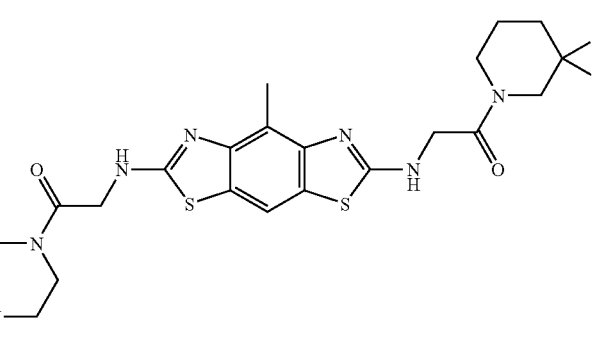 | 0.0 | 582 |

TABLE 24-continued

| # | Structure | t<sub>Ret.</sub> (HPLC) [min] | MS (ESI+) [M + H]⁺ |
|---|---|---|---|
| 172 | 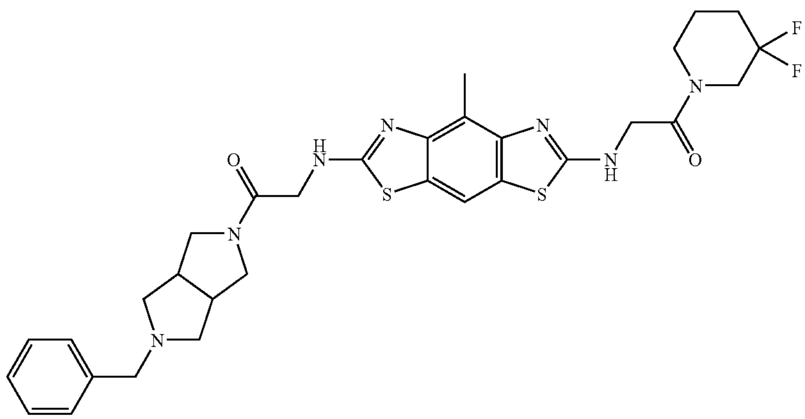 | 1.47 | 640 |
| 173 | 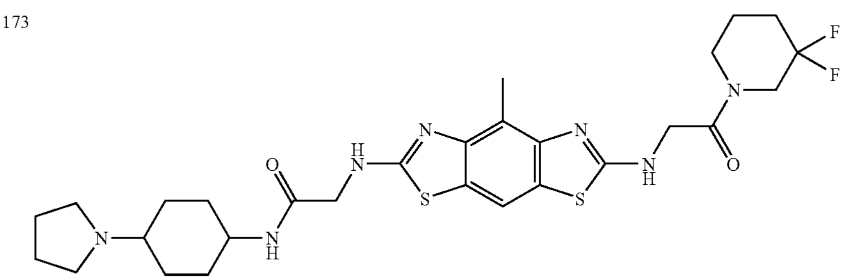 | 0.0 | 606 |
| 174 | 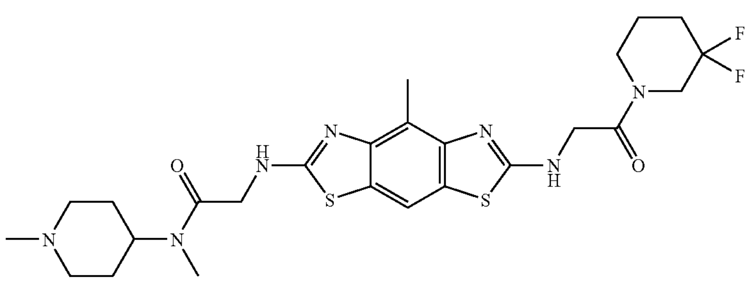 | 1.35 | 566 |
| 175 | 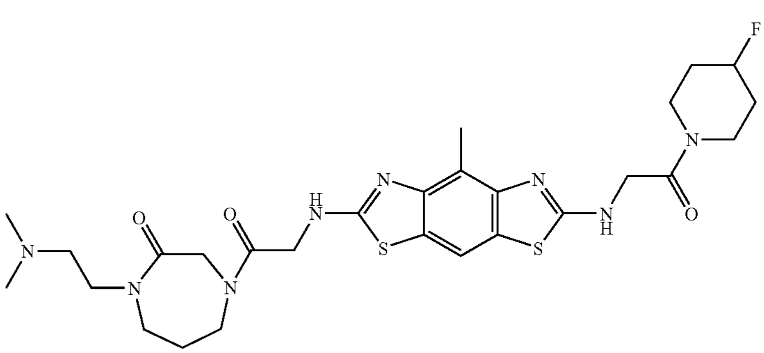 | 0.0 | 605 |

TABLE 24-continued

| # | Structure | $t_{Ret.}$ (HPLC) [min] | MS (ESI+) [M + H]$^+$ |
|---|---|---|---|
| 176 | 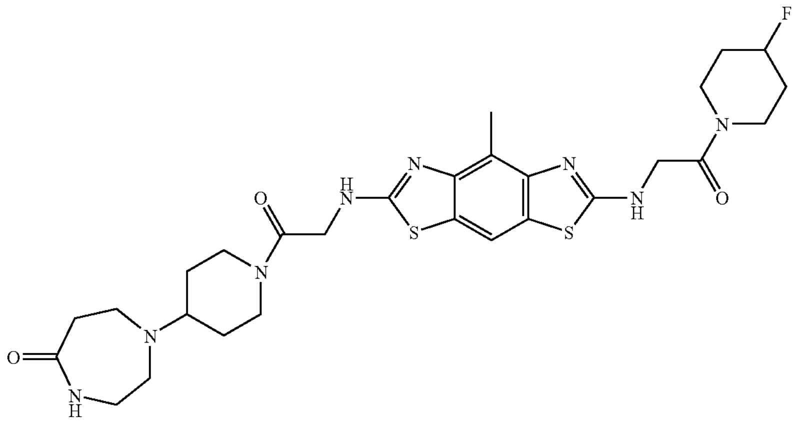 | F 0.0 | 617 |
| 177 | 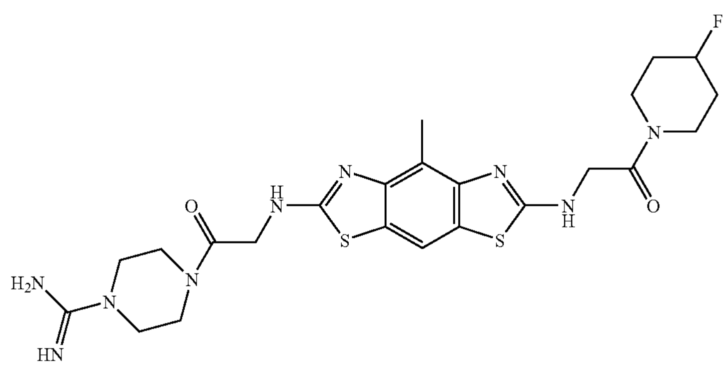 | F 0.0 | 548 |

Preparation of E-2a:

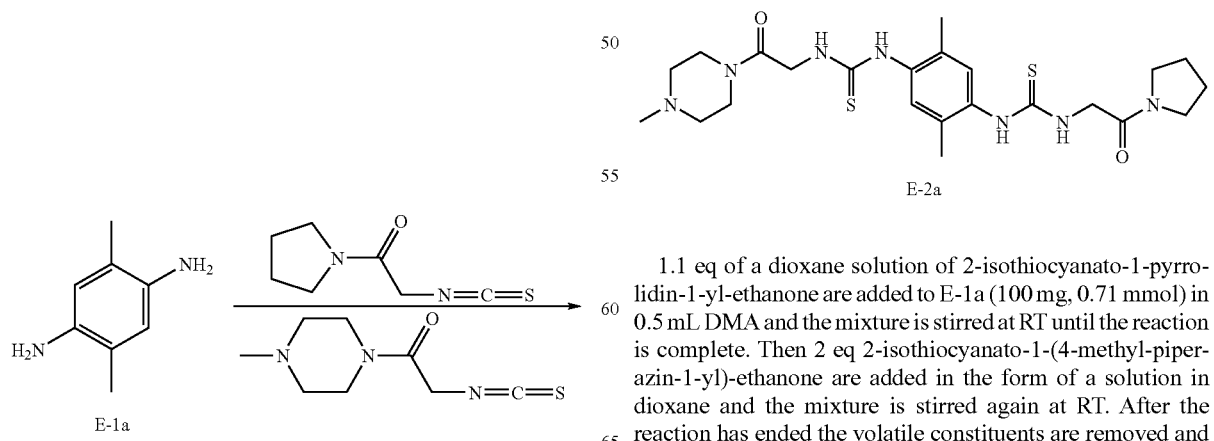

1.1 eq of a dioxane solution of 2-isothiocyanato-1-pyrrolidin-1-yl-ethanone are added to E-1a (100 mg, 0.71 mmol) in 0.5 mL DMA and the mixture is stirred at RT until the reaction is complete. Then 2 eq 2-isothiocyanato-1-(4-methyl-piperazin-1-yl)-ethanone are added in the form of a solution in dioxane and the mixture is stirred again at RT. After the reaction has ended the volatile constituents are removed and the product is isolated by chromatography. (HPLC $t_{Ret.}$=0.0 min; MS [M+H]$^+$: m/z=506)

Preparation of Example 178

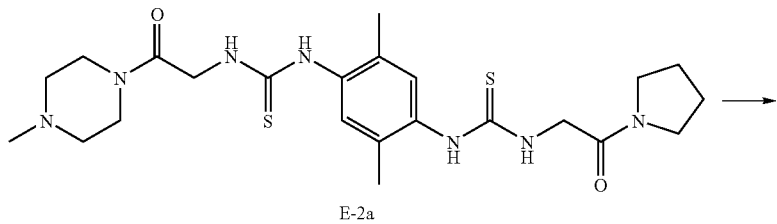

E-2a

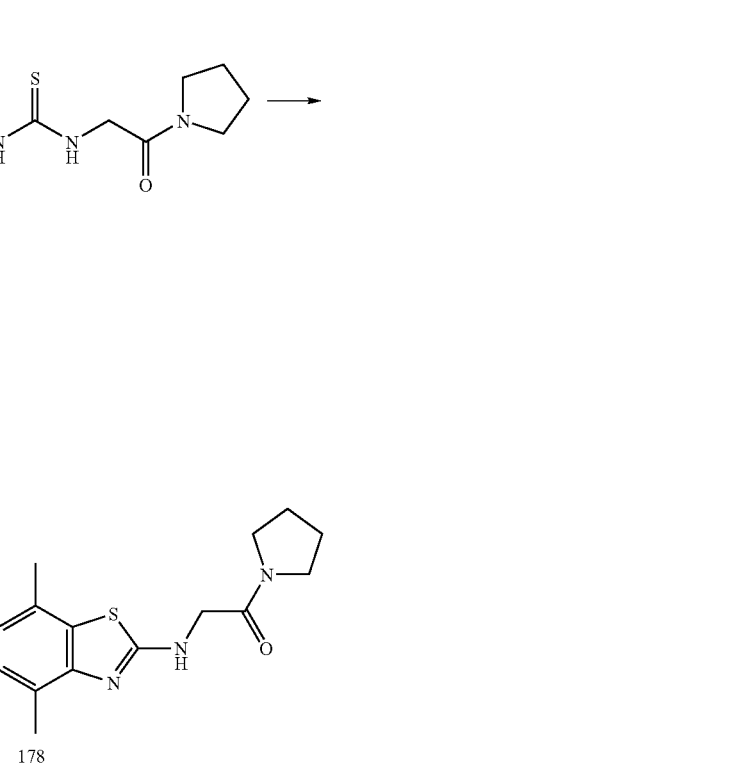

178

A solution of E-2a (60 mg, 0.12 mmol) in 0.2 mL chloroform is combined at RT with 0.17 mL of a solution of bromine in chloroform (c=1 mol/L). The reaction mixture is stirred at RT until the reaction has ended. The volatile constituents are eliminated in vacuo and the product is isolated by chromatography.

(HPLC $t_{Ret.}$=0.0 min; MS [M+H]$^+$: m/z=502)

Preparation of E-5a:

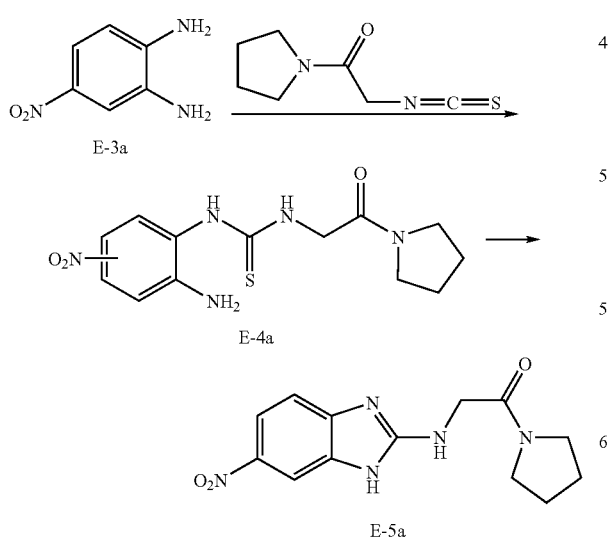

4-nitro-1,2-diaminobenzene (1.0 g, 6.5 mmol) in 10 mL dioxane is combined with 1.1 eq of a dioxanic solution of 2-isothiocyanato-1-pyrrolidin-1-yl-ethanone. The reaction mixture is stirred at 60° C. until the reaction is complete. The volatile constituents are removed and the intermediate product E-4a is purified by chromatography. E-4a is dissolved in THF and combined with 1.1 eq DIC. The reaction mixture is stirred for 24 h at 50° C. After elimination of the volatile constituents the product E-5a is isolated by chromatography.

(HPLC $t_{Ret.}$=0.41*$^1$ min; MS [M+H]$^+$: m/z=290).

Preparation of E-6a:

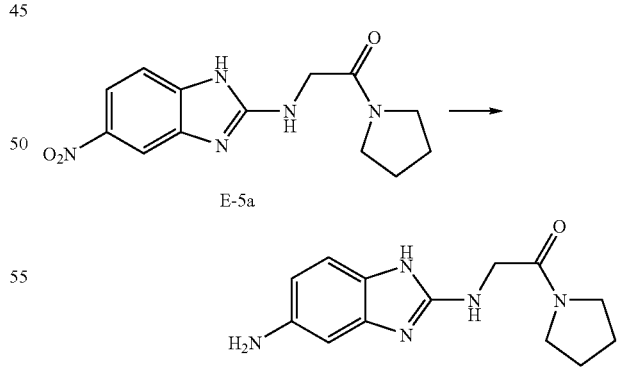

E-5a (280 mg. 0.97 mmol) is dissolved in 80 mL THF. After the addition of approx. 50 mg Pd/C the reaction mixture is stirred under 5 bar excess H$_2$ pressure. After the reaction has ended the reaction mixture is filtered and freed from the volatile constituents. The product is further used directly.

(HPLC $t_{Ret.}$=0.0 min; MS [M+H]$^+$: m/z=260).

Preparation of Example 179:

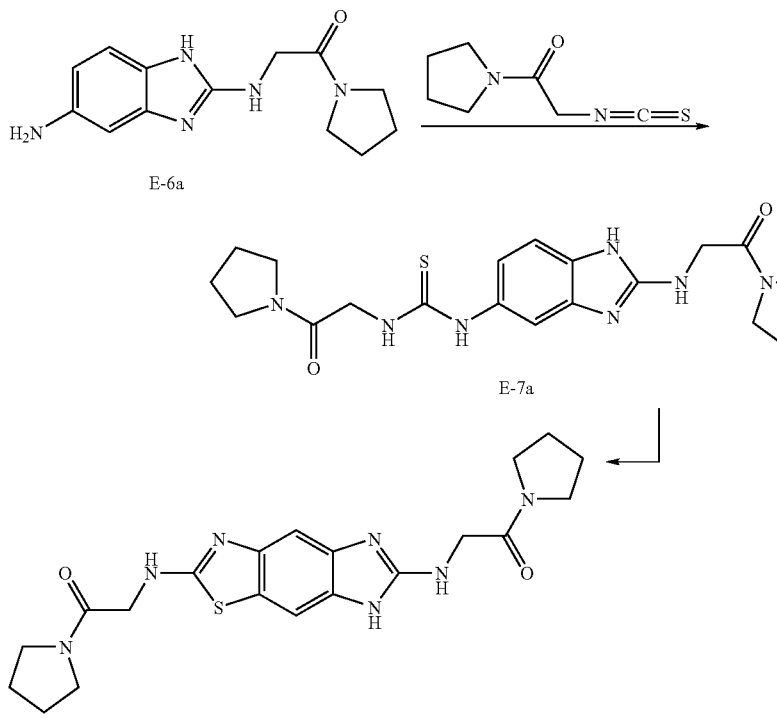

1.1 eq 2-isothiocyanato-1-pyrrolidin-1-yl-ethanone as a solution in DMA are added to E-6a (50 mg, 0.19 mmol) in 0.5 mL dioxane. After stirring at RT until the reaction is complete the volatile constituents are removed. The crude product E-7a is combined with 4 mL DCM and 80 mg benzyltrimethylammonium-tribromide and stirred at RT until the reaction is complete. After elimination of the volatile constituents the product is isolated by chromatography. (HPLC $t_{Ret.}$=0.0 min; MS [M+H]$^+$: m/z=428).

Preparation of E-8a:

An excess of aqueous ammonia solution is added to 2-isothiocyanato-1-pyrrolidin-1-yl-ethanone (0.59 mmol) as an approx. 0.7 M solution in DMA. The reaction mixture is stirred at RT until the reaction is complete and then all the volatile constituents are eliminated. E-8a is further used directly. (HPLC $t_{Ret.}$=0.26*$^1$ min; MS [M+H]$^+$: m/z=188).

Preparation of Example 180:

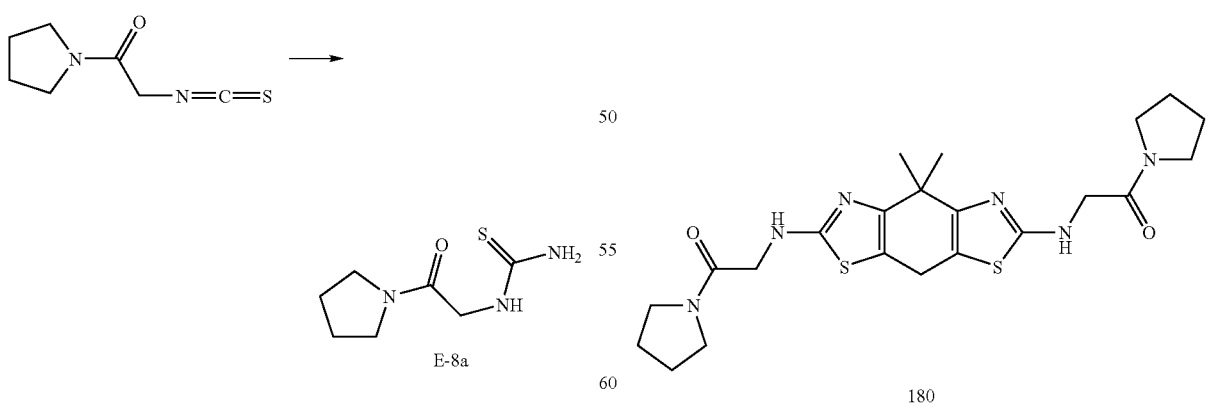

E-8a (88 mg, 0.47 mmol) and E-9a (70 mg, 0.235 mmol) are combined with 1 mL THF and refluxed. After the reaction has ended the volatile constituents are eliminated and the product is isolated by chromatography. (HPLC $t_{Ret.}$=1.45 min; MS [M+H]$^+$: m/z=475).

TABLE 25

| # | Structure | $t_{Ret.}$ (HPLC) [min] | MS (ESI+) [M + H]$^+$ |
|---|---|---|---|
| 178 | 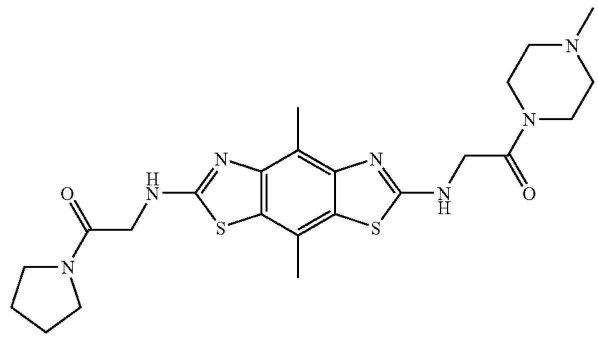 | 0.0 | 502 |
| 179 | 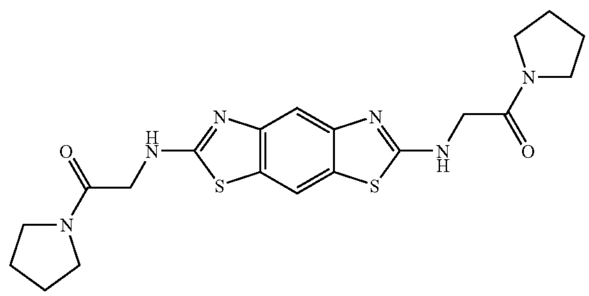 | 0.0 | 428 |
| 180 | 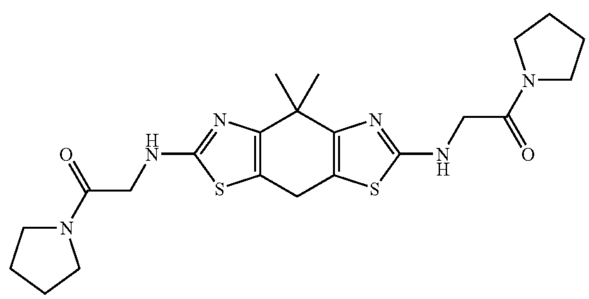 | 1.45 | 475 |

The following Examples describe the biological activity of the compounds according to the invention without restricting the invention to these Examples.

Compounds of general formulae (1), (1A), (1B) and (1C) are characterised by their wide range of applications in the therapeutic field. Particular mention should be made of those applications in which the inhibition of specific cell cycle kinases, particularly the inhibiting effect on the proliferation of cultivated human tumour cells but also the proliferation of other cells, such as endothelial cells, for example, plays a part.

As demonstrated by DNA staining followed by Cellomics Array Scan analysis (Cellcycle Analysis), the inhibition of proliferation brought about by the compounds according to the invention is mediated above all by the defective formation of bipolar mitotic spindles. As a result the duplicated chromosomes cannot be correctly divided into two daughter cells, leading finally to inhibition of proliferation and apoptosis.

Measurement of the Inhibition of Proliferation on Cultivated Human Tumour Cells

To measure proliferation on cultivated human tumour cells, cells of colon carcinoma cell line HCT 116 (American Type Culture Collection (ATCC)) are cultivated in RPMI 1640 medium (Gibco) and 10% foetal calf serum (Gibco). Then the HCT 116 cells are placed in 96-well flat-bottomed plates (Falcon) at a density of 1400 cells per well in RPMI 1640 medium and incubated overnight in an incubator (at 37° C. and 5% $CO_2$). The active substances are added to the cells in various concentrations. After 72 hours incubation 20 µl AlamarBlue reagent (AccuMed International) is added to each well, and the cells are incubated for a further 3-4 hours. After incubation the colour change of the AlamarBlue reagent is determined in a Wallac Microbeta fluorescence spectrophotometer. $EC_{50}$ values are calculated using Standard Levenburg Marquard algorithms (GraphPadPrizm). Most of the compounds of Examples 1 to 180 exhibit good to very good activity in the above inhibition test, i.e. an $EC_{50}$ value of less than 5 µmol, generally less than 1 µmol. Correspondingly, the compounds according to the invention are also tested on other tumour cells. For example these compounds are actively tested on carcinomas of all kinds of tissue [e.g. lung (NCI-H460) and prostate (PC-3)] and may be used for such indications.

This demonstrates the broad range of uses of the compounds according to the invention for treating all kinds of tumours.

Cellomics Array Scan

NCI-H460 cells are seeded into fibronectin-coated 96-well dishes (BD BioCoat) in RPMI 1640 medium (Gibco) with 10% foetal calf serum (Gibco) in a density of 4000 cells per well and incubated overnight in an incubator (at 37° C. and 5% $CO_2$). The active substances are added to the cells in various concentrations. After 24 h incubation the cells are fixed for 10 min by the addition of 100 μL with 7.4% formaldehyde solution at RT, and washed twice with PBS solution. Then the cells are permeabilised by the addition of 100 μL of 0.1% Triton X100 in PBS for 90 seconds, the permeabilising solution is removed by suction filtering and washed with PBS. Non-specific binding sites are saturated by incubating for 20 min with blocking solution (10% Normal Goat Serum in 2% BSA/PBS). After a washing step with PBS, antibodies against phosphorylated histone H3 (1:500 diluted, Upstate) or against tubulin (1:1000 diluted, Sigma) in 2% BSA/PBS are added and the mixture is incubated for 60 min, washed twice with 0.01% Tween/PBS and incubated for 1 h with Alexa 488-Goat anti Mouse (diluted 1:1000), Alexa 594-Goat anti Rabbit (diluted 1:5000) and 4',6-diamidino-2-phenylindole (DAPI, final concentration 300 nM, Molecular Probes) in 2% BSA/PBS in the dark. After washing twice with 0.01% Tween/PBS and a washing step with PBS the wells are filled with 270 μL of PBS, stuck down with black adhesive film and analysed in the Array Scan of Cellomics. For this, the DNA content of the cells is determined and the cell cycle arrest phase is established. In parallel, analysis of the spindle shape and the content of phosphorylated histone H3 allows a more precise assessment of the cell cycle arrest to be made.

On the basis of their biological properties the new compounds of general formula (1), (1A), (1B) and (1C), the isomers thereof, pharmacologically acceptable salts and polymorphs thereof are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy). They are also useful for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, giant cell tumour, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma; vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1), (1A), (1B) and (1C) may be used on their own or in combination with other active substances according to the invention, optionally also in combination with other pharmacologically active substances.

Chemotherapeutic agents which may be administered in combination with the compounds according to the invention include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions, —particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples that follow illustrate the present invention without restricting its scope:

Examples of Pharmaceutical Formulations

| A) Tablets | per tablet |
|---|---|
| active substance according to formula (1), (1A), (1B) and (1C) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (1), (1A), (1B) and (1C) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (1), (1A), (1B) and (1C) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. A compound of formula (1C)

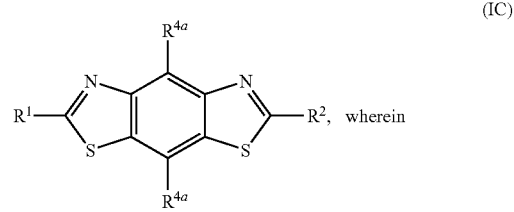

(1C)

wherein $R^1$ and $R^2$ independently of one another are selected from the group consisting of —$NR^a R^a$, —$N(R^g)S(O)_2 R^a$ and a nitrogen-containing 3-8 membered heterocycloalkyl attached via a cyclic nitrogen, this heterocycloalkyl optionally being substituted by one or more identical or different group(s) selected from the group consisting of $R^a$ and $R^b$, each $R^{4a}$ independently of one another is selected from the group consisting of $R^a$ and $R^b$, each $R^a$ independently of one another denotes hydrogen or a group optionally substituted by one or more identical or different $R^b$ and/or $R^c$, selected from the group consisting of $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^b$ is a group selected in each case independently of one another from the group consisting of —$OR^c$, $C_{1-3}$haloalkyloxy, —$OCF_3$, =S, —$SR^c$, =$NR^c$, =$NOR^c$, =$NNR^c R^c$, =$NN(R^g)C(O)NR^c R^c$, —$NR^c R^c$, —$ONR^c R^c$, —$N(OR^c)R^c$, —$N(R^g)NR^c R^c$, halogen, —$CF_3$, —CN, —NC, —OCN, —SCN, —NO, —$NO_2$, =$N_2$, —$N_3$, —$S(O)R^c$, —$S(O)OR^c$, —$S(O)_2 R^c$, —$S(O)_2 OR^c$, —$S(O)NR^c R^c$, —$S(O)_2 NR^c R^c$, —$OS(O)R^c$, —$OS(O)_2 R^c$, —$OS(O)_2 OR^c$, —$OS(O)NR^c R^c$, —$OS(O)_2 NR^c R^c$, —$C(O)R^c$, —$C(O)OR^c$, —$C(O)SR^c$, —$C(O)NR^c R^c$, —$C(O)N(R^g)NR^c R^c$, —$C(O)N(R^g)OR^c$, —$C(NR^g)NR^c R^c$, —$C(NOH)R^c$, —$C(NOH)NR^c R^c$, —$OC(O)R^c$, —$OC(O)OR^c$, —$OC(O)SR^c$, —$OC(O)NR^c R^c$, —$OC(NR^g)NR^c R^c$, —$SC(O)R^c$, —$SC(O)OR^c$, —$SC(O)NR^c R^c$, —$SC(NR^g)NR^c R^c$, —$N(R^g)C(O)R^c$, —$N[C(O)R^c]_2$, —$N(OR^c)C(O)R^c$, —$N(R^g)C(NR^g)R^c$, —$N(R^g)N(R^g)C(O)R^c$, —$N[C(O)R^c]NR^c R^c$, —$N(R^g)C(S)R^c$, —$N(R^g)S(O)R^c$, —$N(R^g)S(O)OR^c$, —$N(R^g)S(O)_2 R^c$, —$N[S(O)_2 R^c]_2$, —$N(R^g)S(O)_2 OR^c$, —$N(R^g)S(O)_2 NR^c R^c$, —$N(R^g)[S(O)_2]_2 R^c$, —$N(R^g)C(O)OR^c$, —$N(R^g)C(O)SR^c$, —$N(R^g)C(O)NR^c R^c$, —$N(R^g)C(O)NR^g NR^c R^c$, —$N(R^g)N(R^g)C(O)NR^c R^c$, $N(R^g)C(S)NR^c R^c$, —$[N(R^g)C(O)]_2 R^c$, —$N(R^g)[C(O)]_2 R^c$, —$N\{[C(O)]_2 R^c\}_2$, —$N(R^g)[C(O)]_2 OR^c$, —$N(R^g)[C(O)]_2 NR^c R^c$, —$N\{[C(O)]_2 OR^c\}_2$, —$N\{[C(O)]_2 NR^c R^c\}_2$, -$[N(R^g)C(O)]_2 OR^c$, —$N(R^g)C(NR^g)OR^c$, —$N(R^g)C(NOH)R^c$, —$N(R^g)C(NR^g)SR^c$ and —$N(R^g)C(NR^g)NR^c R^c$, each $R^c$ independently of one another denotes hydrogen or a group optionally substituted by one or more identical or different $R^d$ and/or $R^e$, selected from the group consisting of $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^d$ is a group selected in each case independently of one another from the group consisting of =O, —OR$^e$, $C_{1-3}$haloalkyloxy, —OCF$_3$, =S, —SR$^e$, =NR$^e$, =NOR$^e$, =NNR$^e$R$^e$, =NN(R$^g$)C(O)NR$^e$R$^e$, —NR$^e$R$^e$, —ONR$^e$R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$, —N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$R$^e$, N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$ and —N(R$^g$)C(NR$^g$)NR$^e$R$^e$, each $R^e$ independently of one another denotes hydrogen or a group optionally substituted by one or more identical or different $R^f$ and/or $R^g$, selected from the group consisting of $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^f$ is a group selected in each case independently of one another from the group consisting of =O, —OR$^g$, $C_{1-3}$haloalkyloxy, —OCF$_3$, =S, —SR$^g$, =NR$^g$, =NOR$^g$, =NNR$^g$R$^g$, =NN(R$^h$)C(O)NR$^g$R$^g$, —NR$^g$R$^g$, —ONR$^g$R$^g$, —N(R$^h$)NR$^g$R$^g$, halogen, —CF$_3$, —CN, —NC, —OCN, —SCN, —NO, —NO$_2$, =N$_2$, —N$_3$, —S(O)R$^g$, —S(O)OR$^g$, —S(O)$_2$R$^g$, —S(O)$_2$OR$^g$, —S(O)NR$^g$R$^g$, —S(O)$_2$NR$^g$R$^g$, —OS(O)R$^g$, —OS(O)$_2$R$^g$, —OS(O)$_2$OR$^g$, —OS(O)NR$^g$R$^g$, —OS(O)$_2$NR$^g$R$^g$, —C(O)R$^g$, —C(O)OR$^g$, —C(O)SR$^g$, —C(O)NR$^g$R$^g$, —C(O)N(R$^h$)NR$^g$R$^g$, —C(O)N(R$^h$)OR$^g$, —C(NR$^h$)NR$^g$R$^g$, —C(NOH)R$^g$, —C(NOH)NR$^g$R$^g$, —OC(O)R$^g$, —OC(O)OR$^g$, —OC(O)SR$^g$, —OC(O)NR$^g$R$^g$, —OC(NR$^h$)NR$^g$R$^g$, —SC(O)R$^g$, —SC(O)OR$^g$, —SC(O)NR$^g$R$^g$, —SC(NR$^h$)NR$^g$R$^g$, —N(R$^h$)C(O)R$^g$, —N[C(O)R$^g$]$_2$, —N(OR$^h$)C(O)R$^g$, —N(R$^h$)C(NR$^h$)R$^g$, —N(R$^h$)N(R$^h$)C(O)R$^g$, —N[C(O)R$^g$]NR$^g$R$^g$, —N(R$^h$)C(S)R$^g$, —N(R$^h$)S(O)R$^g$, —N(R$^h$)S(O)OR$^g$, —N(R$^h$)S(O)$_2$R$^g$, —N[S(O)$_2$R$^g$]$_2$, —N(R$^h$)S(O)$_2$OR$^g$, —N(R$^h$)S(O)$_2$NR$^g$R$^g$, —N(R$^h$)S(O)$_2$]$_2$R$^g$, —N(R$^h$)C(O)OR$^g$, —N(R$^h$)C(O)SR$^g$, —N(R$^h$)C(O)NR$^g$R$^g$, —N(R$^h$)C(O)NR$^h$NR$^g$R$^g$, —N(R$^h$)N(R$^h$)C(O)NR$^g$R$^g$, —N(R$^h$)C(S)NR$^g$R$^g$, —[N(R$^h$)C(O)]$_2$R$^g$, —N(R$^h$)[C(O)]$_2$R$^g$, —N{[C(O)]$_2$R$^g$}$_2$, —N(R$^h$)[C(O)]$_2$OR$^g$, —N(R$^h$)[C(O)]$_2$NR$^g$R$^g$, —N{[C(O)]$_2$OR$^g$}$_2$, —N{[C(O)]$_2$NR$^g$R$^g$}$_2$, —[N(R$^h$)C(O)]$_2$OR$^g$, —N(R$^h$)C(NR$^h$)OR$^g$, —N(R$^h$)C(NOH)R$^g$, —N(R$^h$)C(NR$^h$)SR$^g$ and —N(R$^h$)C(NR$^h$)NR$^g$R$^g$, each $R^g$ independently of one another denotes hydrogen or a group optionally substituted by one or more identical or different $R^h$, selected from the group consisting of $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^h$ independently of one another is selected from the group consisting of hydrogen, $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, optionally in the form of tautomers, racemates, enantiomers, diastereomers and mixtures thereof, and optionally pharmacologically acceptable salts thereof, with the provisos that neither $R^1$ nor $R^2$ corresponds to the amino group —NH$_2$ and the compounds

[6-(carboxymethyl-amino)-benzo[1,2-d;5,4-d]bisthiazol-2-ylamino]-acetic acid,

2-[6-(diethylcarbamoylmethyl-amino)-benzo[1,2-d;5,4-d]bisthiazol-2-ylamino]-N,N-diethyl-acetamide, ethyl [6-(ethoxycarbonylmethyl-amino)-benzo[1,2-d;5,4-d]bisthiazol-2-ylamino]-acetate, N,N'-bis-(2-diethylamino-ethyl)-benzo[1,2-d;5,4-d]bisthiazole-2,6-diamine, N,N'-bis-(4-diethylamino-1-methyl-butyl)-benzo[1,2-d;5,4-d]bisthiazole-2,6-diamine, N,N'-dimethyl-benzo[1,2-d;5,4-d]bisthiazole-2,6-diamine, N,N'-diethyl-benzo[1,2-d;5,4-d]bisthiazole-2,6-diamine, 4-bromo-N,N'-diethyl-benzo[1,2-d;5,4-d]bisthiazole-2,6-diamine, 4,N,N'-trimethyl-benzo[1,2-d;5,4-d]bisthiazole-2,6-diamine, N,N,N',N'-tetramethyl-benzo[1,2-d;5,4-d]bisthiazole-2,6-diamine, N,N'-dipropyl-benzo[1,2-d;5,4-d]bisthiazole-2,6-diamine, N,N'-diisopropyl-benzo[1,2-d;5,4-d]bisthiazole-2,6-diamine, N,N,N',N'-tetraethyl-benzo[1,2-d;5,4-d]bisthiazole-2,6-diamine and N,N'-diethyl-N,N'-dimethyl-benzo[1,2-d;5,4-d]bisthiazole-2,6-diamine are excluded.

2. The compound according to claim 1, wherein each $R^{4a}$ is selected independently of one another from the group consisting of $R^a$, —OR$^c$, —NR$^c$R$^c$, halogen, —CN, —NO$_2$, —C(O)R$^c$, —C(O)OR$^c$, —C(O)NR$^c$R$^c$ and —N(R$^g$)C(O)R$^c$.

3. The compound of the structure (1C) according to claim 1

(IC)

$R^1$ and/or $R^2$ in each case independently of one another correspond to partial structure (v),

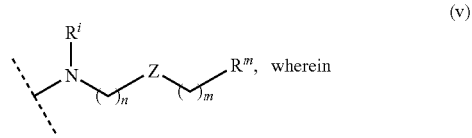
(v)

in the event that both $R^1$ and $R^2$ have the partial structure (v) the two partial structures may be identical or different, Z denotes a methylene group —$CH_2$—, wherein optionally one or both hydrogen atoms may be substituted by $R^j$, $R^i$ may be hydrogen or $C_{1-6}$alkyl, each $R^j$ independently of one another may be selected from the group consisting of $C_{1-6}$alkyl, 2-6 membered heteroalkyl, $C_{3-10}$cycloalkyl, $C_{4-16}$cycloalkylalkyl, $C_{6-10}$aryl, $C_{7-16}$arylalkyl, 6-18 membered heteroarylalkyl, 3-14 membered heterocycloalkyl and 4-14 membered heterocycloalkylalkyl, all the above-mentioned $R^j$ optionally being substituted by one or more identical or different $R^k$, selected independently of one another from the group consisting of $C_{3-10}$cycloalkyl, $C_{6-10}$aryl, 5-12 membered heteroaryl, 3-14 membered heterocycloalkyl, —$OR^c$, —$SR^c$, —$NR^cR^c$, —$ONR^cR^c$, halogen, —CN, —$NO_2$, —C(O)$OR^c$, —C(O)$NR^cR^c$, —OC(O)$R^c$, —OC(O)$OR^c$, —N($R^g$)C(O)$R^c$—N($R^g$)C(O)$OR^c$ and —N($R^g$)C(N$R^g$)N$R^cR^c$, $R^m$ denotes —C(O)N$R''R''$ and $R''$ is selected independently of one another from the group consisting of hydrogen, $C_{1-6}$alkyl, 2-6 membered heteroalkyl, $C_{1-6}$haloalkyl, $C_{3-10}$cycloalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, all the above-mentioned $R''$ optionally being substituted by one or more identical or different $R^o$, $R^o$ is selected independently of one another from the group consisting of $C_{3-10}$cycloalkyl, $C_{6-10}$aryl, 5-12 membered heteroaryl, 3-14 membered heterocycloalkyl, —$OR^p$, —$NR^pR^p$, halogen, —C(O)$OR^p$, —C(O)$NR^pR^p$ and $C_{1-6}$alkyl, the latter optionally being substituted by —C(O)$NR^pR^p$, while $R^p$ is selected independently of one another from the group consisting of hydrogen and $C_{1-6}$alkyl and all the above-mentioned $R^o$, wherever possible, may optionally be substituted by one or more identical or different halogen atom(s), or $NR''R''$ denotes a nitrogen-containing, 3-14 membered heterocycloalkyl or 5-12 membered heteroaryl, while one or more identical or different additional heteroatom(s) may be present, optionally substituted by one or more identical or different $R^q$, $R^q$ is selected independently of one another from the group consisting of $C_{1-6}$alkyl, 2-6 membered heteroalkyl, $C_{3-10}$cycloalkyl, $C_{6-10}$aryl, $C_{7-16}$arylalkyl, 6-18 membered heteroarylalkyl, 3-14 membered heterocycloalkyl, 4-14 membered heterocycloalkyl-alkyl, =O, —$OR^r$, —$NR^rR^r$, halogen, —S(O)$_2R^r$, —C(O)$R^r$, —C(O)$OR^r$ and —C(O)$NR^rR^r$, while all the above-mentioned $R^q$, wherever possible, may optionally be substituted by one or more identical or different group(s), selected independently of one another from the group consisting of $C_{1-6}$alkyl, $C_{6-10}$aryl, 5-12 membered heteroaryl, 3-14 membered heterocycloalkyl, —$OR^r$, —$NR^rR^r$, halogen and —C(O)$NR^rR^r$ and $R^r$ denotes hydrogen or $C_{1-6}$alkyl, m and n each independently of one another have the value 0, 1, 2, 3, 4 or 5 and m+n is equal to 0, 1, 2, 3, 4 or 5 and the group selected from $R^1$ and $R^2$ which does not correspond to a partial structure (v) as well as $R^{4a}$, $R^c$ and $R^g$ are defined as in claim 1.

4. The compound according to claim 3, wherein one of the groups $R^1$ or $R^2$ corresponds to the partial structure (v) and the remaining second group $R^1$ or $R^2$ is —N($R^s$)S(O)$_2R^t$, wherein $R^s$ denotes hydrogen or $C_{1-6}$alkyl and $R^t$ is selected independently of one another from the group consisting of $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl and 5-12 membered heteroaryl, all the above-mentioned $R^t$ optionally being substituted by one or more identical or different $R^u$, $R^u$ is selected independently of one another from the group consisting of $C_{1-6}$alkyl, $C_{6-10}$aryl, —$NR^vR^v$ and halogen, while all the above-mentioned $R^u$, wherever possible, may optionally be substituted by one or more identical or different group(s), selected from the group consisting of $C_{1-6}$alkyl and halogen, and $R^v$ denotes $C_{1-6}$alkyl.

5. The compound according to claim 3, wherein one of the groups $R^1$ or $R^2$ corresponds to the partial structure (v) and the remaining second group $R^1$ or $R^2$ in each case corresponds to —$NR^sR^s$, wherein $R^s$ is selected independently of one another from the group consisting of hydrogen, $C_{1-6}$alkyl, 2-6 membered heteroalkyl, $C_{1-6}$haloalkyl, $C_{6-10}$aryl, $C_{7-16}$arylalkyl, 6-18 membered heteroarylalkyl and 4-14 membered heterocycloalkyl-alkyl, all the above-mentioned $R^s$ optionally being substituted by one or more identical or different $R^t$, $R^t$ is selected from the group consisting of $C_{1-6}$alkyl, $C_{1-6}$haloalkyl, $C_{6-10}$aryl, 5-12 membered heteroaryl, 3-14 membered heterocycloalkyl, =O, —OH, —$NR''R''$ and halogen, wherein all the above-mentioned $R^t$, wherever possible, may optionally be substituted by one or more identical or different group(s), selected from the group consisting of $C_{1-6}$alkyl, =O and halogen, and $R^u$ independently of one another denote hydrogen or $C_{6-10}$aryl.

6. The compound according to claim 3, wherein both $R^1$ and $R^2$ correspond to the partial structure (v) and may be identical or different.

7. The compound of structure (1C) according to claim 1

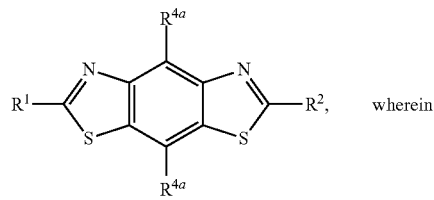
(1C)

$R^1$ and $R^2$ independently of one another are selected from the group consisting of —$NR^aR^a$, —N($R^g$)S(O)$_2R^a$ and a nitrogen-containing 3-8 membered heterocycloalkyl attached via a cyclic nitrogen, this heterocycloalkyl optionally being substituted by one or more identical or different group(s) selected from the group consisting of $R^a$ and $R^b$, each $R^{4a}$ is selected independently of one another from the group consisting of $R^a$ and $R^b$,
optionally in the form of tautomers, racemates, enantiomers, diastereomers and mixtures thereof, and optionally pharmacologically acceptable salts thereof,
with the provisos that
(a) neither $R^1$ nor $R^2$ corresponds to the amino group —$NH_2$,
(b) one of the two groups $R^{4a}$ does not correspond to hydrogen and
(c) the compounds
4-bromo-N,N'-diethyl-benzo[1,2-d;5,4-d]bisthiazole-2,6-diamine and
4,N,N'-trimethyl-benzo[1,2-d;5,4-d]bisthiazole-2,6-diamine
are excluded.

8. A pharmaceutical composition comprising one or more compounds—or the pharmacologically acceptable salts thereof—of formulae (1C) according to claim 1 together with a conventional excipient or carrier.

9. The pharmaceutical composition of claim 8 further comprising at least one other cytostatic or cytotoxic active substance, different from the compound of formula (1C).

* * * * *